US012790646B2

(12) United States Patent
Woodward et al.

(10) Patent No.: US 12,790,646 B2
(45) Date of Patent: Nov. 10, 2026

(54) METHODS FOR DETECTING, MONITORING, AND GUIDING TREATMENT OF ALLOGRAFT REJECTION USING DISCRIMINATING GENE EXPRESSION SIGNATURES

(71) Applicant: CareDx, Inc., Brisbane, CA (US)

(72) Inventors: Robert Woodward, Pleasanton, CA (US); Hua Xu, Sunnyvale, CA (US); Xia Jin, San Francisco, CA (US); David Hiller, Mountlake Terrace, WA (US)

(73) Assignee: CareDx, Inc., Brisbane, CA (US)

( * ) Notice: Subject to any disclaimer, the term of this patent is extended or adjusted under 35 U.S.C. 154(b) by 1148 days.

(21) Appl. No.: 17/733,762

(22) Filed: Apr. 29, 2022

(65) Prior Publication Data

US 2022/0356521 A1 Nov. 10, 2022

Related U.S. Application Data

(60) Provisional application No. 63/246,222, filed on Sep. 20, 2021, provisional application No. 63/182,655, filed on Apr. 30, 2021.

(51) Int. Cl.
*C12Q 1/6876* (2018.01)
*G16H 50/30* (2018.01)

(52) U.S. Cl.
CPC ........... *C12Q 1/6876* (2013.01); *G16H 50/30* (2018.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 11,767,559 B2 | | 9/2023 | Woodward et al. | |
| 2013/0116578 A1* | | 5/2013 | An | A61B 5/7275 600/484 |
| 2015/0191787 A1 | | 7/2015 | Muthukumar et al. | |
| 2016/0145682 A1* | | 5/2016 | Woodward | C12Q 1/6876 506/4 |
| 2022/0081715 A1 | | 3/2022 | Naesens et al. | |
| 2024/0132960 A1 | | 4/2024 | Demko et al. | |

FOREIGN PATENT DOCUMENTS

| | | | |
|---|---|---|---|
| EP | 3146077 | A1 | 3/2017 |
| EP | 2668287 | B1 | 9/2017 |
| EP | 2633078 | B1 | 6/2018 |
| WO | WO-2014074501 | A1 | 5/2014 |
| WO | WO-2015179777 | A2 | 11/2015 |
| WO | WO-2020148358 | A1 | 7/2020 |
| WO | WO-2022232609 | A1 | 11/2022 |

OTHER PUBLICATIONS

Deng (American Journal of Transplantation 2006 vol. 6 pp. 150-160).*
Bloom (J Am Soc Nephrol Mar. 9, 2017; 28(7) pp. 2221-2232).*
Coenye (Biofilm 3 (Jan. 13, 2021) 100043).*
Dedrick (Journal of Immunotoxicology 4:201-207, 2007).*
Wong (Expert Opinion on Emerging Drugs 22:2 123-136).*
Baker et al., (2017). “Renal association clinical practice guideline in post-operative care in the kidney transplant recipient,” BMC Nephrol., 18(1):174, 41 pages.
Bloom et al., (2017). “Cell-Free DNA and Active Rejection in Kidney Allografts,” J Am Soc Nephrol., 28(7):2221-2232.
Bontha et al., (2017). “Systems Biology in Kidney Transplantation: The Application of Multi-Omics to a Complex Model,” Am. J. Transplant., 17(1):11-21.
Chu et al., (2010). “A novel approach toward the challenge of accurately quantifying fetal DNA in maternal plasma,” Prenatal Diagnosis, 30:1226-1229.
ClinicalTrials.gov, (2018). “Non Invasive Blood Test To Diagnose Acute Rejection After Kidney Transplantation (DART); Identifier: NCT02424227,” available online at <https://clinicaltrials.gov/ct2/show/NCT02424227>, 8 pages.
Cravedi et al., (2009). “Noninvasive methods to assess the risk of kidney transplant rejection,” Expert Rev. Clin. Immunol., 5(5):535-546, 19 pages.
Dedrick et al., (2007). “Understanding gene expression patterns in immune-mediated disorders,” J Immunotoxicol., 4(3):201-7.
Deng et al., (2017). “The AlloMap™ genomic biomarker story: 10 years after,” Clin Transplant., 31(3):e12900, 9 pages.
Deng et al., (2006). “Noninvasive discrimination of rejection in cardiac allograft recipients using gene expression profiling,” Am J Transplant., 6(1):150-60.
Dorr et al., (2015). “Differentially expressed gene transcripts using RNA sequencing from the blood of immunosuppressed kidney allograft recipients,” PLoS One, 10(5):e0125045, 14 pages.
Grskovic et al., (2016). “Validation of a Clinical-Grade Assay to Measure Donor-Derived Cell-Free DNA in Solid Organ Transplant Recipients,” J Mol Diagn., 18(6):890-902.
Haas et al., (2017). “The Banff 2017 Kidney Meeting Report: Revised diagnostic criteria for chronic active T cell-mediated rejection, antibody-mediated rejection, and prospects for integrative endpoints for next-generation clinical trials,” Am J Transplant., 18(2):293-307.
Hart et al., (2018). “OPTN/SRTR 2016 Annual Data Report: Kidney,” Am J Transplant., 18(Suppl 1):18-113, 96 pages.

(Continued)

*Primary Examiner* — Amanda Haney
(74) *Attorney, Agent, or Firm* — Wilson Sonsini Goodrich & Rosati

(57) ABSTRACT

Methods and kits are provided for detecting and discriminating between immune quiescence and allograft rejections, such as T cell-mediated rejection and antibody-mediated rejection, using differential gene expression signatures alone or in combination with levels of transplant-derived cell-free nucleic acids.

6 Claims, 24 Drawing Sheets

(56) References Cited

OTHER PUBLICATIONS

Jordan et al., (2018). "Donor-derived Cell-free DNA Identifies Antibody-mediated Rejection in Donor Specific Antibody Positive Kidney Transplant Recipients," Transplant Direct, 4:e379, 5 pages.
Kurian et al., (2014). "Molecular classifiers for acute kidney transplant rejection in peripheral blood by whole genome gene expression profiling," Am J Transplant., 14(5):1164-72.
Li et al., (2012). "A peripheral blood diagnostic test for acute rejection in renal transplantation," Am J Transplant, 12(10):2710-8.
Liu et al. (2012). "Comparison of next-generation sequencing systems," J of Biomedicine and Biotechnology, 2012:251364, 11 pages.
Lo et al., (2014). "Biomarkers for kidney transplant rejection," Nat. Rev. Nephrol., 10(4):215-225.
Loupy et al., (2020). "The Banff 2019 Kidney Meeting Report (I): Updates on and clarification of criteria for T cell- and antibody-mediated rejection," Am. J. Transplant., 20(9):2318-2331.
Mamlouk et al., (2021). "Safety of CAR T-cell therapy in kidney transplant recipients," Blood, 137(18):2558-2562.
Mas et al., (2011). "Identifying biomarkers as diagnostic tools in kidney transplantation," Expert Rev Mol Diagn., 11(2):183-96, 24 pages.
Mehta et al., (2017). "Kidney allograft surveillance biopsy practices across US transplant centers: A UNOS survey," Clin. Transplant., 31(5):e12945, 7 pages.
Moreso et al., (2006). "Subclinical rejection associated with chronic allograft nephropathy in protocol biopsies as a risk factor for late graft loss," Am J Transplant., 6(4):747-52.
Morgan et al., (2016). "Complications of Ultrasound-Guided Renal Transplant Biopsies," Am J Transplant., 16(4):1298-305.
Naesens et al., (2011). "Progressive histological damage in renal allografts is associated with expression of innate and adaptive immunity genes," Kidney Int., 80(12):1364-76.
Oeth et al., (2009). "Qualitative and quantitative genotyping using single base primer extension coupled with matrix-assisted laser desorption/ionization time-of-flight mass spectrometry (MassARRAY)," Methods Mol Biol., 578:307-43.
Oyelade et al., (2016). "Clustering Algorithms: Their Application to Gene Expression Data," Bioinform Biol Insights., 10:237-253.
Pakstis et al., (2010). "SNPs for a universal individual identification panel," Hum Genet., 127(3):315-24.
Peng et al., (2015). "Reducing amplification artifacts in high multiplex amplicon sequencing by using molecular barcodes," BMC Genomics, 16:589, 12 pages.
Pham et al., (2010). "Gene-Expression Profiling for Rejection Surveillance after Cardiac Transplantation," N Engl J Med, 362(20):1890-1900.
Plattner et al., (2018). "Complications and adequacy of transplant kidney biopsies: A comparison of techniques," J Vasc Access., 19(3):291-296.
Pontrelli et al., (2020). "The Role of Natural Killer Cells in the Immune Response in Kidney Transplantation," Front. Immunol., 11:1454, 10 pages.
Quail et al., (2012). "A tale of three next generation sequencing platforms: comparison of Ion Torrent, Pacific Biosciences and Illumina MiSeq sequencers," BMC Genomics, 13(1):341, 13 pages.
Reschen et al., (2018). "A retrospective analysis of the utility and safety of kidney transplant biopsies by nephrology trainees and consultants," Ann Med Surg (Lond), 28:6-10.
Stein, (2008). "Exploiting Advances in Image Analysis," Genetic Engineering & Biotechnology News, 28(18), 6 pages.
Stites et al., (2020). "High levels of dd-cfDNA identify patients with TCMR 1A and borderline allograft rejection at elevated risk of graft injury," Am J Transplant., 20(9):2491-2498.
Suzuki et al., (2008). "Characterization of circulating DNA in healthy human plasma," Clinica Chimica Acta, 387:55-8.
Thongprayoon et al., (2020). "Recent Advances and Clinical Outcomes of Kidney Transplantation," J. Clin. Med., 9(4):1193, 18 pages.
Van Loon et al., (2021). "Diagnostic performance of kSORT, a blood-based mRNA assay for noninvasive detection of rejection after kidney transplantation: A retrospective multicenter cohort study," Am J Transplant., 21(2):740-750.
Van Loon et al., (2019). "Development and validation of a peripheral blood mRNA assay for the assessment of antibody-mediated kidney allograft rejection: A multicentre, prospective study," EBioMedicine, 46:463-472.
Wolf-Doty et al., (2021). "Dynamic Response of Donor-Derived Cell-Free DNA Following Treatment of Acute Rejection in Kidney Allografts," Kidney360, 2(4):729-736.
Wong et al., (2020). "The Evolution and Innovation of Donor-Derived Cell-Free DNA Testing in Transplantation," J Med Diagn Meth., 9(5):302, 5 pages.
Xie et al., (2021). "Causes of Renal Allograft Injury in Recipients With Normal Donor-derived Cell-free DNA," Transplant Direct., 7(4):e679, 7 pages.
Zhang et al., (2019). "A Peripheral Blood Gene Expression Signature to Diagnose Subclinical Acute Rejection," J Am Soc Nephrol., 30(8):1481-1494.
Akalin et al., (2021). "Clinical Validation of an Immune Quiescence Gene Expression Signature in Kidney Transplantation," Kidney360, 2(12):1998-2009, 17 pages.
Christakoudi et al., (2019). "Development of a multivariable gene-expression signature targeting T-cell-mediated rejection in peripheral blood of kidney transplant recipients validated in cross-sectional and longitudinal samples," Ebiomedicine, 41:571-583.
Crespo-Leiro et al., (2015). "Increased Plasma Levels of Donor-Derived Cell-Free DNA Correlate With Rejection in Heart Transplant Recipients: The Cargo II Multicenter Trial," The Journal of Heart and Lung Transplantation, 34(4):S31-S32.
Dharnidharka et al., (2017). "Biomarkers to detect rejection after kidney transplantation," Pediatric Nephrology, 33(7):1113-1122.
Kanwar et al., (2020). "Impact of cytomegalovirus infection on gene expression profile in heart transplant recipients," Journal Of Heart And Lung Transplantation, 40(2):101-107.
Sigdel et al., (2019). "Assessment of 19 Genes and Validation of CRM Gene Panel for Quantitative Transcriptional Analysis of Molecular Rejection and Inflammation in Archival Kidney Transplant Biopsies," Frontiers In Medicine, 6:213, 10 pages.
Affymetrix GeneChip Human Genome U133 Array Set HG-U133A, Geo Expression, Mar. 11, 2002 (XP002361324).
Akiyoshi, Takurin et al. Role of complement and NK cells in antibody mediated rejection. Human immunology 73(12):1226-1232 (2012).
Alakulppi, Noora S. et al. Diagnosis of acute renal allograft rejection by analyzing whole blood mRNA expression of lymphocyte marker molecules. Transplantation 83(6):791-798 (2007).
Amore, Alessandro. Antibody-mediated rejection. Current opinion in organ transplantation 20(5):536-542 (2015).
Ashton-Chess, Joanna. et al. Tribbles-1 as a novel biomarker of chronic antibody-mediated rejection. Journal of the American Society of Nephrology 19(6):1116-1127 (2008).
Blydt-Hansen, Tom D. et al. Urinary Metabolomics for Noninvasive Detection of Antibody-Mediated Rejection in Children After Kidney Transplantation. Transplantation 101(10):2553-2561 (2017).
Breiman, Leo. Random Forests. Machine Learning 45(1):5-32 (2001).
Burns, J. M. et al. Alloantibody levels and acute humoral rejection early after positive crossmatch kidney transplantation. American Journal of Transplantation 8(12):2684-2694 (2008).
Chun, Hyonho, and Sunduz Keles. Sparse partial least squares regression for simultaneous dimension reduction and variable selection. Journal of the Royal Statistical Society Series B: Statistical Methodology 72(1):3-25 (2010).
Clinical Trials.gov, (2018). "Non Invasive Blood Test To Diagnose Acute Rejection After Kidney Transplantation (DART); Identifier: NCT02424227," available online at https://clinicaltrials.gov/study/NCT02424227. 11 pages.
ClinicalTrials.gov Identifier: NCT03326076. Evaluation of Patient Outcomes From the Kidney Allograft Outcomes AlloSure Registry

(56) References Cited

OTHER PUBLICATIONS (KOAR), Record created Oct. 25, 2017. pp. 1-18. [retrieved on Oct. 14, 2025] Available at URL: https://clinicaltrials.gov/study/NCT03326076.
Colvin, Robert B, and Smith, R. Neal. Antibody-mediated organ-allograft rejection. Nature Reviews Immunology 5(10):807-817 (2005).
Co-pending U.S. Appl. No. 19/667,608, inventors Naesens; Maarten et al., filed May 4, 2026.
Cosio, Fernando G. et al. Significance and Implications of Capillaritis during Acute Rejection of Kidney Allografts. Transplantation 89(9):1088-1094 (2010).
Dean, P. G. et al. Intragraft gene expression in positive crossmatch kidney allografts: ongoing inflammation mediates chronic antibody-mediated injury. American Journal of Transplantation 12(6):1551-1563 (2012).
Djamali, A. et al. Diagnosis and management of antibody-mediated rejection: current status and novel approaches. American journal of transplantation 14(2):255-271 (2014).
Drachenberg, Cinthia B, and John C Papadimitriou. Endothelial injury in renal antibody-mediated allograft rejection: a schematic view based on pathogenesis. Transplantation 95(9):1073-1083 (2013).
El-Zoghby, Z. M. et al. Identifying specific causes of kidney allograft loss. American Journal of Transplantation 9(3):527-535 (2009). Published Online Feb. 3, 2008.
Fahim, T. et al. The cellular lesion of humoral rejection: predominant recruitment of monocytes to peritubular and glomerular capillaries. American Journal of Transplantation 7(2):385-393 (2007).
Fehr, Thomas, and Ariana Gaspert. Antibody-mediated kidney allograft rejection: therapeutic options and their experimental rationale. Transplant International 25(6):623-632 (2012).
Gibson, I. W. et al. Peritubular capillaritis in renal allografts: prevalence, scoring system, reproducibility and clinicopathological correlates. American Journal of Transplantation 8(4):819-825 (2008).
Grey, Daniel. et al. Increased CD64 expression on polymorphonuclear neutrophils indicates infectious complications following solid organ transplantation. Cytometry Part A 79(6):446-460 (2011).
Guyon, Isabelle, et al. Gene selection for cancer classification using support vector machines. Machine Learning 46:389-422 (2002).
Halloran, P F. et al. The molecular phenotype of kidney transplants. American journal of transplantation 10(10):2215-2222 (2010).
Halloran, Philip F. et al. Review: The transcripts associated with organ allograft rejection. American journal of transplantation 18(4):785-795 (2018). Published Online Dec. 23, 2017.
Halloran, Philip F. et al. The significance of the anti-class I antibody response: I. Clinical and pathologic features of anti-class I-mediated rejection. Transplantation 49(1):85-91 (1990).
Hollander, Zsuzsanna. et al. Whole blood biomarkers of acute cardiac allograft rejection: double-crossing the biopsy. Transplantation 90(12):1388-1393 (2010).
Hummert, C. et al. Creation and Comparison of Different Chip Definition Files for Affymetrix Microarrays. 2011 International Conference on Bioinformatics & Computational Biology 1:16-22 (2011).
Kim, Miae. et al. Antibody-mediated rejection in kidney transplantation: a review of pathophysiology, diagnosis, and treatment options. Pharmacotherapy: The Journal of Human Pharmacology and Drug Therapy 34(7):733-744 (2014).
Kulkarni, S. et al. Eculizumab Therapy for Chronic Antibody-Mediated Injury in Kidney Transplant Recipients: A Pilot Randomized Controlled Trial. American journal of transplantation 17(3):682-691 (2017). Published online on Sep. 2016.
Loupy, A., et al. The Banff 2015 kidney meeting report: current challenges in rejection classification and prospects for adopting molecular pathology. American journal of transplantation 17(1):28-41 (2017).
Loupy, Alexandre, and Carmen Lefaucheur. Antibody-mediated rejection of solid-organ allografts. New England Journal of Medicine 379(12):1150-1160 (2018).
Loupy, Alexandre. et al. Subclinical rejection phenotypes at 1 year post-transplant and outcome of kidney allografts. Journal of the American Society of Nephrology 26(7):1721-1731 (2015).
Loupy, Alexandre. et al. The impact of donor-specific anti-HLA antibodies on late kidney allograft failure. Nature reviews Nephrology 8(6):348-357 (2012).
Mandelbrodt, Didier A, and Mohamed H. Sayegh. Chapter 2: Transplantation Immunobiology. Handbook of Kidney Transplantation :19-35 (2010).
Mao, Youying. et al. CXCL10 and CXCL13 Expression were highly up-regulated in peripheral blood mononuclear cells in acute rejection and poor response to anti-rejection therapy. Journal of clinical immunology 31(3):414-418 (2011). Published Online on Dec. 30, 2010.
Matignon, Marie. et al. Urinary cell mRNA profiles and differential diagnosis of acute kidney graft dysfunction. J Am Soc Nephrol 25(7):1586-1597 (2014).
Naesens, Maarten, and Dany Anglicheau. Precision Transplant Medicine: Biomarkers to the Rescue. Journal of the American Society of Nephrology 29(1):24-34 (2018). Published Online Oct. 9, 2017.
Naesens, Maarten. et al. Proteinuria as a noninvasive marker for renal allograft histology and failure: an observational cohort study. Journal of the American Society of Nephrology 27(1):281-292 (2016). Published Online Jul. 5, 2015.
Naesens, Maarten. et al. The histology of kidney transplant failure: a long-term follow-up study. Transplantation 98(4):427-435 (2014).
Nankivell, Brian J, and Stephen I Alexander. Rejection of the kidney allograft. The New England journal of medicine 363(15):1451-1462 (2010).
Parlato, Marianna, and Jean-Marc Cavaillon. Chapter 15: Host response biomarkers in the diagnosis of sepsis: A general overview. Sepsis: Diagnostic Methods and Protocols, Methods in Molecular Biology 1237:149-211 (2015).
PCT/EP2020/050959 International Search Report and Written Opinion dated Feb. 21, 2020.
PCT/US2022/027079 International Search Report and Written Opinion dated Aug. 5, 2022.
Pierson-Perry, James F. et al. Evaluation of Detection Capability for Clinical Laboratory Measurement Procedures; Approved Guideline—Second Edition. Clinical and Laboratory Standards Institute EP17-A2, 32(8). (Replaces EP17-A, 24(34)) 1-80 (2012).
Rabant, Marion. et al. Urinary C-X-C Motif Chemokine 10 Independently Improves the Noninvasive Diagnosis of Antibody-Mediated Kidney Allograft Rejection. Journal of the American Society of Nephrology 26(11):2840-2851 (2015).
Racusen, Lorraine C, and Haas, Mark. Antibody-mediated rejection in renal allografts: lessons from pathology. Clinical journal of the American Society of Nephrology 1(3):415-420 (2006).
Resch, Thomas. et al. The Role of Natural Killer Cells in Humoral Rejection. Transplantation 99(7):1335-1340 (2015).
Rinaudo, Philippe. et al. Biosigner: a new method for the discovery of significant molecular signatures from omics data. Frontiers in molecular biosciences 3:26, 1-14 (2016).
Roedder, Silke. et al. The kSORT assay to detect renal transplant patients at high risk for acute rejection: results of the multicenter AART study. PLoS medicine 11(11):e1001759, 1-15 (2014).
Sandal, Shaifali, and Martin S Zand. Rational clinical trial design for antibody mediated renal allograft injury. Frontiers in bioscience (Landmark edition) 20(4):743-762 (2015).
Sellares, J. et al. Understanding the causes of kidney transplant failure: the dominant role of antibody-mediated rejection and non-adherence. American Journal of Transplantation 12(2):388-399 (2012). Published Online Nov. 14, 2011.
Shapiro-Shelef, Miriam, and Calame, Kathryn. Regulation of plasma-cell development. Nature Reviews Immunology 5(3):230-242 (2005).
Singleton, Paul. Dictionary of DNA and Genome Technology, Third Edition. Wiley-Blackwell (2012).
Sis, B. et al. A New Diagnostic Algorithm for Antibody-Mediated Microcirculation Inflammation in Kidney Transplants. American journal of transplantation 12(5):1168-1179 (2012).

(56) References Cited

OTHER PUBLICATIONS

Sis, Banu. et al. Endothelial gene expression in kidney transplants with alloantibody indicates antibody-mediated damage despite lack of C4d staining. American journal of transplantation 9(10):2312-2323 (2009).
Slavcev, Antonij. et al. Soluble BAFF Cytokine Levels and Antibody-Mediated Rejection of the Kidney Allograft. Archivum immunologiae et therapiae experimentalis 64(Suppl 1):47-53 (2016). Published Online Jan. 12, 2017.
Stein, Richard A. Next-Generation Sequencing Update. 28(15): Sep. 1, 2008; [retrieved on Nov. 20, 2024] Available at URL:https://www.genengnews.com/insights/next-generation-sequencing-update/ pp. 1-7.
Takemoto, Steven K. et al. National conference to assess antibody-mediated rejection in solid organ transplantation. American Journal of Transplantation 4(7):1033-1041 (2004).
The R Project for Statistical Computing. [retrieved on Nov. 20, 2025]. Available at URL: https://www.r-project.org/ pp. 1-2.
Tibshirani, Robert. et al. Diagnosis of multiple cancer types by shrunken centroids of gene expression. Proceedings of the National Academy of Sciences 99(10):6567-6572 (2002).
U.S. Appl. No. 17/420,347 Office Action dated Mar. 16, 2026.
U.S. Appl. No. 17/420,347 Office Action dated Sep. 19, 2025.
U.S. Appl. No. 17/420,347 Restriction Requirement dated Jan. 17, 2025.
Veale, Jeffrey L. et al. Noninvasive diagnosis of cellular and antibody-mediated rejection by perforin and granzyme B in renal allografts. Human immunology 67(10):777-786 (2006).
Vickers, Andrew J., and Elena B. Elkin. Decision curve analysis: a novel method for evaluating prediction models. Medical Decision Making 26(6):565-574 (2006).
Vickers, Andrew J. et al. Net benefit approaches to the evaluation of prediction models, molecular markers, and diagnostic tests. bmj 352:i6, 1-5 (2016).
Wang, Anyou, and Minnie M. Sarwal. Computational models for transplant biomarker discovery. Frontiers in Immunology 6:458, 1-9 (2015).
Williams, G. Melville. et al. Hyperacute renal-homograft rejection in man. New England journal of medicine 279(12):611-618 (1968).
Xu, Joshua. et al. Cross-platform ultradeep transcriptomic profiling of human reference RNA samples by RNA-Seq. Scientific data 1:140020, 1-8 (2014).
Yan, Qiang. et al. Expression of MMP-2 and TIMP-1 in renal tissue of patients with chronic active antibody-mediated renal graft rejection. Diagnostic pathology 7(1):141, 1-6 (2012).
Yazdani, Saleh. et al. Natural killer cell infiltration is discriminative for antibody-mediated rejection and predicts outcome after kidney transplantation. Kidney International 95(1):188-198 (2019). Published Online Nov. 3, 2018.
Zou, Hui, and Trevor Hastie. Regularization and variable selection via the elastic net. Journal of the Royal Statistical Society Series B: Statistical Methodology 67(2):301-320 (2005).

* cited by examiner

FIG. 14A

A

| GEP score | Sensitivity | Specificity | PPV_10 | NPV_10 | PPV_25 | NPV_25 |
|---|---|---|---|---|---|---|
| 0.0 | 100.0% | 0.0% | 10.0% | NC | 25.0% | NC |
| 0.5 | 100.0% | 0.0% | 10.0% | NC | 25.0% | NC |
| 1.0 | 100.0% | 0.0% | 10.0% | NC | 25.0% | NC |
| 1.5 | 100.0% | 1.0% | 10.0% | 100.0% | 25.0% | 100.0% |
| 2.0 | 100.0% | 1.0% | 10.0% | 100.0% | 25.0% | 100.0% |
| 2.5 | 100.0% | 1.0% | 10.0% | 100.0% | 25.0% | 100.0% |
| 3.0 | 100.0% | 1.0% | 10.0% | 100.0% | 25.0% | 100.0% |
| 3.5 | 100.0% | 2.0% | 10.0% | 100.0% | 25.0% | 100.0% |
| 4.0 | 100.0% | 3.0% | 10.0% | 100.0% | 26.0% | 100.0% |
| 4.5 | 100.0% | 5.0% | 10.0% | 100.0% | 26.0% | 100.0% |
| 5.0 | 98.0% | 7.0% | 11.0% | 98.0% | 26.0% | 93.0% |
| 5.5 | 98.0% | 12.0% | 11.0% | 99.0% | 27.0% | 96.0% |
| 6.0 | 98.0% | 17.0% | 12.0% | 99.0% | 28.0% | 97.0% |
| 6.5 | 97.0% | 20.0% | 12.0% | 98.0% | 29.0% | 95.0% |
| 7.0 | 94.0% | 25.0% | 13.0% | 97.0% | 29.0% | 92.0% |
| 7.5 | 92.0% | 31.0% | 13.0% | 97.0% | 31.0% | 93.0% |
| 8.0 | 91.0% | 38.0% | 14.0% | 97.0% | 33.0% | 93.0% |
| 8.5 | 88.0% | 45.0% | 15.0% | 97.0% | 35.0% | 92.0% |
| 9.0 | 86.0% | 52.0% | 17.0% | 97.0% | 38.0% | 92.0% |
| 9.5 | 76.0% | 57.0% | 16.0% | 95.0% | 37.0% | 88.0% |
| 10.0 | 71.0% | 62.0% | 17.0% | 95.0% | 39.0% | 87.0% |
| 10.5 | 70.0% | 66.0% | 18.0% | 95.0% | 40.0% | 86.0% |
| 11.0 | 61.0% | 71.0% | 19.0% | 94.0% | 41.0% | 84.0% |
| 11.5 | 50.0% | 82.0% | 23.0% | 94.0% | 48.0% | 83.0% |
| 12.0 | 41.0% | 85.0% | 23.0% | 93.0% | 47.0% | 81.0% |
| 12.5 | 32.0% | 89.0% | 24.0% | 92.0% | 49.0% | 80.0% |
| 13.0 | 21.0% | 90.0% | 19.0% | 91.0% | 41.0% | 77.0% |
| 13.5 | 21.0% | 93.0% | 27.0% | 91.0% | 52.0% | 78.0% |
| 14.0 | 18.0% | 95.0% | 28.0% | 91.0% | 53.0% | 78.0% |
| 14.5 | 12.0% | 97.0% | 31.0% | 91.0% | 58.0% | 77.0% |
| 15.0 | 11.0% | 99.0% | 67.0% | 91.0% | 86.0% | 77.0% |
| 15.5 | 9.0% | 99.0% | 63.0% | 91.0% | 84.0% | 77.0% |
| 16.0 | 8.0% | 99.0% | 53.0% | 90.0% | 77.0% | 76.0% |
| 16.5 | 6.0% | 99.0% | 53.0% | 90.0% | 77.0% | 76.0% |
| 17.0 | 5.0% | 100.0% | 100.0% | 90.0% | 100.0% | 76.0% |
| 17.5 | 3.0% | 100.0% | 100.0% | 90.0% | 100.0% | 76.0% |
| 18.0 | 0.0% | 100.0% | NC | 90.0% | NC | 75.0% |
| 18.5 | 0.0% | 100.0% | NC | 90.0% | NC | 75.0% |
| 19.0 | 0.0% | 100.0% | NC | 90.0% | NC | 75.0% |
| 19.5 | 0.0% | 100.0% | NC | 90.0% | NC | 75.0% |
| 20.0 | 0.0% | 100.0% | NC | 90.0% | NC | 75.0% |

*NC = not computable

FIG. 14B

B

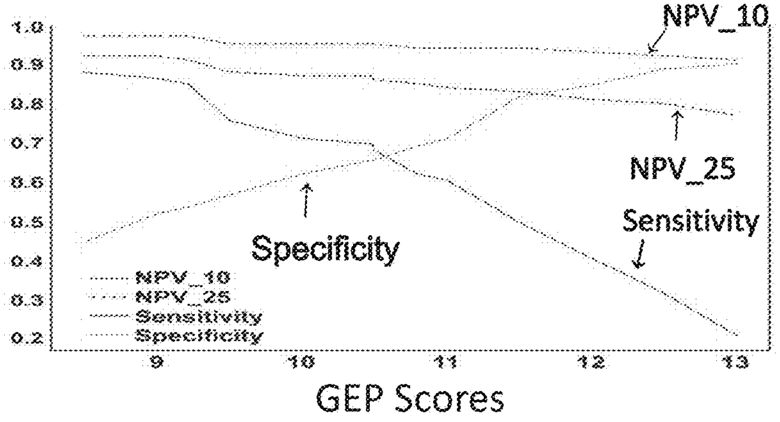

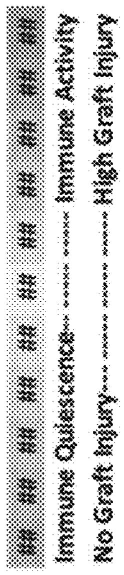
Explanatory key for FIGS. 17A-C
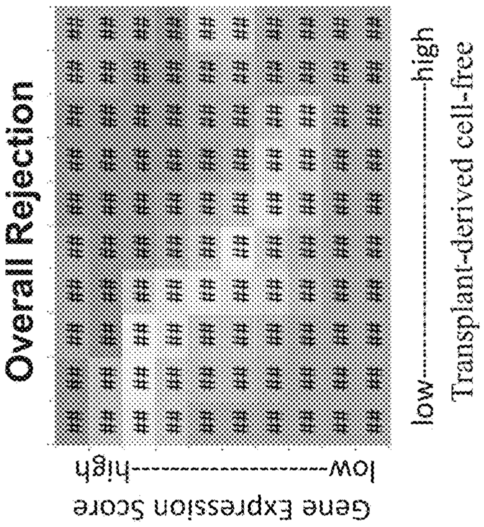
FIG. 17A
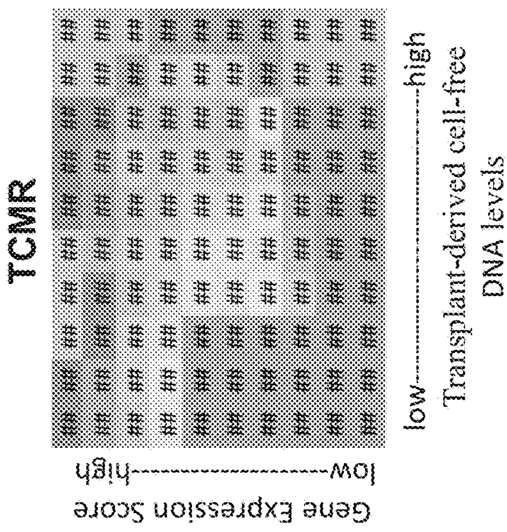
FIG. 17B
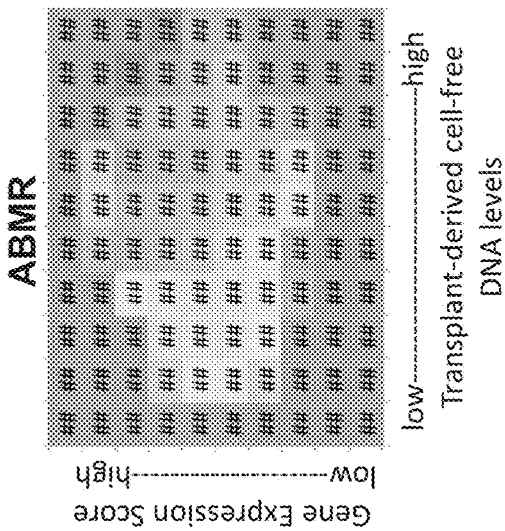
FIG. 17C

METHODS FOR DETECTING, MONITORING, AND GUIDING TREATMENT OF ALLOGRAFT REJECTION USING DISCRIMINATING GENE EXPRESSION SIGNATURES

CROSS-REFERENCE TO RELATED APPLICATIONS

This application claims the benefit of U.S. Provisional Application No. 63/182,655, filed Apr. 30, 2021, and U.S. Provisional Application No. 63/246,222, filed Sep. 20, 2021, which are hereby incorporated by reference in their entirety.

FIELD

The present invention relates to methods and kits for detecting and monitoring immune quiescence, and for discriminating between immune quiescence and allograft rejection, and to methods and kits for detecting, monitoring, and guiding treatment of allograft rejection in a transplant recipient using discriminating gene expression signatures alone or in combination with transplant-derived cell-free nucleic acids.

BACKGROUND

Solid organ transplantation means for many transplant recipients a new start after years of declining health and declining quality of life. Since most organ transplantations are carried out with organs that are donated by another individual and, thus, non-self or foreign (allograft) to the recipient, the recipient's immune response must be monitored and as needed, controlled with one or more treatments to suppress the immune system as to reduce the risk that the allograft activates the immune system to attack and reject the transplanted organ. The immunosuppressive needs of individual transplant recipients vary and generally require an individualized treatment approach with various check-ups to test whether the selected immunosuppressive treatment is effective to prevent allograft rejection. If the treatment is not effective, the lifetime of the allograft is limited, endangering the life of the transplant recipient and necessitating, if possible, a subsequent organ transplantation.

Scheduled check-up visits of transplant recipients typically include measurements of organ damage, organ function, peak/trough levels of the immunosuppressive drugs in question, and less frequently for-cause or surveillance biopsies of the allograft. However, measurements of the function of organs, such as serum creatinine and estimated glomerular filtration rate for kidneys, are often inconclusive and cannot readily be correlated with the health status of the allograft. Furthermore, the results of for-cause and surveillance biopsies may be biased by the interpretation of the tasked pathologist and the chosen biopsy sites may not provide a comprehensive picture of the overall health of the allograft.

Since graft rejection can be the result of a gradual process during which the transplant recipient's immune system unfolds and since there are various lines of attack on the graft that may or may not ultimately lead to an actual case of rejection, detection of indicators that signal graft rejection or forthcoming graft rejection is critical to save and to prolong the lifespan of the allograft. Long-term allograft failure rates continue to be high, underscoring the need for biomarkers that provide an early indication of processes leading to allograft rejection.

The assessment of the degree of immune activity, where immune quiescence indicates the absence or low levels of immune activity or absence of rejection-associated clinical symptoms, is instrumental in identifying potential interventions that may extend allograft survival but also ruling out pathologies, particularly allograft rejection, that are the consequence of immune activity. Optimizing interventions by assessing their impact through quantifiable measures such as biomarker changes can drive the paradigm shift from reactive to proactive care.

Gene expression signatures or biomarkers indicating immune activity changes, or lack thereof, can be useful for detecting allograft rejection or immune quiescence, and for monitoring a transplant recipient's response to therapeutic intervention or medication adherence.

There is also a need for improved methods to elucidate and differentiate rejection pathogenesis (e.g., T cell mediated vs. antibody-mediated), as the mechanism of pathogenesis may inform the most effective course of clinical treatment to save and prolong the lifespan of the allograft.

SUMMARY OF PREFERRED EMBODIMENTS

The embodiments described in this disclosure address the above-described needs by providing gene expression signatures that, alone or in combination with transplant donor-derived cell-free nucleic acid levels, are capable of detecting or monitoring immune quiescence and differentiating immune quiescence from allograft rejection. Particularly the combined assessment of gene expression signatures and transplant donor-derived cell-free nucleic acid levels provides a further distinction between T cell-mediated (cellular) rejection and antibody-mediated rejection in a transplant recipient.

Disclosed herein are methods and kits for detecting or monitoring immune quiescence, differentiating immune quiescence from allograft rejection, and further, differentiating antibody-mediated rejection from T cell-mediated rejection as well as detecting, monitoring, and guiding treatment of allograft rejection in a transplant recipient, using one or more discriminating gene expression signatures alone or in combination with transplant donor-derived cell-free nucleic acid levels. Further disclosed herein are methods for detecting or monitoring a transplant recipient's medication adherence or compliance.

In any of the embodiments described herein, transplant recipients who exhibit differential gene expression as described in the below exemplary embodiments, can be identified as being immune quiescent, as likely to experience allograft rejection or at risk of allograft rejection as determined by a (computed) gene expression (signature) score alone or by a (computed) combined score that correlates the gene expression score and levels of transplant-derived cell-free nucleic acids.

In one aspect, provided herein is a method of detecting or monitoring immune quiescence in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or below a cut-off value indicates that the transplant recipient is likely experiencing immune quiescence, and d)

detecting immune quiescence if the one or more gene expression score is determined to be equal to or below the cut-off value.

In another aspect, provided herein is a method of discriminating between immune quiescence and active rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely experiencing active rejection or is at risk of developing active rejection, and the one or more gene expression score being below the cut-off value indicates that the transplant recipient is likely experiencing immune quiescence, and d) detecting active rejection if the one or more gene expression score is determined to be equal to or above the cut-off value.

In another aspect, provided herein is a method of discriminating between T cell-mediated rejection and antibody-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a first cut-off value indicates that the transplant recipient is likely experiencing T cell-mediated rejection or is at risk of developing T cell-mediated rejection, and the one or more gene expression score being equal to or above a second cut-off value indicates that the transplant recipient is likely experiencing antibody-mediated rejection or is at risk of developing antibody-mediated rejection, and d) detecting T cell-mediated rejection if the one or more gene expression score is determined to be equal to or above the first cut-off value, and detecting antibody-mediated rejection if the one or more gene expression score is determined to be equal to or above the second cut-off value.

In another aspect, provided herein is a method of discriminating between immune quiescence, T cell-mediated rejection, and antibody-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a first cut-off value indicates that the transplant recipient is likely experiencing T cell-mediated rejection or is at risk of developing T cell-mediated rejection, the one or more gene expression score being equal to or above a second cut-off value indicates that the transplant recipient is likely experiencing antibody-mediated rejection or is at risk of developing antibody-mediated rejection, and the one or more gene expression score being below the first and the second cut-off value indicates that the transplant recipient is likely experiencing immune quiescence, and detecting T cell-mediated rejection if the one or more gene expression score is determined to be equal to or above the first cut-off value, and detecting antibody-mediated rejection if the one or more gene expression score is determined to be equal to or above the second cut-off value.

In another aspect, provided herein is a method of detecting, monitoring, and/or guiding treatment of active rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) wherein the one or more gene expression score being equal to or above a cut-off value indicates that the transplant recipient is likely experiencing active rejection or is at risk of developing active rejection, d) detecting active rejection if the one or more gene expression score is determined to be equal to or above the cut-off value, and e) optionally treating the rejection by administering to the recipient an anti-rejection agent and/or increasing the dosage of an anti-rejection agent that the recipient already received.

In another aspect, provided herein is a method of detecting and distinguishing T cell-mediated rejection from antibody mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely experiencing T cell-mediated rejection or is at risk of developing T cell-mediated rejection, d) detecting T cell mediated rejection if the one or more gene expression score is determined to be equal to or above the cut-off value, and e) optionally treating the rejection by administering to the recipient an anti-rejection agent and/or increasing the dosage of an anti-rejection agent that the recipient already received.

In another aspect, provided herein is a method of assessing the likelihood of allograft rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely to experience allograft rejection or is at risk of developing allograft rejection, and d) predicting allograft rejection if the one or more gene expression score is determined to be equal to or above the cut-off value.

In another aspect, provided herein is a method of assessing the likelihood of antibody-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely to experience antibody-mediated rejection or is at risk of developing antibody-mediated rejection, and d) predicting antibody-mediated rejection if the one or more gene expression score is determined to be equal to or above the cut-off value.

In another aspect, provided herein is a method of assessing the likelihood of T cell-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely to experience T cell-mediated rejection or is at risk of developing T cell-mediated rejection, and d) predicting T cell-mediated rejection if the one or more gene expression score is determined to be equal to or above the cut-off value.

In another aspect, provided herein is a method of discriminating between immune quiescence and a state of immune activation caused by infection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely experiencing a state of immune activation caused by infection or is at risk of developing a state of immune activation caused by infection, and the one or more gene expression score being below the cut-off value indicates that the transplant recipient is likely experiencing immune quiescence, and d) detecting a state of immune activation caused by infection or detecting a risk of developing a state of immune activation if the one or more gene expression score is determined to be equal to or above the cut-off value.

In another aspect, provided herein is a method of detecting or monitoring a transplant recipient's medication adherence, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or below a cut-off value indicates that the transplant recipient likely adheres to a prescribed medication regimen, and wherein the one or more gene expression score being equal to or above a cut-off value indicates that the transplant recipient likely lacks adherence to a prescribed medication regimen, d) detecting medication adherence if the one or more gene expression score is determined to be equal to or below the cut-off value, and detecting lack of medication adherence if the one or more gene expression score is determined to be equal to or above the cut-off value.

In some embodiments, the transplant recipient has no clinically indicated need for a biopsy.

In some embodiments, the transplant recipient has a clinically indicated need for a biopsy.

In some embodiments, the one or more genes associated with an immune response-regulating pathway of inflammation, corticosteroid sensitivity, and/or T cell activation comprises at least one gene selected from the group consisting of DCAF12, FLT3, IL1R2, PDCD1, and MARCH8.

In some embodiments, step b) further comprises determining expression levels of one or more genes with expression that correlates with the expression of the one or more genes associated with an immune response-regulating pathway of inflammation, corticosteroid sensitivity, and/or T cell activation, and step c) further comprises applying a trained classifier to the expression levels of the one or more genes with correlating expression to obtain one or more gene expression scores.

In some embodiments, the one or more genes associated with an immune response-regulating pathway of inflammation, corticosteroid sensitivity, and/or T cell activation comprises: MARCH8, PDCD1, and DCAF12; FLT3, PDCD1, and DCAF12; FLT3, IL1R2, and DCAF12; IL1R2, MARCH8, and PDCD1; FLT3, MARCH8, and PDCD1; IL1R2, PDCD1, and DCAF12; FLT3, IL1R2, and MARCH8; FLT3, IL1R2, and PDCD1; IL1R2, MARCH8, PDCD1, and DCAF12; FLT3, MARCH8, PDCD1, and DCAF12; FLT3, IL1R2, PDCD1, and DCAF12; FLT3, IL1R2, MARCH8, and DCAF12; or FLT3, IL1R2, MARCH8, and PDCD1.

In some embodiments, the one or more genes associated with an immune response-regulating pathway of inflammation, corticosteroid sensitivity, and/or T cell activation comprises DCAF12, FLT3, IL1R2, PDCD1, and MARCH8.

In some embodiments, the first sample is a whole blood sample, a serum sample, or a plasma sample.

In some embodiments, the first sample is a plasma sample or a urine sample.

In some embodiments, the expression levels are determined by analyzing nucleic acids from the first sample.

In some embodiments, the expression levels are determined by analyzing RNA from the first sample.

In some embodiments, the expression levels are determined by RNA-sequencing.

In some embodiments, the methods described herein further comprise providing cell-free nucleic acids from the first sample or a second sample obtained from the transplant recipient, wherein the first sample or the second sample comprises transplant-derived cell-free nucleic acids and recipient-derived cell-free nucleic acids, sequencing a panel of single nucleotide polymorphisms (SNPs) from the cell-free nucleic acids, wherein the panel of SNPs is suitable for differentiating between transplant-derived cell-free nucleic acids and recipient-derived cell-free nucleic acids, and determining levels of transplant-derived cell-free nucleic acids.

In some embodiments, the expression levels of the one or more genes are normalized relative to the expression levels of one or more reference genes.

In some embodiments, the transplant is a solid organ transplant.

In some embodiments, the transplant is a kidney transplant, a heart transplant, a lung transplant, a pancreas transplant, a liver transplant, an intestinal transplant, a vascularized composite allograft transplant, or any combination thereof.

In some embodiments, the transplant is a cellular allograft.

In another aspect, provided herein is a kit for classifying immune quiescence or transplant rejection based on gene expression signature(s), the kit comprising in one or more separate containers a set of primers specific for at least three genes selected from the group consisting of DCAF12, FLT3, IL1R2, PDCD1, and MARCH8, reagents, controls, and instructions for use.

In some embodiments, the kit further comprises software instructions for statistical analysis of gene expression signatures.

In another aspect, provided herein is a method of discriminating between active rejection and immune quiescence in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a cut-off value indicates that the transplant recipient is likely experiencing active rejection or is at risk of developing active rejection, and the one or more gene expression score being below the cut-off value indicates that the transplant recipient is likely experiencing immune quiescence, and d) detecting active rejection if the one or more gene expression score is determined to be equal to or above the cut-off value.

In another aspect, provided herein is a method of discriminating between T cell-mediated rejection and antibody-mediated rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a first cut-off value indicates that the transplant recipient is likely experiencing T cell-mediated rejection or is at risk of developing T cell-mediated rejection, and the one or more gene expression score being equal to or above a second cut-off value indicates that the transplant recipient is likely experiencing antibody-mediated rejection or is at risk of developing antibody-mediated rejection, and d) detecting T cell-mediated rejection if the one or more gene expression score is determined to be equal to or above the first cut-off value, and detecting antibody-mediated rejection if the one or more gene expression score is determined to be equal to or above the second cut-off value.

In another aspect, provided herein is a method of discriminating between immune quiescence, T cell-mediated rejection, and antibody-mediated rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a first cut-off value indicates that the transplant recipient is likely experiencing T cell-mediated rejection or is at risk of developing T cell-mediated rejection, the one or more gene expression score being equal to or above a second cut-off value indicates that the transplant recipient is likely experiencing antibody-mediated rejection or is at risk of developing antibody-mediated rejection, and the one or more gene expression score being below the first and the second cut-off value indicates that the transplant recipient is likely experiencing immune quiescence, and d) detecting T cell-mediated rejection if the one or more gene expression score is determined to be equal to or above the first cut-off value, and detecting antibody-mediated rejection if the one or more gene expression score is determined to be equal to or above the second cut-off value.

In another aspect, provided herein is a method of detecting, monitoring, and/or guiding treatment of active rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, wherein the one or more gene expression score being equal to or above a cut-off value indicates that the transplant recipient is likely experiencing active rejection or is at risk of developing active rejection, c) detecting active rejection if the one or more gene expression score is determined to be equal to or above the cut-off value, and d) optionally treating the rejection by administering to the recipient an anti-rejection agent and/or increasing the dosage of an anti-rejection agent that the recipient already received.

In another aspect, provided herein is a method of detecting and distinguishing T cell-mediated rejection from antibody mediated rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely experiencing T cell-mediated rejection or is at risk of developing T cell-mediated rejection, d) detecting T cell mediated rejection if the one or more gene expression score is determined to be equal to or above the cut-off value, and e) optionally treating the rejection by administering to the recipient an anti-rejection agent and/or increasing the dosage of an anti-rejection agent that the recipient already received.

In another aspect, provided herein is a method of assessing the likelihood of allograft rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a cut-off value indicates that the transplant recipient is likely to experience allograft rejection or is at risk of developing allograft rejection, and d) predicting allograft rejection if the one or more gene expression score is determined to be equal to or above the cut-off value.

In another aspect, provided herein is a method of assessing the likelihood of antibody-mediated rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a cut-off value indicates that the transplant recipient is likely to experience antibody-mediated rejection or is at risk of developing antibody-mediated rejection, and d) predicting antibody-mediated rejection if the one or more gene expression score is determined to be equal to or above the cut-off value.

In another aspect, provided herein is a method of assessing the likelihood of T cell-mediated rejection in a transplant recipient, the method comprising a) providing polypeptides from a first sample obtained from the transplant recipient, b) determining expression levels of one or more polypeptides associated with an immune response-regulating pathway of inflammation, corticosteroid sensitivity, and/or T cell activation, c) applying a trained classifier to the expression levels of the one or more polypeptides to obtain one or more gene expression scores, wherein the one or more gene expression score being equal to or above a cut-off value indicates that the transplant recipient is likely to experience T cell-mediated rejection or is at risk of developing T cell-mediated rejection, and d) predicting T cell-mediated rejection if the one or more gene expression score is determined to be equal to or above the cut-off value.

In another aspect, provided herein is a method of discriminating between T cell-mediated rejection and antibody-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) generating a gene expression score by applying a trained classifier to the expression levels of the one or more genes, wherein the gene expression score being equal to or above a first cut-off value indicates that the transplant recipient is likely experiencing T cell-mediated rejection or is at risk of developing T cell-mediated rejection, and wherein the gene expression score being equal to or above a second cut-off value indicates that the transplant recipient is likely experiencing antibody-mediated rejection or is at risk of developing antibody-mediated rejection, and d) detecting T cell-mediated rejection if the gene expression score is determined to be equal to or above the first cut-off value, and detecting antibody-mediated rejection if the gene expression score is determined to be equal to or above the second cut-off value.

In another aspect, provided herein is a method of discriminating between immune quiescence, T cell-mediated rejection, and antibody-mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) generating a gene expression score by applying a trained classifier to the expression levels of the one or more genes, wherein the one or more gene expression score being equal to or above a first cut-off value indicates that the transplant recipient is likely experiencing T cell-mediated rejection or is at risk of developing T cell-mediated rejection, wherein the gene expression score being equal to or above a second cut-off value indicates that the transplant recipient is likely experiencing antibody-mediated rejection or is at risk of developing antibody-mediated rejection, and wherein the one or more gene expression score being below the first and the second cut-off value indicates that the transplant recipient is likely experiencing immune quiescence, and d) detecting T cell-mediated rejection if the gene expression score is determined to be equal to or above the first cut-off value, and detecting antibody-mediated rejection if gene expression score is determined to be equal to or above the second cut-off value.

In another aspect, provided herein is a method of detecting and distinguishing T cell-mediated rejection from antibody mediated rejection in a transplant recipient, the method comprising a) providing nucleic acids from a first sample obtained from the transplant recipient, b) determining expression levels of one or more genes associated with an immune response-regulating pathway of inflammation, corticosteroid sensitivity, and/or T cell activation, c) applying a trained classifier to the expression levels of the one or more genes to obtain one or more gene expression scores, wherein the one or more gene expression score being equal to or above a cut-off value indicates that the transplant recipient is likely experiencing T cell-mediated rejection or is at risk of developing T cell-mediated rejection, d) detecting T cell mediated rejection if the one or more gene expression score is determined to be equal to or above the cut-off value, and e) optionally treating the rejection by administering to the recipient an anti-rejection agent and/or increasing the dosage of an anti-rejection agent that the recipient already received.

DESCRIPTION OF THE FIGURES

The embodiments and figures disclosed herein are only intended to be illustrative, not limiting in scope

FIG. 2A shows a box and whisker plot of the application of the 5-gene expression signature to samples from healthy, stable (HS) transplant recipients, whose healthy transplant status was confirmed with transplant-derived cell-free DNA levels below the threshold value of 1% using AlloSure® ("HS w. AS<1%"; left) vs. renal transplant recipients experiencing allograft rejection (right); the y-axis shows the gene expression scores. The box and whisker plot shows median and interquartile range (IQR). FIG. 2B shows a receiver operating characteristic (ROC) plot for the training set comparing the transplant status of healthy, stable (HS) transplant recipients to the transplant status of renal transplant recipients who experienced allograft rejection (TCMR, ABMR, or mixed TCMR/ABMR rejection).

FIG. 3A shows box and whisker plots illustrating that, on the basis of a trained classifier, biopsy-defined rejections (R, n=18) were significantly distinguished from quiescence (Q, n=98); the y-axis shows the gene expression scores. FIG. 3B shows box and whisker plots illustrating that, on the basis of a trained classifier, there was no statistically significant difference among quiescence subgroups, including healthy, stable kidney transplant recipients who had no clinical or laboratory indicators of concern regarding the allograft and therefore no clinically indicated biopsy (HS, n=22), kidney transplant recipients with protocol biopsy-defined non-rejection (pNR, n=29), and kidney transplant recipients with clinically indicated biopsy who did not experience a rejection (NR, n=47). The power of the classifier to differentiate the various non-rejecting cohorts from the rejecting cohorts is evidenced by the fact that all three non-rejecting cohorts had significantly lower gene expression scores than the rejecting cohorts, namely TCMR (n=7), ABMR (n=10), and TCMR/ABMR mixed rejection (n=1); the y-axis shows the gene expression scores. FIG. 3C shows TCMR results stratified by grade, suggesting a trend for gene expression scores and TCMR grades. The x-axis shows the TCMR grade, from left to right along the x-axis, encompassing IA, IB, and IIA, and the y-axis shows the corresponding gene expression scores. FIG. 3D shows an ROC plot for the primary validation set comparing the transplant status of renal transplant recipients who experienced allograft rejection to the transplant status of non-rejecting renal transplant recipients. A second plotted line compares rejection to quiescence. All statistical analyses were unpaired Student's t-tests.

FIG. 4A shows box and whisker plots illustrating that, on the basis of a trained classifier, biopsy-defined rejection (n=11) was statistically significantly different from biopsy-defined no-rejection (NR, n=8); the y-axis shows the gene expression scores. FIG. 4B shows box and whisker plots illustrating that, on the basis of a trained classifier, all rejection groups have elevated scores relative to NR (n=8 NR, 7 TCMR, 2 ABMR, 2 mixed TCMR/ABMR). FIG. 4C shows an ROC plot for the second independent validation set comparing the transplant status of non-rejecting renal transplant recipients to the transplant status of renal transplant recipients who experienced allograft rejection (TCMR, ABMR, and mixed TCMR/ABMR). All statistical analyses were unpaired Student's t-tests.

FIG. 5A shows box and whisker plots comparing the gene expression scores (5-gene expression signature) for no-rejection (NR, n=106) versus rejection (n=29) for the full combined datasets. FIG. 5B shows box and whisker plots comparing the gene expression scores (5-gene expression signature) for no-rejection (NR) versus the scores of each type of rejection (n=55 NR, 14 TCMR, 12 ABMR, 3 mixed TCMR/ABMR). FIG. 5C shows an ROC plot for the combined validation sets with rejection compared to immune quiescence (AUC=0.779), and rejection compared to no-rejection (AUC=0.776). All statistical analyses were unpaired Student's t-tests.

FIG. 6A shows the sensitivity (circles) and specificity (triangles) for discriminating non-rejection and rejection. The x-axis shows the gene expression scores, and the y-axis shows the sensitivity and specificity in percent. FIG. 6B shows the sensitivity (circles) and specificity (triangles) for discriminating immune quiescence and rejection. The x-axis shows the gene expression scores, and the y-axis shows the sensitivity and specificity in percent. FIG. 6C shows the negative predictive value (NPV) for discriminating non-rejection and rejection at 25% prevalence of rejection (solid symbols) and 10% prevalence of rejection (open symbols). The x-axis shows the gene expression scores, and the y-axis shows the NPV. FIG. 6D shows the NPV for discriminating immune quiescence and rejection at 25% prevalence of rejection (solid symbols) and 10% prevalence of rejection (open symbols). The x-axis shows the gene expression scores, and the y-axis shows the NPV. FIG. 6E shows the positive predictive value (PPV) for discriminating non-rejection and rejection at 25% prevalence of rejection (solid symbols) and 10% prevalence of rejection (open symbols). The x-axis shows the gene expression scores, and the y-axis shows the PPV. FIG. 6F shows the PPV for discriminating immune quiescence and rejection at 25% prevalence of rejection (solid symbols) and 10% prevalence of rejection (open symbols). The x-axis shows the gene expression scores, and the y-axis shows the PPV.

FIG. 7A shows a scatterplot of all quiescence-indicating combined scores and rejection-indicating combined scores from the primary validation set, based on the combined analysis of the 5-gene expression signature (y-axis) and transplant-derived cell-free DNA levels, as measured by AlloSure® (x-axis). Circles indicate all types of quiescence or no rejection (NR, HS, pNR); triangles indicate TCMR; squares indicate ABMR. FIG. 7B shows ROC plots of a linear combination of gene expression scores and transplant-derived cell-free DNA levels as described in FIG. 7A. The combined scores have an AUC of 0.894, the gene expression scores alone have an AUC of 0.768, and the transplant-derived cell-free DNA levels alone have an AUC of 0.85.

FIG. 10A illustrates molecular tag (MT) counts for transcripts of the five informative genes of the 5-gene expression signature (MT counts of 0, indicated by line) and External RNA Controls Consortium (ERCC) transcripts for ERCC Mix 1. FIG. 10B illustrates molecular tag (MT) counts for transcripts of the five informative genes of the 5-gene expression signature (MT counts of 0, indicated by line) and External RNA Controls Consortium (ERCC) transcripts for ERCC Mix 2.

FIG. 12A shows total molecular tag (MT) counts for the informative genes and the reference genes across RNA input amounts. The black line indicates the best fitted line from the linear regression model ($R^2$=0.999), and the grey zone indicates 95% confidence level interval from the model. FIG. 12B illustrates that the gene expression scores remained consistent and did not show any significant difference across various RNA input amounts (p-value=0.3084).

FIGS. 14A-14B provide exemplary performance characteristics of the 5-gene expression signature across the range of gene expression scores (GEP scores) in all three validation cohorts (n=235, 66 rejections, 169 non-rejection or quiescence) for discriminating rejection from non-rejection, or quiescence, in accordance to embodiments of the disclosure. FIG. 14A lists exemplary performance characteristics for the sensitivity, specificity, positive predictive value at 10% prevalence of rejection (PPV 10), negative predictive value at 10% prevalence of rejection (NPV 10), positive predictive value at 25% prevalence of rejection (PPV 25), and negative predictive value at 25% prevalence of rejection (NPV 25). NC means not computable. FIG. 14B illustrates exemplary performance characteristics for the sensitivity, specificity, negative predictive value at 10% prevalence of rejection (NPV 10), and negative predictive value at 25% prevalence of rejection (NPV 25).

FIGS. 17A-17C shows exemplary probability plots for all three validation cohorts, in accordance with embodiments of the disclosure, for differentiating the transplant status of renal transplant recipients who experienced allograft rejection from the transplant status of non-rejecting renal transplant recipients based on the combined analysis of the 5-gene expression signature (y-axis) and transplant-derived cell-free DNA levels, as measured by AlloSure® (x-axis). The probability plots illustrate the relationship of gene expression scores and transplant-derived cell-free DNA levels or amounts without the use of combined scores. FIG. 17A illustrates an exemplary probability plot to distinguish non-rejection or quiescence from overall rejection. FIG. 17B illustrates an exemplary probability plot to distinguish non-rejection or quiescence from TCMR. FIG. 17C illustrates an exemplary probability plot to distinguish non-rejection or quiescence from ABMR. The gray shades are a scale (explanatory key is shown in the figure) from high probability of immune quiescence and low probability of graft injury (gray shade on the far left of scale) to low probability of immune quiescence and high probability of graft injury (gray shade on the far right of scale).

DETAILED DESCRIPTION OF EMBODIMENTS

Figure 1:
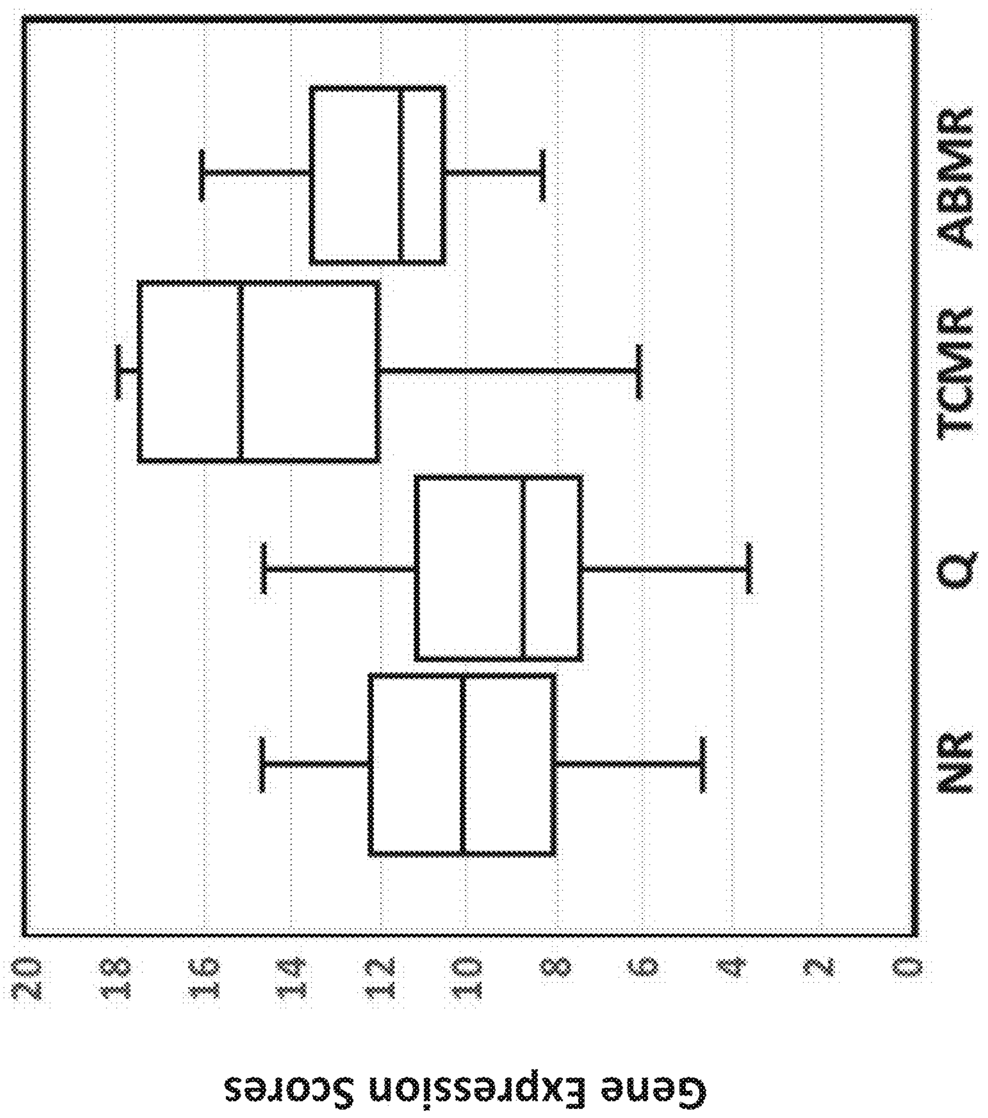
FIG. 1 shows exemplary 5-gene expression scores for control groups (NR: renal transplant recipients with clinically indicated biopsy who did not experience a rejection, and pNR: renal transplant recipients with protocol biopsy-defined non-rejection, pNR is shown as Q) and allograft rejection groups (T cell-mediated rejection, "TCMR" and antibody-mediated rejection, "ABMR") in renal transplant recipients, in accordance to embodiments of the disclosure.

The present disclosure is based on the discovery that gene expression signatures of selected informative genes are useful for identifying and discriminating transplant recipients, who show signs of elevated immune activity as a possible indicator of allograft rejection, from transplant recipients who do not show signs of elevated immune activity, i.e. who are in a state of immune quiescence. The present disclosure is furthermore based on the discovery that gene expression signatures of selected informative genes are useful for identifying transplant recipients who are experiencing immune quiescence, or who are experiencing or are at risk of experiencing allograft rejection, and for discriminating between recipients who are experiencing or are at risk of experiencing T cell-mediated allograft rejection, antibody-mediated allograft rejection, or a mixed T cell/antibody-mediated allograft rejection. The present disclosure is furthermore based on the discovery that gene expression signatures of selected informative genes combined with transplant donor-derived cell-free DNA levels, all obtained from one or more samples from the same transplant recipient, are useful to discriminate allograft rejection from immune quiescence and, further, to discriminate antibody-mediated rejection from T cell-mediated rejection or mixed rejection.

The present disclosure is directed to methods and kits for detecting and monitoring immune quiescence, detecting and monitoring a transplant recipient's response to therapeutic intervention, detecting and monitoring a transplant recipient's medication adherence or compliance, differentiating immune quiescence from allograft rejection, and detecting, monitoring, and guiding treatment of allograft rejection in transplant recipients using one or more gene expression signatures, alone or in combination with transplant donor-derived cell-free DNA levels, to discriminate immune quiescence from allograft rejection and, further, to discriminate immune quiescence from antibody-mediated rejection, T cell-mediated rejection or mixed rejection. It is presented to enable a person of ordinary skill in the art to make and use the various embodiments described herein.

In practicing the present embodiments, the expression of selected informative genes is analyzed in one or more samples from a transplant recipient, optionally normalized against endogenous reference gene expression, and evaluated using biostatistical methods to assess the degree of immune activity in the transplant recipient, where immune quiescence indicates the absence or low levels of immune activity or associated clinical symptoms. The assessment of the degree of immune activity, alone or in combination with an assessment of allograft injury based on transplant donor-derived cell-free DNA levels, is useful for determining the health status of the allograft, the risk of transplant rejection, the occurrence of actual transplant rejection, the need for potential adjustment of the transplant recipient's immunosuppressive treatment, and, ultimately, for discriminating immune quiescence from allograft rejection and, further, for discriminating immune quiescence from antibody-mediated rejection, T cell-mediated rejection or mixed rejection. These methods of detecting and distinguishing immune quiescence from allograft rejection, and guiding treatment of a transplant recipient may be repeated for a longitudinal assessment and monitoring of the treatment success of the transplant recipient.

All references cited herein, including patent applications, patents, and publications, are hereby incorporated by reference in their entirety.

Before describing the present embodiments in detail, it will be useful to set forth definitions whose terminology serves the purpose of illustrating particular embodiments and is not intended to be limiting in scope.

DEFINITIONS

Unless defined otherwise, all scientific and technical terms are understood to have the same meaning as commonly used in the art to which they pertain. Singleton et al., Dictionary of DNA and Genome Technology 3rd ed., Wiley-Blackwell 2012, and Baxevanis, Bader, and Wishart, Bioinformatics: A Practical Guide to the Analysis of Genes and Proteins 4th ed., John Wiley & Sons 2020, provide one skilled in the art with a general guide to many of the terms used in the present application.

As used in the specification and in the appended claims, the singular forms of "a," "an," and "the" include plural referents unless the context clearly dictates otherwise. All methods described herein can be performed in any suitable order unless otherwise indicated herein or otherwise clearly contradicted by context. The use of any and all examples, or exemplary language (e.g. "such as") provided with respect to certain embodiments herein is intended merely to illustrate the embodiments, and does not pose a limitation on the scope of the embodiments otherwise claimed. No language in the specification should be construed as indicating any non-claimed element essential to the practice of the embodiments.

The term "sample," as used herein, refers to any sample obtained from a transplant recipient, such as whole blood, plasma, serum, lymph, peripheral blood mononuclear cells, buccal swabs, saliva, urine or tissue from a biopsy.

The term "solid organ transplant," as used herein, refers to any allogeneic transplant, i.e. an allograft, of a solid organ including, but not limited to, a kidney transplant, a heart transplant, a lung transplant, a liver transplant, a pancreas transplant, a vascularized composite allograft transplant, or combinations of the above transplants.

The term "hollow organ transplant," as used herein, refers to any transplant of a hollow organ including, but not limited to, an intestinal transplant.

The term "transplant" includes both allogeneic "solid organ transplants" and cellular transplants such as, for example, a bone marrow transplant, pancreatic islet cells, stem cells, skin tissue, skin cells, or a xenotransplant. The term "transplant" includes also cellular transplants of autologous origin, e.g., a transplant comprising autologous cells that originate from the recipient and that were genetically engineered before re-administration into the recipient. The terms "transplant" and "allograft" are used interchangeably herein.

The term "gene cluster" or "cluster," as used herein, refers to a group of two or more genes with a related gene expression pattern, e.g., gene expression levels that have a level or degree of correlation or association.

The term "TCMR," as used herein, refers to cellular or T cell mediated (allograft) rejection including, but not limited to, TCMR IA, IB, IIA, IIB, borderline TCMR and chronic TCMR. The term also includes acute cellular rejection (ACR).

The term "ABMR," as used herein, refers to antibody-mediated (allograft) rejection including, but not limited to, acute active antibody-mediated rejection, chronic active antibody-mediated rejection, and chronic stable antibody-mediated rejection. The term may also be abbreviated as "AMR."

The term "immune quiescence," as used herein, refers to a state that is characterized by an absence or low levels of immune activity or absence of rejection-associated clinical symptoms such as biopsy-confirmed rejection, or significant changes in organ function, e.g., as indicated by elevated serum creatinine levels, decreased estimated glomerular filtration rate, abnormal echocardiogram results or some other clinical concern that indicates a clinical need for a biopsy. The term "immune quiescence,' as used herein, also refers to a state that may be characterized by the absence of conditions, other than transplant rejection, that may cause an elevation of immune activity. Such conditions may include, but are not limited to, systemic infections with viruses, bacteria, fungi, and parasites, which a transplant recipient might have contracted during the process of transplantation or following transplantation, or immune disorders that are characterized by dysregulations of the immune system due to autoimmunity causing the immune system to attack the body's own cells, tissues and/or organs, or due to chronic inflammation and chronic activation of inflammatory cells damaging the body's own cells, tissues and/or organs. Such immune disorders include, but are not limited to, autoimmune diseases, e.g., Autoimmune Hepatitis, Multiple Sclerosis, Myasthenia Gravis, Type 1 Diabetes, Psoriasis, Hashimoto's Thyroiditis, Grave's Disease, Ankylosing Spondylitis Sjogrens Disease, Crest Syndrome, Scleroderma; chronic inflammatory diseases, e.g., Atherosclerosis, Congestive Heart Failure, Crohn's Disease, Ulcerative Colitis, Polyarteritis Nodosa, Whipple's Disease, Primary Sclerosing Cholangitis; and autoimmune/chronic inflammatory diseases, e.g., Systemic Lupus Erythematosis, Rheumatoid Arthritis.

The term "nucleic acid," as used herein, refers to RNA or DNA that is linear or branched, single or double stranded, or a hybrid thereof. The term also encompasses RNA/DNA hybrids.

The term "gene," as used herein, refers to a nucleic acid, e.g., DNA or RNA, sequence that comprises coding sequences necessary for the production of RNA or a polypeptide. A polypeptide can be encoded by a full-length coding sequence or by any part thereof.

The terms "coding" or "encoding," as used herein, refer to the process by which a gene, through the mechanisms of transcription and translation, provides information to a cell from which a series of amino acids can be assembled into a specific amino acid sequence to produce an active polypeptide or protein. The transcription of a subset of genes into mRNA regulates the biological activities within a cell. Information about changes in the extent of production of a transcriptional (or translational) product of a gene provides important insights into understanding abnormal developments and diseases that affect the cell.

The term "gene expression," as used herein, refers to the production of a transcriptional or translational product of a gene, e.g., total RNA, mRNA, a splice variant mRNA, or polypeptide. Unless otherwise apparent from the context, gene expression levels can be measured at the RNA and/or polypeptide level. The measurement of gene expression, including differential gene expression, provides one or more gene expression signatures or gene expression profiles (GEP), that are quantified using gene expression scores or gene expression signature scores. Such gene expression signatures or profiles, and their respective quantitative scores, may provide an indication of rejection, characterized by elevated activity of cells of the immune system, or an indication of immune quiescence, characterized by a resting state of cells of the immune system demonstrating absence or low levels of immune activity. The terms "gene expression signature" and "gene expression profile" are used interchangeably herein. The terms "gene expression score" and "gene expression signature score" are used interchangeably herein.

The term "differential gene expression," as used herein, refers to the production of a transcriptional or translational product of a gene, e.g., mRNA or protein, at statistically significantly higher or lower, or detectable versus undetectable, gene expression levels in two or more groups of samples. Such samples may have been obtained from the same transplant recipient at different time points or from different transplant recipients.

The terms "discriminate" and "discriminating," as used herein, refer to identifying a statistically significant difference in gene expression or probability of certain conditions such as immune quiescence or rejection in transplant recipients.

The term "cut-off value," as used herein, refers to a score or signature score that is used to divide the results into categories with a certain probability of transplant rejection, T cell-mediated rejection, antibody-mediated rejection, mixed antibody-mediated/T cell-mediated rejection, non-rejection, or immune quiescence. A cut-off value may be chosen based on the diagnostic performance of the test or gene expression signature as well as desired performance parameters. The terms "score" and "signature score" are used interchangeably herein.

The term "machine-readable medium," as used herein, refers to both a single medium and multiple media (e.g., a centralized or distributed database and/or associated caches and servers) that store one or more sets of instructions, and includes any medium that is capable of storing, encoding, or carrying a set of instructions for execution by a device and that causes a device to perform any method disclosed herein and more. The term "machine-readable medium," as used herein, includes but is not be limited to solid-state memories, optical and magnetic media, and carrier wave signals.

Overview

The present disclosure relates to methods of detecting and monitoring immune quiescence, detecting and monitoring a transplant recipient's response to therapeutic intervention, detecting and monitoring a transplant recipient's medication adherence or compliance, discriminating between immune quiescence and active rejection in a transplant recipient, discriminating between immune quiescence and T cell-mediated rejection, discriminating between immune quiescence and antibody-mediated rejection in a transplant recipient, discriminating between immune quiescence, T cell-mediated rejection, and antibody-mediated rejection in a transplant recipient, detecting, monitoring, and/or guiding treatment of active rejection in a transplant recipient, detecting and distinguishing T cell-mediated rejection from antibody mediated rejection in a transplant recipient, assessing the risk or likelihood of antibody-mediated rejection (ABMR) in a transplant recipient, assessing the risk or likelihood of T cell-mediated rejection (TCMR) in a transplant recipient, and/or assessing the risk of likelihood of mixed TCMR/ABMR.

The present disclosure is based, at least in part, on Applicant's development of differential gene expression signatures or profiles, based on one or more trained classifiers, that are considered useful in assessing the health status of solid organ transplants, such as heart, kidney, liver, or lung transplants, as well as cellular transplants in a transplant recipient. Upon transplantation and during the time thereafter, and before or after initiation of immunosuppressive drug therapy, the transplant recipient may be at risk of transplant rejection or experience actual transplant rejection by way of T cell-mediated rejection (TCMR), antibody-mediated rejection (ABMR), or mixed TCMR/ABMR rejection. Alternatively, the recipient may experience immune quiescence, which may be characterized by an absence or low levels of immune activity, absence of rejection-associated clinical symptoms, or absence of conditions, other than transplant rejection, that may cause an elevation of immune activity, e.g., systemic infection, autoimmune and/or chronic inflammatory diseases.

Identifying and distinguishing transplant recipients who experience immune quiescence from transplant recipients who are at risk of rejection or who experience active TCMR, ABMR or mixed TCMR/ABMR rejection would be valuable and informative with regard to a clinical decision by the treating physician or health care provider involving the need for (a) performing a transplant biopsy, and/or (b) initiating, modifying, or adjusting immunosuppressive drug therapy. If a transplant recipient is found to experience immune quiescence, based on a differential gene expression signature alone or in combination with levels of transplant-derived cell-free nucleic acids, a biopsy may not be needed, thereby sparing the recipient an invasive, risky and often inconclusive procedure. Likewise, if a transplant recipient is found to experience immune quiescence, based on a differential gene expression signature, alone or in combination with levels of transplant-derived cell-free nucleic acids, immunosuppressive drug therapy may be modified, adjusted, delayed, or not initiated at all to address the decreased or absent need for immunosuppression due to the transplant recipient's absence or low levels of immune activity or absence of rejection-associated clinical symptoms. Furthermore, if a transplant recipient is found to experience immune quiescence, based on a differential gene expression signature alone or in combination with levels of transplant-derived cell-free nucleic acids, it can be concluded that the transplant recipient adheres to the prescribed immunosuppressive drug therapy or regimen.

Furthermore, if a transplant recipient is found to experience immune quiescence, based on a differential gene expression signature alone or in combination with levels of transplant-derived cell-free nucleic acids, this may indicate an absence of infection. Infection with infectious agents such as viruses, bacteria, fungi, and parasites can occur during the process of transplantation or following transplantation, particularly since transplant recipients may be immunocompromised due to immunosuppressive induction and/or maintenance therapy. Likewise, if a transplant recipient is found not to experience immune quiescence, based on a differential gene expression signature alone or in combination with levels of transplant-derived cell-free nucleic acids, a test for one or more infectious agents in a sample from the transplant recipient may be warranted. Infectious agents whose presence or levels may be tested for may include, but are not limited to, viruses such as Cytomegalovirus, Epstein-Barr virus, Anelloviridae, and BK virus; bacteria such as *Pseudomonas aeruginosa*, Enterobacteriaceae, *Nocardia, Streptococcus pneumonia, Staphyloccous aureus*, and *Legionella*; fungi such as *Candida, Aspergillus, Cryptococcus, Pneumocystis carinii*; or parasites such as *Toxoplasma gondii*.

In some embodiments, the presence or levels of viral infectious agents in the transplant recipient may be tested upon finding that a transplant recipient does not experience immune quiescence, based on a differential gene expression signature alone or in combination with levels of transplant-derived cell-free nucleic acids. Viral markers may be analyzed in nucleic acids obtained from a sample from the transplant recipient to determine the presence or levels of viruses in the transplant recipient. Viruses which may be tested for include, for example, Cytomegalovirus, Epstein-Barr virus, Anelloviridae, and BK virus. The results of the tests for presence or levels of viruses may be used to classify the immune status of the transplant recipient and to determine the status of infection in the transplant recipient.

If a transplant recipient is found to be at risk of transplant rejection or to experience active rejection, based on a differential gene expression signature alone or in combination with levels of transplant-derived cell-free nucleic acids, a confirmatory biopsy may be ordered ahead of schedule, and/or immunosuppressive drug therapy may be initiated, modified, or adjusted to address the increased or present need for immunosuppression. As described in the Examples, Applicant has identified differential gene expression signatures that, alone or in combination with levels of transplant-derived cell-free nucleic acids, are informative with respect to whether a transplant recipient is experiencing rejection or is at risk of rejection, or experiences immune quiescence. Furthermore, the differential gene expression signatures of the informative genes, alone or in combination with levels of transplant-derived cell-free nucleic acids, may be informative with respect to whether a transplant recipient is experiencing T cell-mediated rejection (TCMR), antibody-mediated rejection (ABMR), or mixed TCMR/ABMR rejection. Furthermore, the differential gene expression signatures of the informative genes, alone or in combination with levels of transplant-derived cell-free nucleic acids, may be informative with respect to whether a transplant recipient is adhering to the prescribed immunosuppressive drug therapy.

Informative Genes or Genes of Interest

The methods described herein involve determining expression levels of one or more informative genes. In general, expression levels of one or more genes associated with an immune response-regulating pathway of inflammation, corticosteroid sensitivity, and/or T cell activation are informative with respect to the status of immune activity in a transplant recipient, and, thus, to the status, e.g., the health status, of a transplant in a recipient. For example, in some embodiments such genes are informative with respect to whether the transplant recipient is experiencing immune quiescence or active rejection (e.g., T cell-mediated rejection, antibody-mediated rejection, or mixed T cell-mediated rejection/antibody-mediated rejection). Experiencing immune quiescence can be considered as experiencing a continuance of a resting state of the cells of the immune system and/or absence of immune activation or elevated immune activity, as indicated by the absence of a change, increase or decrease of expression of the one or more genes of interest in comparison to reference genes. In contrast, experiencing active rejection can be considered as experiencing a disruption of the resting state of the cells of the immune system and/or the presence of immune activation or elevated immune activity, as indicated by a change, increase or decrease of expression of the one or more genes of interest in comparison to reference genes. Signs of elevated immune activity or immune activation may indicate the development or presence of an allograft rejection or the risk thereof, or a state of immune activation that is caused by conditions, other than transplant rejection, that may cause an elevation of immune activity, e.g., autoimmune and/or chronic inflammatory diseases, systemic infection. Experiencing immune quiescence can also be considered as experiencing a continuance of a suppressed state of the cells of the immune system and/or absence of immune activity, as indicated by the absence of a change, increase or decrease of expression of the one or more genes of interest in comparison to reference genes. In contrast, experiencing active rejection can also be considered as experiencing a disruption of the suppressed state of the cells of the immune system and/or the presence of immune activation or elevated immune activity, as indicated by a change, increase or decrease of expression of the one or more genes of interest in comparison to reference genes. Signs of elevated immune activity or immune activation may indicate the development or presence of an allograft rejection or the risk thereof, or a state of immune activation that is caused by conditions, other than transplant rejection, that may cause an elevation of immune activity, e.g., autoimmune and/or chronic inflammatory diseases, systemic infection.

In some embodiments, the methods described herein involve applying a trained classifier to the expression levels of the one or more informative genes, as is described in detail herein. In some embodiments, the methods described herein involve generating a gene expression score by applying a trained classifier to the expression levels of the one or more genes. The same one or more informative genes may be used for each transplant recipient; there is no need to customize the one or more informative genes to different recipients of transplants.

Exemplary informative genes, as listed in Table 1, below, are related to immune response-regulating pathways, particularly to the immune response-regulating pathways of inflammation, corticosteroid sensitivity, and T cell activation. Five exemplary informative genes are described in detail in Table 1.

TABLE 1

List of Exemplary Informative Genes

| Gene Symbol | Name | Gene ID* | Cytogenetic Location* |
|---|---|---|---|
| FLT3<br>Also known as: FLK2; STK1; CD135; FLK-2. | FMS related receptor tyrosine kinase 3 | 2322 | 13q12.2 |
| IL1R2<br>Also known as: IL1RB; CD121b; IL1R2c; CDw121b; IL-1RT2; IL-1RT-2 | Interleukin 1 receptor type 2 | 7850 | 2q11.2 |
| MARCH8<br>Also known as: MIR; CMIR; | Membrane associated ring- | 220972 | 10q11.21-q11.22 |

TABLE 1-continued

List of Exemplary Informative Genes

| Gene Symbol | Name | Gene ID* | Cytogenetic Location* |
|---|---|---|---|
| c-MIR; MARCH8; RNF178; MARCH-VIII | CH-type finger 8 | | |
| PDCD1 Also known as: PD1; CD279; SLEB2; hPD-1; hPD-1; hSLE1 | Programmed cell death 1 | 5133 | 2q37.3 |
| DCAF12 Also known as: CT102; TCC52; DDB1 and CUL4 associated factor 12; KIAA1892; WDR40A | WD repeat domain 40A | 25853 | 9p13.3 |

*according to the National Center For Biotechnology Information (NCBI)

Four of the five exemplary informative genes belong to gene clusters. DCAF12 and MARCH8, for example, are related to the immune response-regulating pathway of inflammation and correlate with each other by a factor of 0.88. FLT3 and IL1R2 are related to the immune response-regulating pathway of corticosteroid sensitivity and correlate with each other by a factor of 0.67. PDCD1 is related to the immune response-regulating pathway of T cell activation.

In various embodiments, two or more genes are determined to be in a correlating gene cluster when they exhibit similar expression pattern across a set of samples from transplant recipients with and without rejection. In some embodiments, two genes are determined to be correlated when their expression levels are increased or decreased to a similar extent in the same samples. Exemplary methods for clustering based on gene expression patterns are described, for example, in Oyelade, J. et al., *Bioinform Biol Insights.* 2016; 10: 237-253. In some embodiments, clustering is based on genes, samples, and/or other variables, and is performed using a method such as hierarchical clustering (HC), self-organizing maps (SOM), and/or K-means clustering.

In some embodiments, the one or more genes associated with an immune response-regulating pathway, particularly with an immune response-regulating pathway of inflammation, corticosteroid sensitivity, and/or T cell activation, comprises 3, 4 or 5 genes. In some embodiments, the one or more genes associated with an immune response-regulating pathway, particularly with an immune response-regulating pathway of inflammation, corticosteroid sensitivity, and/or T cell activation, comprises MARCH8, PDCD1, and DCAF12; FLT3, PDCD1, and DCAF12; FLT3, IL1R2, and DCAF12; IL1R2, MARCH8, and PDCD1; FLT3, MARCH8, and PDCD1; IL1R2, PDCD1, and DCAF12; FLT3, IL1R2, and MARCH8; FLT3, IL1R2, and PDCD1; IL1R2, MARCH8, PDCD1, and DCAF12; FLT3, MARCH8, PDCD1, and DCAF12; FLT3, IL1R2, PDCD1, and DCAF12; FLT3, IL1R2, MARCH8, and DCAF12; or FLT3, IL1R2, MARCH8, and PDCD1. Exemplary methods involving 3- or 4-gene signatures are described in Example 3, below. In some embodiments, the one or more genes associated with an immune response-regulating pathway, particularly with an immune response-regulating pathway of inflammation, corticosteroid sensitivity, and/or T cell activation, comprises a combination of 3 or 4 genes as shown in Table 2 or Table 3, below.

In some embodiments, the one or more genes associated with an immune response-regulating pathway, particularly with an immune response-regulating pathway of inflammation, corticosteroid sensitivity, and/or T cell activation, comprises DCAF12, FLT3, IL1R2, PDCD1, and MARCH8.

Transplants

The methods of the present disclosure involve providing nucleic acids from a sample obtained from a subject who is the recipient of a transplant.

The transplant may be allogeneic, quasi allogeneic or xenogeneic. In some cases, the transplant is derived from a human, mammal, non-human mammal, ape, orangutan, monkey, chimpanzee, cow, pig, horse, rodent, bird, reptile, or other animal. The transplant may be any solid organ, hollow organ, bone marrow, skin transplant, tissues, or cells.

In some embodiments, the transplant is derived from an adult. The transplant tissue, organ, or cells may also be derived from a fetus, embryo, embryonic stem cells, induced pluripotent stem cells, child, or teenager. The donor tissue may be from a male or a female.

The transplant organ, tissue, or cells may be derived from a subject who has certain similarities or compatibilities with the recipient subject. For example, the transplant organ, tissue, or cells may be derived from a donor subject who is age-matched, ethnicity-matched, gender-matched, blood-type compatible, or HLA-type compatible with the recipient subject.

Organ Transplants

The transplant tissue can be whole organs, or portions of organs. Examples of organ transplants whose health status can be determined by the methods and kits described herein include, but are not limited to, kidney transplant, pancreas transplant, liver transplant, heart transplant, lung transplant, intestine transplant, bladder transplant, pancreas after kidney transplant, simultaneous pancreas-kidney transplant, blood transfusion, bone marrow transplantation, or combinations thereof. The organ transplant may also be part of reconstructive surgery, such as a cartilage or tendon transplant. Examples of donor organs (or portions of organs) include, but are not limited to, adrenal gland, appendix, bladder, brain, ear, esophagus, eye, gall bladder, heart, kidney, large intestine, liver, lung, mouth, muscle, nose, pancreas, parathyroid gland, pineal gland, pituitary gland, skin, small intestine, spleen, stomach, thymus, thyroid gland, trachea, uterus, vermiform appendix, cornea, skin, heart valve, artery, or vein. In some cases, the organ is a gland organ. For example, the organ may be an organ of the digestive or endocrine system; in some cases, the organ can be both an endocrine gland and a digestive organ. In some cases, the organ may be derived from endoderm, ectoderm, primitive endoderm, or mesoderm. In some embodiments, the transplant is a vascularized composite allograft transplant.

In some embodiments, the organ, tissue or cell transplant is an intact organ, a fragment of an intact organ, a disrupted organ, or a cell from any of the organs disclosed herein. Donor cells may be derived from any of the donor organs disclosed herein (e.g., pancreatic cell, hepatic cell, glioma, etc). The transplanted tissue may also comprise stem cells (e.g., multipotent stem cells, pluripotent stem cells, neuronal stem cells, heart stem cells, induced pluripotent stem cells, embryonic stem cells, cells derived from cord blood, etc.). In some cases, the transplant organ, tissues or cells may comprise cholecystocytes, cardiomyocytes, valve cells, glomerulus cells (e.g., parietal, podocyte), kidney proximal tubule brush border cells, Loop of Henle thin segment cells, thick ascending limb cells, kidney distal tubule cells, kidney collecting ductal cells, or interstitial kidney cells, enterocytes, goblet cells, enterocytes, caveolated tuft cells, enteroendocrine cells, ganglion neurons, parenchymal cells, non-parenchymal cells, hepatocytes, sinusoidal endothelial cells, kupffer cells, hepatic stellate cells, tendon, cartilage, bone, blood, lymph, myocytes, muscle fibers, pancreatic beta cells, endothelial cells, or exocrine cells.

In some embodiments, the transplant is a kidney transplant. A kidney transplant may also be referred to as a renal transplant. In some embodiments, the kidney transplant is derived from a deceased donor or a living donor. In some embodiments, the kidney transplant is derived from an unrelated or related donor. In some embodiments, a kidney is transplanted together with a pancreas, or before or after a pancreas transplant.

Cellular Allografts

In some embodiments, the transplant is a cellular allograft, e.g., a transplant comprising allogeneic cells that originate from a donor. These include, but are not limited to, cells taken directly from a donor for administration into a recipient, cells taken from a donor and genetically engineered before administration into a recipient, cells taken from a donor and cultured before administration into a recipient, cells taken from a donor and subjected to a manufacturing process before administration into a recipient, and any combination thereof. Cells may also be stored before administration into a recipient (i.e., "off-the-shelf" cells).

The recipient of the transplant may have received one or more of a variety of allogeneic cells. Allogeneic cells may include, but are not limited to, blood cells, stem cells, cardiomyocytes, neurons, lymphocytes, NK cells, NKT cells, T reg cells, macrophages, dendritic cells, and pancreatic islet cells. In some embodiments, the allogeneic cells are allogeneic blood cells. Allogeneic blood cells may include hematopoietic stem cells (i.e., HSCs), T cells, B cells, and CAR T cells, NK cells, NKT cells, TILs. In some embodiments, the allogeneic cells are allogeneic T cells. In some embodiments, allogeneic cells are administered as bone marrow, cord blood, or purified allogeneic cells. In some embodiments, the allogeneic cells are bone marrow cells. In some embodiments, the allogeneic cells are cord blood cells. In some embodiments, the transplant comprises HSCs. In some embodiments, the HSCs are administered as bone marrow, cord blood, or purified HSCs. In some embodiments, the HSCs are derived from a donor. In some embodiments, the HSCs are administered as a hematopoietic cell transplantation.

In some embodiments of the methods of the present disclosure, the transplant comprises stem cells. In some embodiments, the allogeneic stem cells are embryonic, tissue-specific, mesenchymal, induced pluripotent, hematopoietic, mesenchymal, skeletal, myogenic, cardiac, neural, epidermal, or intestinal stem cells. In some embodiments, the allogeneic stem cells are hematopoietic stem cells.

In some embodiments, the transplant is a cellular graft of autologous cells, e.g., a transplant comprising cells that originate from the recipient. These include, but are not limited to, cells taken from the recipient and genetically engineered before re-administration into the same recipient, cells taken from the recipient and cultured before re-administration into the same recipient, cells taken from the recipient and subjected to a manufacturing process before re-administration into the same recipient, and any combination thereof. For example, immune cells such as lymphocytes, NK cells, or macrophages are genetically engineered and used to target and kill specific cancer cells. For example, T cells can be modified to produce special structures called chimeric antigen receptors (CARs) on their surfaces that are engineered to target specific cancer antigens; when these CAR T cells are administered into a recipient patient, the CAR receptors enable the CAR T cells to latch onto their target cancer antigens to kill the cancerous cells while leaving healthy tissues unharmed.

The ex-vivo manipulation of the autologous cells prior to re-administration into the same recipient from whom the cells originated may add new non-self genetic material and, thus, render the autologous cell quasi allogeneic and, thus, detectable by the immune system of the recipient possibly prompting activation of the immune system and, consequently, elevated immune (re)activity.

Autologous cells may include, but are not limited to, blood cells, stem cells, cardiomyocytes, neurons, lymphocytes, NK cells, NKT cells, T reg cells, macrophages, dendritic cells, and pancreatic islet cells, that are genetically engineered and/or subjected to a manufacturing process and/or cultured before re-administration into the same recipient. In some embodiments, the autologous cells are autologous T cells and, following genetic engineering, re-administered as CAR (chimeric antigen receptor) T cells.

Tissue Allografts

In some embodiments, the allograft is a tissue transplant. Exemplary tissues include, but are not limited to, connective tissue, epithelial tissue, muscular tissue, nervous tissue, fat tissue, dense fibrous tissue, skeletal muscle, cardiac muscle, or smooth muscle. The muscle tissue may comprise muscle fibers or myocytes. In some cases, the tissue is a bone or tendon (both referred to as musculoskeletal grafts).

Samples from Recipients of Transplants

The methods and kits of the present disclosure involve the analysis of expression levels of one or more informative genes in a sample (e.g., a biological sample) obtained from a transplant recipient in order to inform on the status of immune (re)activity in the recipient and, further, on the status of the transplant. In general, the sample can be any body fluid, tissue, or cells, including whole blood samples, plasma, serum, lymph, peripheral blood mononuclear cells, urine, buccal swabs, bone marrow, or saliva. In some embodiments, the sample is urine or derived from urinary cells. In certain embodiments, the sample is derived from whole blood or a fraction thereof, e.g., serum or plasma.

In some embodiments, the sample obtained from the recipient of a transplant may include whole blood, whole blood cells, isolated blood cells, or DNA or other nucleic acids extracted from the whole blood, whole blood cells, or isolated blood cells. Isolated blood cells may include peripheral blood mononuclear cells (i.e., PMBCs), hematopoietic stem cells (i.e., HSCs), lymphoid progenitor cells, myeloid progenitor cells, white blood cells, granulocytes, agranulocytes, myeloblasts, basophils, eosinophils, neutrophils, mast cells, lymphocytes, monocytes, macrophages, nucleated red blood cells, erythroblasts, megakaryocytes, natural killer cells, B cells, T cells, helper T cells, inducer T cells, regulatory T cells, and cytotoxic T cells, NK cells, NKT cells. In some embodiments, the sample obtained from the recipient of a transplant is whole blood.

In some embodiments, the sample obtained from the recipient of a transplant is a plasma sample. In some embodiments, the sample obtained from the recipient of a transplant is a serum sample. In some embodiments, the sample obtained from the recipient of a transplant is a urine sample.

Once a sample is obtained, it can be used directly, frozen, or otherwise stored in a condition that maintains the integrity of the nucleic acids and prevents degradation and/or contamination of the sample. The amount of a sample that is taken at a particular time may vary and may depend on additional factors, such as any need to repeat analysis of the sample. In some embodiments, up to 50, 40, 30, 20, 10, 9, 8, 7, 6, 5, 4, 3, 2, 1, 0.5, 0.1 mL of a sample is obtained. In some embodiments, 0.1-1, 1-50, 2-40, 3-30, or 4-20 mL of a sample is obtained. In some embodiments, more than 1, 5, 10, 15, 20, 25, 30, 35, 40, 45, 50, 55, 60, 65, 70, 75, 80, 85, 90, 95, or 100 mL of a sample is obtained.

Samples may be obtained from a recipient of a transplant once or more than once. Where multiple samples are to be obtained from a recipient of a transplant, the frequency of sampling may vary. For example, samples may be obtained about once every day, once every other day, once every three days, about once every week, about once every two weeks, about once every three weeks, about once every month, about once every two months, about once every three months, about once every four months, about once every five months, about once every six months, about once every year, or about once every two years or more after the initial sampling event. One, two, three, four, five, ten, twenty, thirty, forty, fifty, sixty, seventy, eighty, ninety, one hundred, two hundred, three hundred, four hundred, or five hundred or more samples may be obtained from the recipient.

One or more samples may be obtained from a recipient of a transplant over a time interval for use in determining the status of immune (re)activity in the transplant recipient and, further, the status of the transplant according to the methods of the present disclosure. The time interval during which samples are taken from the recipient of a transplant following the transplantation event may vary. Exemplary intervals for sampling are described, for example, in U.S. application Ser. No. 14/658,061, which is hereby incorporated by reference in its entirety. For example, samples may be taken from a transplant recipient at various times and over various periods of time for use in determining the status of immune activity in the recipient according to the methods of the present disclosure. For example, samples may be taken from the transplant recipient within days and weeks after, about three months after, about six months after, about nine months after, or less than one year after the transplant event. Samples may be taken from the transplant recipient at various times before the one-year anniversary of the transplant event, at the one-year anniversary of the transplant event, or at various times after the one-year anniversary of the transplant event. For example, at the one-year anniversary after a transplant, samples may be taken from the transplant recipient starting at month 12 (i.e., the one-year anniversary of the transplant event) and continuously for periods of time after this. In some embodiments, the time period for obtaining samples from a transplant recipient is within the first few days post-transplantation. This may be done to monitor induction therapy. In some embodiments, the time period for obtaining samples from a transplant recipient is during tapering of the immunosuppressive regimen, a period that occurs during the first 12 months post-transplantation. In some embodiments, the time period for obtaining samples from a transplant recipient is during the initial long term immunosuppressive maintenance phase, beginning about 12-14 months post-transplantation. In some embodiments, the time period for obtaining samples from a transplant recipient is during the entire long-term maintenance of the immunosuppressive regimen, any time beyond 12 months post-transplantation.

Where multiple samples are to be obtained from a transplant recipient, the frequency of sampling may vary. After samples have begun to be taken from a transplant recipient, samples may be obtained about once every week, about once every 2 weeks, about once every 3 weeks, about once every month, about once every two months, about once every three months, about once every four months, about once every five months, about once every six months, about once every year, or about once every two years or more after the initial sampling event.

In some embodiments, samples are obtained from a recipient of a transplant twice a week in the first three weeks after transplantation. In some embodiments, samples are obtained daily for the first one or two weeks following transplantation. In some embodiments, samples are obtained once a week for the first three months after transplantation. In some embodiments, samples are obtained once a month for the first year after transplantation. In some embodiments, samples are obtained four times a year after the first year after transplantation.

In some embodiments, samples are obtained from a recipient of a transplant for one to three consecutive months, starting at the one-year anniversary of the transplantation event (i.e., 12 months after the transplantation event), providing a total of four to six samples for analysis taken over a three-month time interval, with samples being collected about every two weeks. In some embodiments, a recipient of a transplant has samples taken once a week for one to three consecutive months, starting at the one-year anniversary of the transplantation event (i.e., 12 months after the transplantation event), providing a total of twelve samples for analysis taken over a three-month time interval. The total duration of obtaining samples from a recipient of a transplant, as well as the frequency of obtaining such samples, may vary and will depend on a variety of factors, such as clinical progress. For example, a recipient of a transplant may have samples obtained for analysis of total RNA or nucleic acids for the duration of their lifetime. Appropriate timing and frequency of sampling will be able to be determined by one of skill in the art for a given recipient of a transplant.

Determining Expression Levels of Informative Genes or Genes of Interest

The methods and kits of the present disclosure involve determining expression levels of one or more informative genes from a recipient of a transplant. In some embodiments, the methods of the present disclosure involve applying a trained classifier to the expression levels of the one or more genes to distinguish two or more conditions, e.g., immune quiescence and rejection. In some embodiments, the methods described herein involve generating one or more gene expression signature scores by applying a trained classifier to the expression levels of the one or more genes. In general, expression levels of one or more informative genes are informative with respect to the status of immune activity and, further, the status of the transplant of a transplant recipient, as described in detail below.

Detecting RNA Levels

In some embodiments, provided herein are methods comprising providing nucleic acids from a sample obtained from a transplant recipient. Nucleic acids generally refer to nucleic acids that are present in a sample as described herein (e.g., a whole blood sample, a serum sample, a plasma sample, or a urine sample). In some embodiments, the expression levels of one or more informative genes are determined by analyzing nucleic acids from a sample from a transplant recipient. In some embodiments, the expression levels of one or more informative genes are determined by analyzing nucleic acids from a first sample from a transplant recipient.

In some embodiments, the nucleic acids from the sample comprise RNA. In some embodiments, the nucleic acids from the sample comprise total RNA. In some embodiments, the nucleic acids from the sample comprise mRNA. In some embodiments, the nucleic acids from the sample comprise cell-free nucleic acids, such as cell-free RNAs (cfRNAs).

In some embodiments, the nucleic acids are isolated from a sample from a transplant recipient. Various methods of isolating nucleic acids are well-known in the art and described herein (e.g., methodologies such as those described in Sambrook et al. *Molecular Cloning: A Laboratory Manual* 3rd edition (2001) Cold Spring Harbor Laboratory Press, Cold Spring Harbor, N. Y.; F. M. Ausubel, et al. eds., *Current Protocols in Molecular Biology*, latest edition). Once the nucleic acids are isolated, they can be used directly, frozen, or otherwise stored in a condition that maintains the integrity and prevents degradation and/or contamination of the nucleic acids. Nucleic acids isolated from a recipient of a transplant may be processed for downstream applications and analysis, such as analysis of expression levels of one or more informative genes. An exemplary method of isolating nucleic acids from samples from transplant recipients is described in Examples 2 and 4.

In some embodiments, expression levels are determined by analyzing total RNA from the sample, e.g., using RNA-sequencing. In some embodiments, expression levels are determined by analyzing mRNA from the sample. To quantify RNA levels (e.g., total RNA levels, mRNA levels) in a sample from a transplant recipient, RNA is isolated from the sample. RNA isolation may be performed using commercial purification kits, buffer sets, and proteases in accordance to the manufacturers' instructions or any suitable method. In some embodiments, mRNA is isolated from the nucleic acids from the sample, e.g., by polyA-selection. In some embodiments, the RNA or polyA-selected mRNA is fragmented. In some embodiments, cDNA is synthesized using the fragmented RNA or mRNA as a template. The cDNA may be then subjected to 3' adenylation and 5' end repair. Sequencing adaptors may be ligated onto the 3' adenylation and 5' end repaired cDNA, and the adaptor-ligated cDNA may then be amplified prior to sequencing. In some embodiments, RNA levels are quantified without amplification and/or reverse transcription to cDNA, e.g., using the NanoString Technologies nCounter® system. An exemplary method of performing RNA-sequencing on nucleic acids from samples from transplant recipients using a targeted RNA sequencing panel is described in Examples 2 and 4.

In some embodiments, the nucleic acids from a sample from a transplant recipient are amplified. Methods of amplifying nucleic acids (e.g., cDNA) are well-known in the art and are described herein. Amplification generally refers to any device, method, or technique that can generate copies of a nucleic acid. Amplification of nucleic acids may involve, for example, polymerase chain reaction (PCR)-based methods such as standard PCR, hot-start PCR, multiplex PCR, GC-rich PCR, touchdown PCR, quantitative PCR, digital PCR, and the like. The Fluidigm Access Array™ System, the RainDance Technologies RainDrop system, or other technologies for multiplex amplification may be used for multiplex or highly parallel simplex DNA amplification. In some embodiments, amplification may involve the use of high-fidelity polymerases such as, for example, FastStart High Fidelity (Roche), Expand High Fidelity (Roche), Phusion Flash II (ThermoFisher Scientific), Phusion Hot Start II (ThermoFisher Scientific), KAPA HiFi (Kapa BioSystems), or KAPA2G (Kapa Biosystems).

Amplification may include an initial PCR cycle that adds one or more unique sequences to each individual molecule, called molecular indexing. Unique sequences for molecular indexing can also be ligated to the cDNA after amplification. Molecular indexing allows for quantitative assessment of the absolute levels of RNA from the cDNA amplicon and therefore may improve precision and accuracy in determining the gene expression levels.

Amplified cDNA may also be subjected to additional processes, such as sample indexing (also referred to as sample barcoding or tagging). Methods of sample indexing of DNA are well-known in the art and are described herein. Sample indexing allows for the use of multiplex-sequencing platforms, which are compatible with a variety of sequencing systems, such as Illumina HiSeq, MiSeq; ThermoFisher Scientific Ion PGM and Ion Proton; GenapSys Sequencer; and Oxford Nanopore Flongle, MinION, GridION, and PromethION. Multiplex sequencing permits the sequencing of DNA from multiple samples at once through the use of DNA indexing to specifically identify the sample source of the sequenced DNA.

The amount of nucleic acid that is used for analysis may vary. In some embodiments, less than 1 pg, 5 pg, 10 pg, 20 pg, 30 pg, 40 pg, 50 μg, 100 pg, 200 pg, 500 pg, 1 ng, 5 ng, 10 ng, 20 ng, 30 ng, 40 ng, 50 ng, 100 ng, 200 ng, 500 ng, 1 μg, 5 μg, 10 μg, 20 μg, 30 μg, 40 μg, 50 μg, 100 μg, 200 μg, 500 μg, or 1 mg of nucleic acid are obtained from the sample for further analysis. In some cases, about 1-5 pg, 5-10 pg, 10-100 pg, 100 pg-1 ng, 1-5 ng, 5-10 ng, 10-100 ng, or 100 ng-1 μg of nucleic acid are obtained from the sample for further analysis.

The methods of the present disclosure involve sequencing nucleic acids as well as analyzing sequence data. Various methods and protocols for nucleic acid sequencing and analysis are well-known in the art and are described herein. For example, methods of determining gene expression signatures that are directed to quantifying the expression of nucleic acid transcripts in a sample include polymerase chain reaction (PCR) arrays, real-time polymerase chain reaction, digital PCR, hybridization, in situ hybridization, PCR with in situ hybridization, northern blot analysis, DNA microarrays, ribonuclease protection assays, serial analysis of gene expression, and nucleic acid sequencing such as RNA sequencing, with or without prior conversion of the RNA to cDNA by reverse transcription or amplification. For example, nucleic acid sequencing may be accomplished using high-throughput RNA or DNA sequencing techniques. Examples of next-generation and high-throughput sequencing include, for example, massively parallel signature sequencing, polony sequencing, 454 pyrosequencing, Illumina (Solexa) sequencing (e.g., HiSeq, MiSeq, other platforms), SOLiD sequencing, ion semiconductor sequencing (Ion Torrent), DNA nanoball sequencing, heliscope single molecule sequencing, single molecule real time (SMRT) sequencing, MassARRAY®, and Digital Analysis of Selected Regions (DANSR™). See, e.g., Stein (2008) *Genetic Engineering & Biotechnology News* 28(15); Quail et al. (2012) *BMC Genomics* 13(1):341; Liu et al. (2012) *J of Biomedicine and Biotechnology* 2012:1-11; Oeth et al. (2009) *Methods Mol Biol.* 578:307-43; Chu et al. (2010) *Prenatal Diagnosis* 30:1226-1229; and Suzuki et al. (2008) *Clinica Chimica Acta International Journal of Clinical Chemistry* 387:55-8). Similarly, software programs for primary and secondary analysis of sequence data are well-known in the art.

Where there are multiple nucleic acid samples from one or more recipients of a transplant to be sequenced, such as when multiple samples are taken from one or more recipients of a transplant over a specific time interval, each sample may be sequenced individually, or multiple samples may be sequenced together using multiplex, barcoded sequencing.

Detecting Protein Levels

As described above, in some embodiments, gene expression levels are determined by analyzing nucleic acids (mRNA, cDNA). However, such gene expression levels can also be determined by analyzing proteins or polypeptides that are the expression products of the one or more informative genes (e.g., DCAF12, FLT3, IL1R2, PDCD1, and/or MARCH8). Methods of quantifying the level of proteins of interest are known in the art. For example, in some embodiments, the expression levels of protein products of one or more informative genes are determined by enzyme-linked immunosorbent assay (ELISA), immunohistochemistry, Western blot, mass-spectrometry, high-performance liquid chromatography (HPLC), liquid chromatography-mass spectrometry (LC/MS), or immunoprecipitation.

Analyzing Expression Levels of Informative Genes or Genes of Interest

In general, in various embodiments, nucleic acids or proteins from samples from transplant recipients are analyzed to determine the expression level of one or more informative genes. As described in detail below, quantification of such differential gene expression may be used to determine the status of immune activity and, further, the status of a transplant in a transplant recipient, to discriminate immune quiescence from active transplant rejection, and, furthermore, to discriminate immune quiescence from antibody-mediated rejection (ABMR), T cell-mediated rejection (TCMR), or mixed ABMR/TCMR rejection. Quantification of differential gene expression may furthermore be used to inform about a transplant recipient's status of medication adherence, and about the need to initiate, adjust, or maintain immunosuppressive treatment of the transplant recipient, as described below.

In some embodiments, the expression levels of one or more informative genes are normalized by comparison to expression levels of one or more endogenous reference genes. In general, reference genes are those with expression levels relatively stable across a large set of samples with different clinical features, or genes with relatively uniform expression across different cell or tissue types. Preferably, the reference genes are expressed at a level which is suitable for accurate measurement by the chosen method. Exemplary reference genes are described in Example 2 (Table 4) and Example 4 (Table 8).

In some embodiments, the methods of the present disclosure involve applying a trained classifier to the gene expression levels. In some embodiments, the gene expression levels are normalized against reference gene expression levels. In some embodiments, application of a trained classifier to the (normalized) gene expression levels produces one or more gene expression signature scores.

In some embodiments, the trained classifier comprises a multivariate-based algorithm. An exemplary method of applying a classifier, using five informative genes and 15 reference genes, is described in Examples 2 and 4.

In some embodiments, the expression levels, which may be normalized, of one or more informative genes are used to calculate a quantitative gene expression score that can be used to predict the likelihood of a clinical outcome, e.g., immune quiescence or transplant rejection, in a transplant recipient based on a particular cut-off value. For example, such a gene expression score would enable a healthcare provider to identify transplant recipients who have a high likelihood of immune quiescence and therefore do not require initiation, increase, and/or modification of their immunosuppressive treatment, or have a high likelihood of transplant rejection and therefore would require initiation, increase, and/or modification of their immunosuppressive treatment. Furthermore, such a gene expression score, when indicating a status of immune quiescence, particularly over a period of time, would enable a healthcare provider to identify transplant recipients who likely adhere to their prescribed immunosuppressive treatment. Likewise, such a gene expression score, when indicating a status of rejection, particularly over a period of time, would enable a healthcare provider to identify transplant recipients who likely do not adhere to their prescribed immunosuppressive treatment.

One or more quantitative gene expression signature scores may be determined by the application of a classifier or specific algorithm. The classifier used to calculate the one or more quantitative scores may group the gene expression levels, e.g., normalized against reference genes, of two or more genes, and weigh the grouped gene expression levels based on relevance and/or knowledge of the relative contribution of each gene. The one or more quantitative gene expression score can then be compared to one or more cut-off value that indicates the presence or absence of a change in immune activity of the transplant recipient. In one embodiment, a score below a particular cut-off value may indicate the absence of a change in immune activity and, consequently, indicate a high likelihood of immune quiescence. In another example, a score above a particular cut-off value may indicate the presence of a change in immune activity, and, consequently, indicate a likelihood of transplant rejection.

Exemplary cut-off values are described in the Examples of the present application. In some embodiments, cut-off values are referred to as gene expression signature scores or thresholds. Exemplary gene expression signature scores are described herein in Examples 2 and 4. For example, a gene expression signature score, or cut-off value or threshold, of 11.5 may be used to distinguish between immune quiescence and transplant rejection. In some embodiments, a gene expression score of $<11.5$ indicates that immune quiescence is likely. In some embodiments, a gene expression score of $>11.5$ indicates that rejection is likely.

In certain embodiments, samples from a transplant recipient are analyzed to determine normalized expression levels of one or more informative genes to determine whether they are equal to or below a cut-off value that indicates a certain likelihood of immune quiescence.

In certain embodiments, samples from a transplant recipient are analyzed, particularly over a period of time, to determine normalized expression levels of one or more informative genes to determine whether they are equal to or below a cut-off value that indicates a certain likelihood of medication adherence or compliance.

In certain embodiments, samples from a transplant recipient are analyzed to determine normalized expression levels of one or more informative genes to determine whether they are equal to or above a cut-off value that indicates a certain likelihood of transplant rejection.

In certain embodiments, samples from a transplant recipient are analyzed to determine normalized expression levels of one or more informative genes to determine whether they are equal to or above a cut-off value that indicates a state of elevated immune activity or immune activation that is caused by an infection.

In some embodiments, a sample from a transplant recipient is analyzed to generate a gene expression signature that includes expression levels of at least one informative gene, usually a plurality of genes whereby a plurality can mean at least two informative genes, at least three informative genes, at least four informative genes, or at least five informative genes.

Methods of Determining the Status of a Transplant

The methods of the present disclosure for determining expression levels of one or more informative genes in a sample from a recipient of a transplant can be informative with respect to determining the status of a transplant in a recipient, based on the presence or absence of a change in immune activity as indicated by the gene expression signature or score. Following transplantation of, e.g., an organ, tissue, or cells, the recipient may experience immune quiescence, which is a state that can be characterized by the absence or low levels of immune activity or absence of rejection-associated clinical symptoms. Alternatively, the recipient may experience active rejection, which may be due to T cell-mediated rejection, antibody-mediated rejection, or a combination of the two (i.e., a "mixed" rejection), and which is a state that can be characterized by the presence of immune (re)activity, as measured by a change in gene expression of the one or more informative genes. Accordingly, the status of a transplant may be immune quiescence, active rejection, T cell-mediated rejection, antibody-mediated rejection, or mixed rejection.

In general, expression levels of one or more informative genes as described herein (e.g., DCAF12, FLT3, IL1R2, PDCD1, and/or MARCH8), expressed as quantitative gene expression signature scores following the application of a trained classifier, are informative with regard to the health status of a transplant in a recipient. Accordingly, the methods described herein may be used to discriminate between statuses, detect the status of a transplant, or assess the likelihood of a recipient of a transplant experiencing a particular status. In some embodiments, the status of a transplant is informative with regard to the need for adjustment, e.g., increase, decrease, change, or initiation, of the immunosuppressive treatment of a recipient of the transplant. In some embodiments, the status of a transplant is informative with regard to a transplant recipient's medication adherence. In some embodiments, the status of the transplant enables a clinical decision. Exemplary methods are described in detail below.

Methods of Detecting or Monitoring Immune Quiescence

In one aspect, the present disclosure provides a method of detecting or monitoring immune quiescence in a transplant recipient. The analysis of gene expression provides one or more gene expression signatures or gene expression profiles (GEP) that can be utilized to monitor the immune system for signs of immune activation or elevated immune activity that may be evidenced by the increased or decreased expression of genes that are associated with immune response regulating pathways, e.g., genes associated with immune response-regulating pathways of inflammation, corticosteroid sensitivity, and T cell activation. Signs of elevated immune activity may indicate the development or presence of an allograft rejection or the risk thereof, or a state of immune activation that is caused by an infection.

Likewise, such one or more gene expression signatures or profiles may provide an indication of the resting, quiescent state of cells of the immune system and can be utilized to monitor immune quiescence as a continuance of the resting, quiescent state of the cells of the immune system indicating immune quiescence and, thus, the absence of rejection. Such gene expression signatures or profiles may provide an indication of the resting, quiescent state of cells of the immune system and can also be utilized to monitor immune quiescence as a return to a resting, quiescent state of the cells of the immune system in response to treatment following an event that may have been a rejection, a systemic viral, bacterial or fungal infection, a discontinuation of immunosuppressive medication or a deviation from a particular immunosuppressive medication schedule.

In some embodiments, the method of detecting or monitoring immune quiescence comprises providing nucleic acids from a first sample obtained from the transplant recipient and determining expression levels of one or more genes associated with an immune response-regulating pathway of inflammation, corticosteroid sensitivity, and/or T cell activation, as described above. In some embodiments, the method comprises generating quantitative gene expression signature scores by applying a trained classifier to the expression levels of the one or more genes. In some embodiments, gene expression signature scores being equal to or below a cut-off value indicate that the transplant recipient is likely experiencing immune quiescence. In some embodiments, the method comprises detecting immune quiescence if the gene expression signature scores are determined to be equal to or below the cut-off value. Further, the methods of detecting or monitoring immune quiescence may be used in other methods of the present disclosure, as described below. In some embodiments, detecting or monitoring immune quiescence may be informative with regard to a clinical decision involving the treatment of a recipient of a transplant, for example, with respect to the need for adjusting, e.g., increasing, decreasing, changing, or initiating, the immunosuppressive treatment of the recipient. Detecting or monitoring immune quiescence may also be informative with regard to a clinical decision involving the need for performing a transplant biopsy. If a transplant recipient is found to experience immune quiescence, a biopsy may not be needed, thereby sparing the recipient an invasive, risky and often inconclusive procedure.

In some embodiments, the presence of immune quiescence is informative with regard to the need for adjustment of the treatment of a recipient of the transplant, e.g., by decreasing, changing, or even suspending the immunosuppressive treatment of the recipient.

The presence of immune quiescence indicates that the immune system of a transplant recipient is not in an activated or reactive state. This can, for example, be characterized by an absence or low levels of immune activity or absence of rejection-associated clinical symptoms or an absence of infection. The methods of the present disclosure for detecting or monitoring for immune quiescence, and for discriminating immune quiescence from allograft rejection may be employed for general surveillance of a transplant recipient to test for an absence or for low levels of immune activity. In some embodiments, the methods for detecting or monitoring for immune quiescence, and for discriminating immune quiescence from allograft rejection may be employed for general surveillance of a transplant recipient who shows little or no clinical signs of rejection or who has no clinically indicated need for a biopsy. In some embodiments, the methods for detecting or monitoring for immune quiescence, and for discriminating immune quiescence from allograft rejection may be employed for assessment of a transplant recipient who shows clinical signs of rejection or who has a clinically indicated need for a biopsy.

Methods of Discriminating Between Active Rejection and Immune Quiescence

In one aspect, the present disclosure provides a method of discriminating between active rejection and immune quiescence in a transplant recipient. In some embodiments, the method of discriminating between active rejection and immune quiescence comprises providing nucleic acids from a first sample obtained from the transplant recipient and determining expression levels of one or more genes associated with an immune response-regulating pathway of inflammation, corticosteroid sensitivity, and/or T cell activation, as described above. In some embodiments, the method comprises generating one or more quantitative gene expression signature scores by applying a trained classifier to the expression levels of the one or more genes. In some embodiments, gene expression signature scores being equal to or above a cut-off value indicate that the transplant recipient is likely experiencing active rejection or is at risk of developing active rejection, and gene expression signature scores being below the cut-off value indicate that the transplant recipient is likely experiencing immune quiescence. In some embodiments, the method comprises detecting active rejection or detecting a risk of developing active rejection if the gene expression signature scores are determined to be equal to or above the cut-off value. Further, the methods of discriminating between active rejection and immune quiescence may be used in other methods of the present disclosure, as described below. In some embodiments, discriminating between active rejection and immune quiescence may be informative with regard to a clinical decision involving the treatment of a recipient of a transplant, for example, with respect to the need for adjusting, e.g., increasing, decreasing, changing, or initiating, the immunosuppressive treatment of the recipient. Discriminating between active rejection and immune quiescence may also be informative with regard to a clinical decision involving the need for performing a transplant biopsy. If a transplant recipient is found to experience immune quiescence, a biopsy may not be needed, thereby sparing the recipient an invasive, risky, and often inconclusive procedure.

In general, gene expression signature scores being equal to or above a suitable cut-off value are informative with regard to whether the transplant recipient experiences active rejection or is at risk of developing active rejection. In some embodiments, the presence of active rejection or the risk of active rejection enables a clinical decision. In some embodiments, the presence of active rejection or the risk of active rejection is informative with regard to the need for adjustment of the treatment of a recipient of the transplant. In some embodiments, the presence of immune quiescence enables a clinical decision involving the need for performing a transplant biopsy. In some embodiments, the presence of immune quiescence is informative with regard to the need for adjustment of the treatment of a recipient of the transplant.

Methods of Discriminating Between T Cell-Mediated Rejection and Antibody-Mediated Rejection The methods of the present disclosure for determining expression levels of one or more informative genes in a sample from a recipient of a transplant and, subsequently, generating one or more gene expression signature scores by applying a trained classifier can be informative with respect to discriminating between T cell-mediated rejection and antibody-mediated rejection. In some embodiments, a method is provided comprising providing nucleic acids from a first sample obtained from the transplant recipient and determining expression levels of one or more genes associated with an immune response-regulating pathway of inflammation, corticosteroid sensitivity, and/or T cell activation, generating one or more gene expression signature scores by applying a trained classifier to the expression levels of the one or more genes, as described above. In some embodiments, gene expression signature scores being equal to or above a first cut-off value indicate that the transplant recipient is likely experiencing T cell-mediated rejection or is at risk of developing T cell-mediated rejection, and gene expression scores being equal to or above a second cut-off value indicate that the transplant recipient is likely experiencing antibody-mediated rejection or is at risk of developing antibody-mediated rejection. In some embodiments, the method comprises detecting T cell-mediated rejection if the gene expression scores are determined to be equal to or above the first cut-off value and detecting antibody-mediated rejection if the gene expression signature scores are determined to be equal to or above the second cut-off value.

In general, gene expression signature scores being equal to or above a suitable first cut-off value are informative with regard to a likelihood that the transplant recipient experiences T cell-mediated rejection or is at risk of developing T cell-mediated rejection. Further, in general, gene expression signature scores being equal to or above a suitable second cut-off value are informative with regard to a likelihood that the transplant recipient experiences antibody-mediated rejection or is at risk of developing antibody-mediated rejection. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the treatment of a recipient of the transplant. In some embodiments, the presence of antibody-mediated rejection or the risk of developing antibody-mediated rejection is informative with regard to the need for adjustment of the treatment of a recipient of the transplant.

Methods of Discriminating Between Immune Quiescence, T Cell-Mediated Rejection, and Antibody-Mediated Rejection The methods of the present disclosure for determining expression levels of one or more informative genes in a sample from a recipient of a transplant can be informative with respect to discriminating between immune quiescence, T cell-mediated rejection, and antibody-mediated rejection in a transplant recipient. In some embodiments, a method is provided comprising providing nucleic acids from a first sample obtained from the transplant recipient and determining expression levels of one or more genes associated with an immune response-regulating pathway of inflammation, corticosteroid sensitivity, and/or T cell activation, and generating one or more gene expression signature scores by applying a trained classifier to the expression levels of the one or more genes. In some embodiments, gene expression scores being equal to or above a first cut-off value indicate that the transplant recipient is likely experiencing T cell-mediated rejection or is at risk of developing T cell-mediated rejection, gene expression signature scores being equal to or above a second cut-off value indicate that the transplant recipient is likely experiencing antibody-mediated rejection or is at risk of developing antibody-mediated rejection, and gene expression signature scores being below the first and the second cut-off value indicate that the transplant recipient is likely experiencing immune quiescence.

In some embodiments, the method comprises detecting T cell-mediated rejection if the gene expression signature scores are determined to be equal to or above the first cut-off value and detecting antibody-mediated rejection if the gene expression signature scores are determined to be equal to or above the second cut-off value.

In general, gene expression signature scores being equal to or above a suitable first cut-off value are informative with regard to a likelihood that the transplant recipient experiences T cell-mediated rejection or is at risk of developing T cell-mediated rejection. Further, in general, gene expression signature scores being equal to or above a suitable second cut-off value are informative with regard to a likelihood that the transplant recipient experiences antibody-mediated rejection or is at risk of developing antibody-mediated rejection. In general, gene expression signature scores below the first and the second cut-off values are informative with regard to a likelihood that the transplant recipient experiences immune quiescence. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the treatment of a recipient of the transplant. In some embodiments, the presence of antibody-mediated rejection or the risk of developing antibody-mediated rejection is informative with regard to the adjustment of the treatment of a recipient of the transplant. In some embodiments, the presence of immune quiescence enables a clinical decision. In some embodiments, the presence of immune quiescence is informative with regard to the need for adjustment of the treatment of a recipient of the transplant.

Methods of Detecting, Monitoring, and/or Guiding Treatment of Active Rejection

The methods of the present disclosure for determining expression levels of one or more informative genes in a sample from a recipient of a transplant can be informative with respect to detecting, monitoring, and/or guiding treatment of active rejection in a transplant recipient. In some embodiments, the transplant recipient is on an immunosuppressive treatment. In some embodiments, provided herein is a method comprising providing nucleic acids from a first sample obtained from the transplant recipient, and determining expression levels of one or more genes associated with an immune response-regulating pathway of inflammation, corticosteroid sensitivity, and/or T cell activation, and generating one or more gene expression signature scores by applying a trained classifier to expression levels of the one or more genes, as described above. In some embodiments, gene expression signature scores equal to or above a cut-off value indicate that the transplant recipient is likely experiencing active rejection or is at risk of developing active rejection. In some embodiments, the method comprises detecting active rejection if the gene expression signature scores are determined to be equal to or above the cut-off value. In some embodiments, the method further comprises treating the rejection, or risk thereof, by administering to the recipient an immunosuppressive agent, bolus steroid treatment, intravenous immunoglobulin, plasmapheresis and/or increasing the dosage of an immunosuppressive or anti-rejection agent that the recipient already received.

In general, gene expression signature scores equal to or above a cut-off value are informative with regard to a likelihood that the transplant recipient experiences active rejection or is at risk of developing active rejection. In some embodiments, the presence of active rejection or the risk of developing active rejection enables a clinical decision. In some embodiments, the presence of active rejection or the risk of developing active rejection is informative with regard to the adjustment of the immunosuppressive treatment of a recipient of the transplant. In some embodiments, the presence of active rejection indicates a need to administer to the recipient an immunosuppressive or anti-rejection agent, bolus steroid treatment, intravenous immunoglobulin, plasmapheresis and/or increase the dosage of an immunosuppressive or anti-rejection agent that the recipient already received. In some embodiments, the presence of active rejection indicates a need to monitor the recipient of the transplant more frequently.

Methods of Detecting and Distinguishing T Cell-Mediated Rejection from Antibody Mediated Rejection The methods of the present disclosure for determining expression levels of one or more informative genes in a sample from a recipient of a transplant can be informative with respect to detecting and distinguishing T cell-mediated rejection from antibody mediated rejection in a transplant recipient. In some embodiments, the transplant recipient is on an immunosuppressive treatment. In some embodiments, provided herein is a method comprising providing nucleic acids from a first sample obtained from the transplant recipient, and determining expression levels of one or more genes associated with an immune response-regulating pathway of inflammation, corticosteroid sensitivity, and/or T cell activation, and generating one or more gene expression signature scores by applying a trained classifier to expression levels of the one or more genes, as described above. In some embodiments, gene expression signature scores equal to or above a cut-off value indicate that the transplant recipient is likely experiencing T cell-mediated rejection or is at risk of developing T cell-mediated rejection. In some embodiments, the method comprises detecting T cell mediated rejection if the gene expression signature scores are determined to be equal to or above the cut-off value. In some embodiments, the method further comprises treating the rejection by administering to the recipient an immunosuppressive or anti-rejection agent or bolus steroid treatment and/or increasing the dosage of an immunosuppressive or anti-rejection agent that the recipient already received.

In general, gene expression signature scores equal to or above a suitable first cut-off value are informative with regard to a likelihood that the transplant recipient experiences T cell-mediated rejection or is at risk of developing T cell-mediated rejection. Further, in general, gene expression signature scores equal to or above a suitable second cut-off value are informative with regard to a likelihood that the transplant recipient experiences antibody-mediated rejection or is at risk of developing antibody-mediated rejection. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the immunosuppressive treatment of a recipient of the transplant. In some embodiments, the presence of antibody-mediated rejection or the risk of developing antibody-mediated rejection is informative with regard to the adjustment of the immunosuppressive treatment of a recipient of the transplant.

Methods of Assessing the Likelihood of Allograft Rejection

The methods of the present disclosure for determining expression levels of one or more informative genes in a sample from a recipient of a transplant can be informative with respect to assessing the likelihood of allograft rejection in a transplant recipient. In some embodiments, provided herein is a method comprising providing nucleic acids from a first sample obtained from the transplant recipient, and determining expression levels of one or more genes associated with an immune response-regulating pathway of inflammation, corticosteroid sensitivity, and/or T cell activation, and generating gene expression signature scores by applying a trained classifier to expression levels of the one or more genes, as described above. In some embodiments, gene expression signature scores equal to or above a cut-off value indicate a likelihood that the transplant recipient will experience allograft rejection or is at risk of developing allograft rejection. In some embodiments, the method comprises predicting allograft rejection if the gene expression signature scores are determined to be equal to or above the cut-off value.

Methods of Assessing the Likelihood of Antibody-Mediated Rejection

The methods of the present disclosure for determining expression levels of one or more informative genes in a sample from a recipient of a transplant can be informative with respect to assessing the likelihood of antibody-mediated rejection in a transplant recipient. In some embodiments, provided herein is a method comprising providing nucleic acids from a first sample obtained from the transplant recipient, and determining expression levels of one or more genes associated with an immune response-regulating pathway of inflammation, corticosteroid sensitivity, and/or T cell activation, and generating one or more gene expression signature score by applying a trained classifier to expression levels of the one or more genes, as described above. In some embodiments, gene expression signature scores equal to or above a cut-off value indicate a likelihood that the transplant recipient will experience antibody-mediated rejection or is at risk of developing antibody-mediated rejection. In some embodiments, the method comprises predicting antibody-mediated rejection if the gene expression signature scores are determined to be equal to or above the cut-off value.

Methods of Assessing the Likelihood of T Cell-Mediated Rejection

The methods of the present disclosure for determining expression levels of one or more informative genes in a sample from a recipient of a transplant can be informative with respect to assessing the likelihood of T cell-mediated rejection in a transplant recipient. In some embodiments, provided herein is a method comprising providing nucleic acids from a first sample obtained from the transplant recipient, and determining expression levels of one or more genes associated with an immune response-regulating pathway of inflammation, corticosteroid sensitivity, and/or T cell activation, and generating gene expression signature scores by applying a trained classifier to expression levels of the one or more genes, as described above. In some embodiments, gene expression signature scores equal to or above a cut-off value indicate a likelihood that the transplant recipient will experience T cell-mediated rejection or is at risk of developing T cell-mediated rejection. In some embodiments, the method comprises predicting T cell-mediated rejection if the gene expression signature scores are determined to be equal to or above the cut-off value.

Methods of Discriminating Between Immune Quiescence and a State of Immune Activation In one aspect, the present disclosure provides a method of discriminating between immune quiescence and a state of immune activation caused by infection in a transplant recipient. In some embodiments, the method of discriminating between immune quiescence and a state of immune activation comprises providing nucleic acids from a first sample obtained from the transplant recipient and determining expression levels of one or more genes associated with an immune response-regulating pathway of inflammation, corticosteroid sensitivity, and/or T cell activation, as described above. In some embodiments, the method comprises generating gene expression signature scores by applying a trained classifier to the expression levels of the one or more genes. In some embodiments, gene expression signature scores being equal to or above a cut-off value indicate that the transplant recipient likely experiences a state of immune activation or is at risk of developing a state of immune activation. In some embodiment, gene expression signature scores being equal to or above a cut-off value indicate that the transplant recipient likely experiences a state of immune activation caused by infection or is at risk of developing a state of immune activation caused by infection.

Further, the methods of discriminating between immune quiescence and a state of immune activation caused by infection in a transplant recipient may be used in other methods of the present disclosure, as described below. In some embodiments, discriminating between immune quiescence and a state of immune activation caused by infection in a transplant recipient may be informative with regard to a clinical decision involving the continued treatment of a recipient of a transplant, for example, with respect to the need for adjusting, e.g., increasing, decreasing, changing the immunosuppressive treatment of the recipient, or initiating anti-infective therapy. Discriminating between immune quiescence and a state of immune activation caused by infection in a transplant recipient may also be informative with regard to a clinical decision involving the need for performing a transplant biopsy.

Gene expression signature scores equal to or above a cut-off value may occur in case of infection with infectious agents, e.g., viruses such as Cytomegalovirus, Epstein-Barr virus, Anelloviridae, and BK virus; bacteria such as *Pseudomonas aeruginosa*, Enterobacteriaceae, *Nocardia, Streptococcus pneumonia, Staphyloccous aureus*, and *Legionella*; fungi such as *Candida, Aspergillus, Cryptococcus, Pneumocystis carinii*; or parasites such as *Toxoplasma gondii*. If, upon testing for the presence and/or levels of such infectious agents, infection with one or more infectious agents is confirmed, immunosuppressive therapies may be decreased, increased, maintained or modified with respect to dosage and/or immunosuppressive agent(s), and anti-infective therapy may be initiated.

Methods of Detecting or Monitoring Medication Adherence

In one aspect, the present disclosure provides a method of detecting or monitoring medication adherence in a transplant recipient. In some embodiments, the method of detecting or monitoring medication adherence comprises providing nucleic acids from a first sample obtained from the transplant recipient and determining expression levels of one or more genes associated with an immune response-regulating pathway of inflammation, corticosteroid sensitivity, and/or T cell activation, as described above. In some embodiments, the method comprises generating gene expression signature scores by applying a trained classifier to the expression levels of the one or more genes. In some embodiments, gene expression signature scores being equal to or below a cut-off value indicate that the transplant recipient likely adheres to a prescribed medication regimen. In some embodiments, the method comprises detecting medication adherence if the gene expression signature scores are determined to be equal to or below the cut-off value. In some embodiments, gene expression signature scores being equal to or above a cut-off value indicate that the transplant recipient likely lacks adherence to a prescribed medication regimen. In some embodiments, the method comprises detecting lack of medication adherence if the gene expression signature scores are determined to be equal to or above the cut-off value.

Further, the methods of detecting or monitoring medication adherence may be used in other methods of the present disclosure, as described below. In some embodiments, detecting or monitoring medication adherence may be informative with regard to a clinical decision involving the continued treatment of a recipient of a transplant, for example, with respect to the need for special consultation of the recipient, an increase in the frequency of care visits or surveillance, or with respect to the need for adjusting, e.g., increasing, decreasing, changing the immunosuppressive treatment of the recipient. Detecting or monitoring medication adherence may also be informative with regard to a clinical decision involving the need for performing a transplant biopsy. If a transplant recipient is found to adhere to a prescribed medication regimen, a biopsy may not be needed, thereby sparing the recipient an invasive, risky, and often inconclusive procedure. Likewise, if a transplant recipient is found to lack adherence to a prescribed medication regimen, a biopsy may be warranted, or an increase in the frequency of care visits.

In general, gene expression signature scores being equal to or above a suitable cut-off value are informative with regard to whether the transplant recipient lacks adherence to a prescribed medication regimen. In some embodiments, the lack of medication adherence or compliance enables a clinical decision. In some embodiments, the lack of medication adherence or compliance is informative with regard to the need for adjustment of the treatment of a recipient of the transplant. In some embodiments, lack of medication adherence or compliance enables a clinical decision involving the need for performing a transplant biopsy. In some embodiments, the lack of medication adherence or compliance is informative with regard to the need for adjustment of the treatment of a recipient of the transplant.

Methods Involving the Analysis of Transplant-Derived (Donor-Derived) Cell-Free Nucleic Acids The present disclosure further relates to methods involving the analysis of transplant-derived, cell-free nucleic acids, e.g., cell-free DNA, in samples from the recipient of a transplant. In some embodiments, any one of the methods described herein further comprises providing nucleic acids from a sample obtained from the transplant recipient, wherein the sample comprises transplant-derived cell-free nucleic acids and recipient-derived cell-free nucleic acids, sequencing a panel of selected single nucleotide polymorphisms (SNPs) from the cell-free nucleic acids, wherein the panel of SNPs is suitable for differentiating between transplant-derived cell-free nucleic acids and recipient-derived cell-free nucleic acids, determining an amount or levels of transplant-derived cell-free nucleic acids, and diagnosing the status of the transplant, where levels of transplant-derived cell-free nucleic acids, e.g., transplant-derived cell-free DNA, at, below or above a cut-off value, as determined once or over a certain time interval, are indicative of the status of the transplant and a basis for adjusting immunosuppressive therapy, e.g., increasing, changing immunosuppressive therapy. In some embodiments, a one-time determination of levels of transplant-derived cell-free DNA above a cut-off value or an increase in the levels of transplant-derived cell-free DNA over time can be indicative of transplant rejection and a need for adjusting immunosuppressive therapy. In some embodiments, a one-time determination of levels of transplant-derived cell-free DNA below a cut-off value or a decrease in the levels of transplant-derived cell-free DNA over time can be indicative of transplant tolerance, or non-rejection, and a basis for adjusting immunosuppressive therapy, e.g., decreasing, changing immunosuppressive therapy. In some embodiments, no change in the levels of transplant-derived cell-free DNA over time can be indicative of a stable transplant status and a basis for adjusting immunosuppressive therapy, e.g., decreasing, changing, or even discontinuing immunosuppressive therapy.

Some aspects of the present disclosure are based, at least in part, on Applicant's development of techniques for probing the status of allogeneic cells, such as cells derived from a transplant as described herein, in a recipient. Such methods are described, for example, in U.S. application Ser. No. 14/658,061, which is hereby incorporated by reference in its entirety.

The methods of the present disclosure involve the analysis of donor-derived, i.e., transplant-derived, cell-free DNA (dd-cfDNA) from a sample of the recipient of a transplant. After cell-free DNA, comprising both transplant-derived cell-free DNA and recipient-derived cell-free DNA, has been isolated from a sample of the transplant recipient, various methods and techniques may be used to analyze the cell-free DNA, including sequencing a panel of selected single nucleotide polymorphisms (SNPs) that is suitable for differentiating between transplant-derived cell-free DNA and recipient-derived cell-free DNA and assaying differences in SNP allele distribution patterns in the panel as compared to expected homozygous or heterozygous distribution patterns to determine the level of transplant-derived cell-free DNA. In some embodiments, an absolute concentration or amount of transplant-derived cell-free DNA may be determined by adding (spiking in) a known quantity of a suitable control DNA, e.g., control DNA of suitable length, to the sample obtained from the transplant recipient prior to DNA extraction or isolation, and calculating an absolute concentration or amount of transplant-derived cell-free DNA based on a standard curve.

Analysis of transplant-derived cell-free DNA according to the methods of the present disclosure involves analysis of a panel of polymorphic markers from the transplant-derived cell-free DNA. In some embodiments, the polymorphic markers are SNPs. In some embodiments, SNPs are selected to be included in the panel at least in part on the basis that the panel of SNPs will be sufficient to differentiate between transplant-derived cell-free DNA and recipient-derived cell-free DNA.

Panels of Polymorphic Markers

Analysis of transplant-derived cell-free DNA obtained from a recipient of a transplant involves the analysis of a panel of polymorphic markers from the cell-free DNA. Various polymorphic markers may be selected for inclusion in the panel to be analyzed as long as the polymorphic marker panel as a whole is suitable for differentiating between transplant-derived cell-free DNA and recipient-derived cell-free DNA. The same polymorphic marker panel may be used for each recipient of a transplant; there is no need to customize polymorphic marker panels to individualize the panel to different recipients of transplants.

Various types of polymorphic markers may be included in polymorphic marker panels. Polymorphic markers are found at a region of DNA containing a polymorphism. A polymorphism generally refers to the occurrence of two or more genetically determined alternative sequences or alleles in a population. A polymorphism may also refer to epigenetic differences between one or more nucleotides at a particular locus of the DNA, for example, the presence or absence of methylation on a particular nucleotide. A polymorphism may contain, for example, one or more base changes or modifications, an insertion, a repeat, or a deletion. A polymorphic locus may be as small as one base pair, such as a SNP. Polymorphic markers may include, for example, single nucleotide polymorphisms (SNPs), restriction fragment length polymorphisms (RFLPs), short tandem repeats (STRs), variable number of tandem repeats (VNTRs), hypervariable regions, minisatellites, dinucleotide repeats, trinucleotide repeats, tetranucleotide repeats, simple sequence repeats, and insertion elements. A polymorphism between two nucleic acids can be naturally occurring or may be caused by exposure to or contact with chemicals, enzymes, or other agents or exposure to agents that cause damage to nucleic acids, for example, ultraviolet radiation, mutagens, or carcinogens. Additional types of polymorphisms and polymorphic markers will be readily apparent to one of skill in the art.

Various combinations of polymorphic marker types may be used in polymorphic marker panels. For example, the polymorphic marker panel may include both SNPs and short tandem repeats or any other type of polymorphic marker. In some embodiments, the polymorphic marker panel is composed entirely of SNPs; thus, the polymorphic marker panel is a SNP panel. Additional combinations of polymorphic markers on polymorphic marker panels will be readily apparent to one of skill in the art.

Selection of the appropriate quantity and identity of polymorphic markers to be analyzed from cell-free DNA may vary, as will be appreciated by one of skill in the art. The panel of polymorphic markers to be analyzed may include at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 150, at least 200, at least 250, at least 300, at least 350, at least 400, at least 450, at least 500, at least 1000, or at least 1500 or more independent polymorphic markers.

In some embodiments, the polymorphic marker panel is a panel of SNPs. SNPs selected to be included in the SNP panel, or in any other polymorphic marker panel, may be those previously identified as being suitable for differentiating between any two unrelated individuals (e.g., Pakstis et al., (2010) *Hum Genet.* 127(3):315-24). For example, the SNP panel may include one or more of the following human SNPs (named according to dbSNP numbering): rs987640, rs1078004, rs6564027, rs2391110, rs2253592, rs2122080, rs1374570, rs57010808, rs7048541, rs1554472, rs1411271, rs475002, rs9471364, rs7825, rs12529, rs899076, rs8087320, rs10232552, rs1126899, rs909404, rs1052637, rs2175957, rs9951171, rs2245285, rs10743071, rs1051614, rs7017671, rs7284876, rs743616, rs1056149, rs3951216, rs1045644, rs28402995, rs5746846, rs1898882, rs6682717, rs4721083, rs6049836, rs7633246, rs6811238, rs10773760, rs9556269, rs11210490, rs1889819, rs13436, rs1055851, rs11560324, rs4775444, rs4302336, rs7182758, rs10192076, rs7306251, rs1411711, rs9914372, rs13428, rs2229627, rs13281208, rs2275047, rs561930, rs436278, rs3935070, rs1696455, rs1420398, rs13184586, rs1027895, rs10092491, rs344141, rs2255301, rs11126691, rs7173538, rs2070426, rs7161563, rs2099875, rs8058696, rs1600, rs57594411, rs6444724, rs1565933, rs12135784, rs2811231, rs6472465, rs4834806, rs993934, rs2833736, rs6094809, rs1151687, rs6918698, rs10826653, rs2180314, rs745142, rs2294092, rs12797748, rs12321981, rs12901575, rs9379164, rs11019968, rs4958153, rs1678690, rs8070085, rs6790129, rs4843371, rs2291395, rs9393728, rs868254, rs10918072, rs7451713, rs1352640, rs445251, rs3829655, rs9908701, rs1056033, rs4425547, rs1897820, rs1130857, rs4940019, rs34393853, rs2292830, rs11882583, rs9931073, rs12739002, rs11069797, rs7289, rs6807362, rs6492840, rs2509943, rs7526132, rs1522662, rs3129207, rs4806433, rs3802265, rs57985219, rs523104, rs2398849, rs7613749, rs7822225, rs10274334, rs1045248, rs35958120, rs10865922, rs2835296, rs12994875, rs2455230, rs625223, rs2281098, rs7112538, rs3748930, rs4571557, rs4733017, rs35596415, rs9640283, rs9865242, rs2295005, rs3810483, rs2248490, rs464663, rs2571028, rs1288207, rs61202512, rs2498982, rs12309796, rs4843380, rs2279665, rs36657, rs2269355, rs7009153, rs4666736, rs9843077, rs3816800, rs638405, rs3088241, rs590162, rs6443202, rs12646548, rs7315223, rs4501824, rs891700, rs1476864, rs7626681, rs76285932, rs79740603, rs3205187, rs6495680, rs740598, rs13182883, rs13218440, rs321198, rs1019029, rs9905977, rs13134862, rs1109037, rs1049544, rs1547202, rs55843637, rs1736442, rs1872575, rs12997453, rs4606077, rs9790986, rs1498553, rs2227910, rs62490396, rs2292972, rs733398, rs62485328, rs3790993, rs3793945, rs6591147, rs10776839, rs1679815, rs314598, rs12480506, rs6578843, rs9906231, rs10060772, rs901398, rs2007843, rs936019, rs648802, rs28756099, rs214955, rs10817691, rs1523537, rs9866013, rs12146092, rs234650, rs11776427, rs10503926, rs6719427, rs7853852, rs4288409, rs3731877, rs2289751, rs1779866, rs10932185, rs8097, rs7163338, rs12165004, rs3813609, rs985492, rs11106, rs528557, rs2270529, rs12237048, rs6459166, rs4510896, rs2503667, rs2567608, rs1047979, rs41317515, rs3173615, rs7785899, rs4849167, rs408600, rs1477239, rs3780962, rs12547045, rs9464704, rs2297236, rs2505232, rs6838248, rs7029934, rs2279776, rs3740199, rs3803798, rs1340562, rs4688094, rs7311115, rs2229571, rs159606, rs6955448, rs430046, rs17472365, rs3734311, rs7730991, rs2296545, rs12550831, rs6507284, rs254255, rs2733595, rs3812571, rs279844, rs2519123, rs7902629, rs9861037, rs1941230, rs3814182, rs2833622, rs560681, rs2071888, rs4936415, rs7589684, rs576261, rs9262, rs6907219, rs9289122, rs178649, rs208815, rs17818255, rs282338, rs2342767, rs3735615, rs10066756, rs75330257, rs6570914, rs3817687, rs2267234, rs7332388, rs315791, rs8004200, rs2075322, rs2121302, rs4803502, rs10831567, rs521861, rs10488710, rs903369, rs12680079, rs2272998, rs2302443, rs362124, rs10421285, rs6478448, rs7639794, rs2721150, rs259554, rs10500617, rs2358286, rs8025851, rs3848730, rs342910, rs1478829, rs726009, rs2182241, rs150079, rs1064074, rs6766396, rs7601771, rs1894252, rs1127472, rs6055803, rs977070, rs3751066, rs8076632, rs6508485, rs10496031, rs609521, rs1974855, rs35338631, rs1915632, rs8019787, rs2964164, rs7843841, rs6788347, rs6510057, rs2469523, rs12709176, rs9638798, rs7070730, rs12793830, rs2657167, rs7667167, rs2946994, rs2480345, rs3118957, rs10750524, rs7301328, rs722290, rs2289818, rs16964068, rs1821380, rs1112679, rs3190321, rs11648453, rs7205345, rs1049379, rs4890012, rs11081203, rs1048290, rs3826709, rs14155, rs4845480, rs874881, rs1044010, rs76275398, rs7543016, rs6101217, rs2056844, rs9617448, rs1317808, rs12713118, rs2717225, rs357483, rs14080, rs4680782, rs4364205, rs6794, rs10013388, rs1477898, rs11934579, rs448012, rs30353, rs73714299, rs7825714, rs10760016, and rs13295990. In some embodiments, the panel of polymorphic markers to be analyzed may include at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 150, at least 200, at least 250, at least 300, at least 350, or at least 400 of the 405 above mentioned SNPs. In some embodiments, each of the 405 above-mentioned SNPs is included in the polymorphic marker panel.

In some embodiments, the SNP panel may include, for example, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, about 190 to about 200, about 200 to about 210, about 210 to about 220, about 220 to about 230, about 230 to about 240, about 240 to about 250, about 250 to about 260, about 270 to about 280, about 280 to about 290, about 290 to about 300, about 300 to about 310, about 310 to about 320, about 320 to about 330, about 330 to about 340, about 340 to about 350, about 350 to about 360, about 360 to about 370, about 370 to about 380, about 380 to about 390, about 390 to about 400, or about 400 to 405 of the 405 independent SNPs identified above.

In some embodiments, the SNP panel comprises more than 405 SNPs. In some embodiments, the SNP panel comprises at least 500, at least 600, at least 700, at least 800, at least 900, at least 1000, at least 1100, at least 1200, at least 1300, at least 1400, or at least 1500 SNPs.

SNPs may also be selected on the basis of various traits. For example, SNPs may be selected on the basis that they have, an overall population minor allele frequency of ≥0.4, a target population minor allele frequency of ≥0.4, the lowest polymerase error rate (in the test system) of the 6 potential allele transitions or transversions, and/or low linkage on the genome such as, for example, >500 kb distance between each independent SNP. In some embodiments, SNPs are selected on the basis that they have an overall population minor allele frequency of ≥0.4. In some embodiments, SNPs are selected on the basis that they have a target population minor allele frequency of ≥0.4. In some embodiments, SNPs are selected on the basis that they have the lowest polymerase error rate (in the test system) of the 6 potential allele transitions or transversions. In some embodiments, SNPs are selected on the basis that they have low linkage on the genome such as, for example, >500 kb distance between each independent SNP. In some embodiments, SNPs are selected on the basis that they have one, two, three, or four of the above-mentioned traits.

Determining the Status of a Transplant

The methods of the present disclosure involve determining the amount or levels of transplant-derived cell-free DNA in a sample from a recipient of a transplant and can be used to determine the status of the transplant in the recipient of the transplant.

In one aspect, the present disclosure provides a method of determining the status of a transplant in a recipient. In some embodiments, the method of determining the status of a transplant comprises a) providing nucleic acids from a sample obtained from the transplant recipient comprising cell-free nucleic acids that are derived from the transplant and cell-free nucleic acids that are derived from the recipient; b) sequencing a panel of selected single nucleotide polymorphisms (SNPs) from the cell-free DNA, wherein the panel of SNPs is suitable for differentiating between transplant-derived cell-free DNA and recipient-derived cell-free DNA; and c) assaying differences in SNP allele distribution patterns in the panel as compared to expected homozygous or heterozygous distribution patterns to determine the level of transplant-derived cell-free DNA. In some embodiments, an absolute concentration or amount of transplant-derived cell-free DNA may be determined by adding (spiking in) a known quantity of a suitable control DNA, e.g., control DNA of suitable length, to the sample obtained from the transplant recipient prior to DNA extraction or isolation, and calculating an absolute concentration or amount of transplant-derived cell-free DNA based on a standard curve. In some embodiments, determining the status of a transplant may be informative with regard to a clinical decision involving the treatment of a recipient of a transplant, for example, with respect to adjusting the immunosuppressive treatment of the recipient.

Combined Analysis of Gene Expression Levels and Donor-Derived Cell-Free Nucleic Acids Levels The methods of the present disclosure also involve determining expression levels of one or more informative genes in a sample from a recipient of a transplant in combination with determining the amount or levels of transplant-derived cell-free nucleic acids, e.g., transplant-derived cell-free DNA, in a sample from a recipient of a transplant and, ultimately, determining the status of the transplant in the recipient of the transplant. In some embodiments, the status of the transplant in the recipient of the transplant can be determined on the basis of a combined score. In some embodiments, the status of the transplant in the recipient of the transplant can be determined without a combined score. The combined score may be generated by equal weighting of the gene expression score (that is generated by applying a trained classifier to the expression levels of the one or more informative genes) and the amount or levels of transplant-derived cell-free nucleic acids. The combined score may also be generated by unequal weighting of the gene expression score (that is generated by applying a trained classifier to the expression levels of the one or more informative genes) and the amount or levels of transplant-derived cell-free nucleic acids.

The methods of the present disclosure for determining expression levels of one or more informative genes in combination with transplant-derived cell-free DNA levels can be informative with respect to determining the status of a transplant in a recipient, a) based on the presence or absence of a change in immune activity as indicated by the gene expression signature or score, and b) based on the presence or absence of transplant injury, as indicated by the transplant-derived cell-free DNA levels or amounts. Following transplantation of, e.g., an organ, tissue, or cells, the recipient may experience immune quiescence, which is a state that can be characterized by the absence or low levels of immune activity or absence of rejection-associated clinical symptoms, and that can be accompanied by levels of transplant-derived cell-free DNA that are below a cut-off value and not indicative of transplant injury. Alternatively, the recipient may experience active rejection, which may be due to T cell-mediated rejection, antibody-mediated rejection, or a combination of the two (i.e., a "mixed" rejection), and which is a state that can be characterized by a) the presence of immune (re)activity, as determined by a change in gene expression of the one or more informative genes alone, b) the presence of transplant injury, as determined by levels of transplant-derived cell-free DNA alone that are at or above a cut-off value that is indicative of transplant injury, or c) both the presence of immune (re)activity and the presence of transplant injury, as determined by the combined analysis of gene expression changes and transplant-derived cell-free DNA levels. Accordingly, the status of a transplant may be immune quiescence, active rejection, T cell-mediated rejection, antibody-mediated rejection, or mixed rejection. The methods described herein may be used to discriminate between statuses, detect the status of a transplant, or assess the likelihood of a recipient of a transplant experiencing a particular status. In some embodiments, the status of a transplant is informative with regard to the need for adjustment, e.g., increase, decrease, change, or initiation, of the immunosuppressive treatment of a recipient of the transplant. In some embodiments, the status of the transplant enables a clinical decision. Exemplary methods are described in detail below.

Methods of Detecting or Monitoring Immune Quiescence, Using a Combined Analysis of Gene Expression and Transplant Donor-Derived Cell-Free Nucleic Acids In one aspect, the present disclosure provides a method of detecting or monitoring immune quiescence in a transplant recipient based on the combined analysis of gene expression and transplant donor-derived cell-free nucleic acids, e.g., transplant donor-derived cell-free DNA (dd-cfDNA).

In some embodiments, the method of detecting or monitoring immune quiescence comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids. In some embodiments, combined scores being equal to or below a cut-off value indicate that the transplant recipient is likely experiencing immune quiescence. In some embodiments, the method comprises detecting immune quiescence if the combined scores are determined to be equal to or below the cut-off value. In some embodiments, detecting or monitoring immune quiescence may be informative with regard to a clinical decision involving the treatment of a recipient of a transplant, for example, with respect to the need for adjusting, e.g., increasing, decreasing, changing, or initiating, the immunosuppressive treatment of the recipient. Detecting or monitoring immune quiescence may also be informative with regards to a clinical decision involving the need for performing a transplant biopsy. If a transplant recipient is found to experience immune quiescence, a biopsy may not be needed, thereby sparing the recipient an invasive, risky and often inconclusive procedure. In some embodiments, the presence of immune quiescence is informative with regards to the need for adjustment of the treatment of a recipient of the transplant, e.g., by decreasing, changing, or even suspending the immunosuppressive treatment of the recipient.

Methods of Discriminating Between Active Rejection and Immune Quiescence, Using a Combined Analysis of Gene Expression and Transplant Donor-Derived Cell-Free Nucleic Acids In one aspect, the present disclosure provides a method of discriminating between active rejection and immune quiescence in a transplant recipient based on the combined analysis of gene expression and transplant donor-derived cell-free nucleic acids, e.g., transplant donor-derived cell-free DNA (dd-cfDNA).

In some embodiments, the method of discriminating between active rejection and immune quiescence comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids. In some embodiments, combined scores being equal to or above a cut-off value indicate that the transplant recipient is likely experiencing active rejection or is at risk of developing active rejection, and combined scores being below the cut-off value indicate that the transplant recipient is likely experiencing immune quiescence. In some embodiments, the method comprises detecting active rejection or detecting a risk of developing active rejection if the combined scores are determined to be equal to or above the cut-off value. In some embodiments, discriminating between active rejection and immune quiescence may be informative with regard to a clinical decision involving the treatment of a recipient of a transplant, for example, with respect to the need for adjusting, e.g., increasing, decreasing, changing, or initiating, the immunosuppressive treatment of the recipient. Discriminating between active rejection and immune quiescence may also be informative with regard to a clinical decision involving the need for performing a transplant biopsy. If a transplant recipient is found to experience immune quiescence, a biopsy may not be needed, thereby sparing the recipient an invasive, risky, and often inconclusive procedure.

In general, combined scores being equal to or above a suitable cut-off value are informative with regard to whether the transplant recipient experiences active rejection or is at risk of developing active rejection. In some embodiments, the presence of active rejection or the risk of active rejection enables a clinical decision. In some embodiments, the presence of active rejection or the risk of active rejection is informative with regard to the need for adjustment of the treatment of a recipient of the transplant. Combined scores being equal to or below a suitable cut-off value are informative with regard to whether the transplant recipient experiences immune quiescence. In some embodiments, the presence of immune quiescence and lack of injury (combined low score) enables a clinical decision involving the need for performing a transplant biopsy. In some embodiments, the presence of immune quiescence and lack of injury is informative with regard to the need for adjustment of the treatment of a recipient of the transplant.

The methods of the present disclosure for detecting or monitoring for immune quiescence, and for discriminating immune quiescence from allograft rejection, using a combined analysis of gene expression and transplant donor-derived cell-free nucleic acids, e.g., transplant donor-derived cell-free DNA (dd-cfDNA), may be employed for general surveillance of a transplant recipient, for general surveillance of a transplant recipient who shows little or no clinical signs of rejection or who has no clinically indicated need for a biopsy. In some embodiments, the methods for detecting or monitoring for immune quiescence, and for discriminating immune quiescence from allograft rejection, using a combined analysis of gene expression and transplant donor-derived cell-free nucleic acids, e.g., transplant donor-derived cell-free DNA (dd-cfDNA), may be employed for assessment of a transplant recipient who shows clinical signs of rejection or who has a clinically indicated need for a biopsy. In some embodiments, the methods of the present disclosure for detecting or monitoring for immune quiescence, and/or for discriminating immune quiescence from allograft rejection utilize a combined score, correlating the results from the analysis of gene expression and transplant donor-derived cell-free nucleic acids, with or without equal weighting. In some embodiments, the methods of the present disclosure for detecting or monitoring for immune quiescence, and/or for discriminating immune quiescence from allograft rejection do not utilize a combined score, but instead use gene expression signature scores and transplant donor-derived cell-free nucleic acids amounts or levels.

Methods of Discriminating Between T Cell-Mediated Rejection and Antibody-Mediated Rejection, Using a Combined Analysis of Gene Expression and Transplant Donor-Derived Cell-Free Nucleic Acids In one aspect, the present disclosure provides a method of discriminating between T cell-mediated rejection and antibody-mediated rejection in a transplant recipient, based on the combined analysis of gene expression and transplant donor-derived cell-free nucleic acids, e.g., transplant donor-derived cell-free DNA (dd-cfDNA).

In some embodiments, the method of discriminating between T cell-mediated rejection and antibody-mediated rejection comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids.

In some embodiments, combined scores being equal to or above a first cut-off value indicate that the transplant recipient is likely experiencing T cell-mediated rejection or is at risk of developing T cell-mediated rejection, and combined scores being equal to or above a second cut-off value indicate that the transplant recipient is likely experiencing antibody-mediated rejection or is at risk of developing antibody-mediated rejection. In some embodiments, the method comprises detecting T cell-mediated rejection if the combined scores are determined to be equal to or above the first cut-off value and detecting antibody-mediated rejection if the combined scores are determined to be equal to or above the second cut-off value.

In general, combined scores being equal to or above a suitable first cut-off value are informative with regard to a likelihood that the transplant recipient experiences T cell-mediated rejection or is at risk of developing T cell-mediated rejection. Further, in general, combined scores being equal to or above a suitable second cut-off value are informative with regard to a likelihood that the transplant recipient experiences antibody-mediated rejection or is at risk of developing antibody-mediated rejection. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the treatment of a recipient of the transplant. For example, due to the presence of T cell-mediated rejection or the risk of developing T cell-mediated rejection, the treatment of a transplant recipient might be adjusted by administering bolus steroid treatment in addition to or in lieu of the immunosuppressive or anti-rejection treatment that the transplant recipient already received.

In some embodiments, the presence of antibody-mediated rejection or the risk of developing antibody-mediated rejection is informative with regard to the need for adjustment of the treatment of a recipient of the transplant. For example, due to the presence of antibody-mediated rejection or the risk of developing antibody-mediated rejection, the treatment of a transplant recipient might be adjusted by administering intravenous immunoglobulin and/or conducting plasmapheresis in addition to or in lieu of the immunosuppressive or anti-rejection treatment that the transplant recipient already received.

Methods of Discriminating Between Immune Quiescence, T Cell-Mediated Rejection, and Antibody-Mediated Rejection, Using a Combined Analysis of Gene Expression and Transplant Donor-Derived Cell-Free Nucleic Acids In one aspect, the present disclosure provides a method of discriminating between immune quiescence, T cell-mediated rejection, and antibody-mediated rejection in a transplant recipient, based on the combined analysis of gene expression and transplant donor-derived cell-free nucleic acids, e.g., transplant donor-derived cell-free DNA (dd-cfDNA).

In some embodiments, the method of discriminating between immune quiescence, T cell-mediated rejection and antibody-mediated rejection comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids.

In some embodiments, combined scores being equal to or above a first cut-off value indicate that the transplant recipient is likely experiencing T cell-mediated rejection or is at risk of developing T cell-mediated rejection, combined scores being equal to or above a second cut-off value indicate that the transplant recipient is likely experiencing antibody-mediated rejection or is at risk of developing antibody-mediated rejection, and combined scores being below the first and the second cut-off value indicate that the transplant recipient is likely experiencing immune quiescence.

In some embodiments, the method comprises detecting T cell-mediated rejection if the combined scores are determined to be equal to or above the first cut-off value and detecting antibody-mediated rejection if the combined scores are determined to be equal to or above the second cut-off value.

In general, combined scores being equal to or above a suitable first cut-off value are informative with regard to a likelihood that the transplant recipient experiences T cell-mediated rejection or is at risk of developing T cell-mediated rejection. Further, in general, combined scores being equal to or above a suitable second cut-off value are informative with regard to a likelihood that the transplant recipient experiences antibody-mediated rejection or is at risk of developing antibody-mediated rejection. In general, combined scores below the first and the second cut-off values are informative with regard to a likelihood that the transplant recipient experiences immune quiescence. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the treatment of a recipient of the transplant. For example, due to the presence of T cell-mediated rejection or the risk of developing T cell-mediated rejection, the treatment of a transplant recipient might be adjusted by administering bolus steroid treatment in addition to or in lieu of the immunosuppressive or anti-rejection treatment that the transplant recipient already received.

In some embodiments, the presence of antibody-mediated rejection or the risk of developing antibody-mediated rejection is informative with regard to the adjustment of the treatment of a recipient of the transplant. For example, due to the presence of antibody-mediated rejection or the risk of developing antibody-mediated rejection, the treatment of a transplant recipient might be adjusted by administering intravenous immunoglobulin and/or conducting plasmapheresis in addition to or in lieu of the immunosuppressive or anti-rejection treatment that the transplant recipient already received. In some embodiments, the presence of immune quiescence enables a clinical decision. In some embodiments, the presence of immune quiescence is informative with regard to the need for adjustment of the treatment of a recipient of the transplant.

Methods of Detecting, Monitoring, and/or Guiding Treatment of Active Rejection, Using a Combined Analysis of Gene Expression and Transplant Donor-Derived Cell-Free Nucleic Acids In one aspect, the present disclosure provides a method of detecting, monitoring, and/or guiding treatment of active rejection in a transplant recipient, based on the combined analysis of gene expression and transplant donor-derived cell-free nucleic acids, e.g., transplant donor-derived cell-free DNA (dd-cfDNA).

In some embodiments, the method of detecting, monitoring, and/or guiding treatment of active rejection comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids.

In some embodiments, combined scores equal to or above a cut-off value indicate that the transplant recipient is likely experiencing active rejection or is at risk of developing active rejection. In some embodiments, the method comprises detecting active rejection if the combined scores are determined to be equal to or above the cut-off value. In some embodiments, the method further comprises treating the rejection, or risk thereof, by administering to the recipient an immunosuppressive agent, bolus steroid treatment, intravenous immunoglobulin, plasmapheresis and/or increasing the dosage of an immunosuppressive or anti-rejection agent that the recipient already received.

In general, combined scores equal to or above a cut-off value are informative with regard to a likelihood that the transplant recipient experiences active rejection or is at risk of developing active rejection. In some embodiments, the presence of active rejection or the risk of developing active rejection enables a clinical decision. In some embodiments, the presence of active rejection or the risk of developing active rejection is informative with regard to the adjustment of the immunosuppressive treatment of a recipient of the transplant. In some embodiments, the presence of active rejection indicates a need to administer to the recipient an immunosuppressive or anti-rejection agent, bolus steroid treatment, intravenous immunoglobulin, plasmapheresis and/or increase the dosage of an immunosuppressive or anti-rejection agent that the recipient already received. In some embodiments, the presence of active rejection indicates a need to monitor the recipient of the transplant more frequently.

Methods of Detecting and Distinguishing T Cell-Mediated Rejection from Antibody Mediated Rejection, Using a Combined Analysis of Gene Expression and Transplant Donor-Derived Cell-Free Nucleic Acids In one aspect, the present disclosure provides a method of detecting and distinguishing T cell-mediated rejection from antibody mediated rejection in a transplant recipient, based on the combined analysis of gene expression and transplant donor-derived cell-free nucleic acids, e.g., transplant donor-derived cell-free DNA (dd-cfDNA).

In some embodiments, the method of detecting and distinguishing T cell-mediated rejection from antibody mediated rejection comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally, generating a combined score by correlating the gene expression score and the amount or levels of transplant-derived cell-free nucleic acids.

In some embodiments, combined scores equal to or above a cut-off value indicate that the transplant recipient is likely experiencing T cell-mediated rejection or is at risk of developing T cell-mediated rejection. In some embodiments, the method comprises detecting T cell mediated rejection if the combined scores are determined to be equal to or above the cut-off value. In some embodiments, the method further comprises treating the rejection by administering to the recipient an immunosuppressive or anti-rejection agent or bolus steroid treatment and/or increasing the dosage of an immunosuppressive or anti-rejection agent that the recipient already received.

In general, combined scores equal to or above a suitable first cut-off value are informative with regard to a likelihood that the transplant recipient experiences T cell-mediated rejection or is at risk of developing T cell-mediated rejection. Further, in general, combined scores equal to or above a suitable second cut-off value are informative with regard to a likelihood that the transplant recipient experiences antibody-mediated rejection or is at risk of developing antibody-mediated rejection. In some embodiments, the presence of T cell-mediated rejection or the risk of developing T cell-mediated rejection enables a clinical decision. In some embodiments, the presence of antibody-mediated rejection or the risk of developing antibody-mediated rejection enables a clinical decision. In some embodiments, the presence of T cell-mediated rejection or the risk of developing T cell-mediated rejection is informative with regard to the adjustment of the immunosuppressive treatment of a recipient of the transplant. In some embodiments, the presence of antibody-mediated rejection or the risk of developing antibody-mediated rejection is informative with regard to the adjustment of the immunosuppressive treatment of a recipient of the transplant.

Methods of Discriminating Between Immune Quiescence and a State of Immune Activation, Using a Combined Analysis of Gene Expression and Transplant Donor-Derived Cell-Free Nucleic Acids In one aspect, the present disclosure provides a method of discriminating between immune quiescence and a state of immune activation caused by infection in a transplant recipient, based on the combined analysis of gene expression and transplant donor-derived cell-free nucleic acids, e.g., transplant donor-derived cell-free DNA (dd-cfDNA).

In some embodiments, the method of discriminating between immune quiescence and a state of immune activation comprises providing nucleic acids from a first sample obtained from the transplant recipient, and providing nucleic acids from the same first sample or from a second sample obtained from the transplant recipient comprising cell-free nucleic acids that are derived from the transplant and cell-free nucleic acids that are derived from the recipient. In some embodiments, the method comprises determining expression levels of one or more genes associated with an immune response-regulating pathway of inflammation, corticosteroid sensitivity, and/or T cell activation, as described earlier, and determining an amount or levels of transplant-derived cell-free nucleic acids. In some embodiments, the method comprises generating a gene expression score by applying a trained classifier to the expression levels of the one or more genes, and, optionally. generating a combined score by correlating the gene expression score and the amount or levels of transplant-derived cell-free nucleic acids.

In some embodiments, combined scores being equal to or above a cut-off value indicate that the transplant recipient likely experiences a state of immune activation or is at risk of developing a state of immune activation. In some embodiment, combined scores being equal to or above a cut-off value indicate that the transplant recipient likely experiences a state of immune activation caused by infection or is at risk of developing a state of immune activation caused by infection. In some embodiments, discriminating between immune quiescence and a state of immune activation caused by infection in a transplant recipient may be informative with regard to a clinical decision involving the continued treatment of a recipient of a transplant, for example, with respect to the need for adjusting, e.g., increasing, decreasing, changing the immunosuppressive treatment of the recipient, or initiating anti-infective therapy. Discriminating between immune quiescence and a state of immune activation caused by infection in a transplant recipient may also be informative with regard to a clinical decision involving the need for performing a transplant biopsy.

Combined scores equal to or above a cut-off value may occur in case of infection with infectious agents, e.g., viruses such as Cytomegalovirus, Epstein-Barr virus, Anelloviridae, and BK virus; bacteria such as *Pseudomonas aeruginosa*, Enterobacteriaceae, *Nocardia, Streptococcus pneumonia, Staphyloccous aureus*, and *Legionella*; fungi such as *Candida, Aspergillus, Cryptococcus, Pneumocystis carinii*; or parasites such as *Toxoplasma gondii*. If, upon testing for the presence and/or levels of such infectious agents, infection with one or more infectious agents is confirmed, immunosuppressive therapies may be decreased, increased, maintained or modified with respect to dosage and/or immunosuppressive agent(s), and anti-infective therapy may be initiated.

Guiding and/or Adjusting Treatment of the Recipient of a Transplant

The methods of the present disclosure can be used to inform the need to adjust immunosuppressive therapy being administered to the recipient of the transplant. In general, identifying a status of active rejection, e.g., T cell-mediated rejection, antibody-mediated rejection, or mixed T cell-mediated and antibody-mediated rejection, or immune quiescence in the recipient is informative with regard to guiding treatment and/or determining a need to adjust immunosuppressive therapy being administered to the recipient of the transplant. In some embodiments, determining the status of the transplant, as described above, is informative with regard to determining a need to adjust immunosuppressive therapy being administered to the recipient of a transplant. In some embodiments, determining the status of the transplant is informative with regard to determining the way in which immunosuppressive therapy should be adjusted. In some embodiments, determining the status of the transplant is informative with regard to determining adherence to or compliance with the prescribed (immunosuppressive) medication regimen.

It is to be understood that immunosuppressive therapies of the present disclosure may be administered in a number of ways, including intravenously, intramuscularly, subcutaneously, intrathecally, or orally. The route of therapy will depend on the type of therapy that is being administered. Appropriate routes of therapy for immunosuppressive and anti-rejection therapy, and other transplant-related therapies will be evident to one of skill in the art.

Guiding Immunosuppressive Treatment, Informing, Providing Information

The methods of the present disclosure for determining the status of a transplant in a recipient of a transplant can be used to guide immunosuppressive treatment of a transplant recipient. In general, identifying a status of immune quiescence or active rejection, e.g., T cell-mediated rejection, antibody-mediated rejection, or mixed T cell-mediated and antibody-mediated rejection, in the recipient is informative with regard to guiding immunosuppressive treatment of the transplant recipient. For example, improved methods of detecting and monitoring immune quiescence and improved methods of discriminating between immune quiescence and active rejection based on combined scores, as described herein, will improve transplant recipient care management, e.g., by using lower drug concentrations or less frequent dosing schedules, which in turn will benefit the transplant recipients by lowering the incidence of opportunistic infections and cancer.

Immune quiescence, based on a gene expression score or a combined score, below a cut-off value may indicate an opportunity to reduce maintenance immunosuppression and/or to forgo a biopsy, thereby sparing the transplant recipient an invasive, risky and often inconclusive procedure. A gene expression score or a combined score above a cut-off value may indicate a need to increase the dose or frequency of immunosuppression treatment, or a need to change to a different class or type of immunosuppressive agent(s). After treatment for a diagnosed episode of rejection, gene expression scores and combined scores inform on the return to normal levels of both gene expression and transplant donor-derived cell-free DNA (dd-cfDNA). Monitoring gene expression of informative genes and dd-cfDNA levels can indicate whether an increase or decrease of immunosuppressive treatment is warranted, and may indicate that a new 'set point' is needed for a particular transplant recipient. For example, the transplant recipient may have been on a regimen of low levels of immunosuppression, but after the detection of likely or actual graft rejection the recipient is at higher risk and therefore a new set point for immunosuppressive maintenance therapy is found and monitored.

Gene expression signature scores and combined scores can inform on immune quiescence as an indicator of a lack of adherence to immunosuppressive treatment or medication regimens. If the gene expression signature scores and/or combined scores are determined to be equal to or above a cut-off value, it may indicate that the patient has stopped or reduced the dose of the immunosuppressive medications and/or reduced the frequency of dosing. For example, monitoring a transplant recipient over a period of time, e.g., over a series of surveillance visits, while the immune system is in a quiescent state would establish an expected range of immune quiescence for the transplant recipient. Elevated gene expression signature scores and/or combined scores deviating from the expected range would indicate a lack of quiescence, potentially due to a lapse in adherence to the prescribed immunosuppressive regimen.

Elevated scores indicating a lack of quiescence may also occur in case of infection with infectious agents, e.g., viruses such as Cytomegalovirus, Epstein-Barr virus, Anelloviridae, and BK virus; bacteria such as *Pseudomonas aeruginosa*, Enterobacteriaceae, *Nocardia, Streptococcus pneumonia, Staphyloccous aureus*, and *Legionella*; fungi such as *Candida, Aspergillus, Cryptococcus, Pneumocystis carinii*; or parasites such as *Toxoplasma gondii*. If, upon testing for the presence and/or levels of such infectious agents, infection with one or more infectious agents is confirmed, immunosuppressive therapies may be decreased, increased, maintained or modified with respect to dosage and/or immunosuppressive agent(s).

Adjusting Immunosuppressive Therapy

The methods of the present disclosure for determining the status of a transplant in a recipient of a transplant can be used to inform the need to adjust immunosuppressive therapy being administered to the recipient of the transplant. In general, identifying a status of active rejection, e.g., T cell-mediated rejection, antibody-mediated rejection, or mixed T cell-mediated and antibody-mediated rejection, or immune quiescence in the recipient is informative with regard to determining a need to adjust immunosuppressive therapy being administered to the recipient of transplant.

Immunosuppressive therapy generally refers to the administration of an immunosuppressant or other therapeutic agent that suppresses immune responses to a subject. Exemplary immunosuppressant agents may include, but are not limited to, calcineurin inhibitors, mTor inhibitors, ACE inhibitors, anticoagulants, antimalarials, β-blockers, corticosteroids, cardiovascular drugs, non-steroidal anti-inflammatory drugs (NSAIDs), and steroids including, for example, aspirin, azathioprine, B7RP-1-fc, brequinar sodium, campath-1H, celecoxib, chloroquine, coumadin, cyclophosphamide, cyclosporin A, DHEA, deoxyspergualin, dexamethasone, diclofenac, dolobid, etodolac, everolimus, FK778, feldene, fenoprofen, flurbiprofen, heparin, hydralazine, hydroxychloroquine, CTLA-4 or LFA3 immunoglobulin, ibuprofen, indomethacin, ISAtx-247, ketoprofen, ketorolac, leflunomide, meclophenamate, mefenamic acid, mepacrine, 6-mercaptopurine, meloxicam, methotrexate, mizoribine, mycophenolic acid derivatives, naproxen, oxaprozin, Plaquenil, NOX-100, prednisone, methylprednisolone, rapamycin (sirolimus), sulindac, tacrolimus (FK506), thymoglobulin, tolmetin, tresperimus, U0126, as well as antibodies including, for example, alpha lymphocyte antibodies, adalimumab, anti-CD3, anti-CD25, anti-CD52 anti-IL2R, anti-TAC antibodies, basiliximab, daclizumab, etanercept, hu5C8, infliximab, OKT4, and natalizumab, or any combination thereof. Immunosuppressive therapy may be adjusted in response to the identification of immune quiescence, ABMR, TCMR, or mixed rejection. For example, in response to the identification of TCMR, bolus steroid treatment may be initiated or maintenance immunosuppressive therapy may be increased with respect to dosage and/or frequency. In response to the identification of ABMR, for example, plasmapheresis or intravenous immunoglobulin (IVIg) may be initiated.

Adjusting in Response to Identification of a Status of Active Rejection in the Transplant Recipient In some embodiments, a status of active rejection e.g., TCMR, ABMR, or mixed TCMR/ABMR is indicative of a need to initiate, adjust, continue, or increase administration of an immunosuppressive therapy being administered to the transplant recipient. In some embodiments in which the recipient is experiencing active rejection, immunosuppressive therapy being administered to the recipient is initiated, adjusted, continued, or increased.

Adjusting, continuing, or increasing administration of the immunosuppressive therapy may be performed over a variety of time intervals, dosages, and/or dosage rates. In some embodiments, adjusting, continuing, or increasing immunosuppressive therapy may involve administration of the same dosage, the same dosage rate, a higher dosage, and/or a higher dosage rate compared to the dosage or dosage rate of the immunosuppressive therapy previously administered to the transplant recipient. In some embodiments, continuing administration of the immunosuppressive therapy involves administering the same total dosage of immunosuppressive therapy to the recipient for the same amount of time. In some embodiments, continuing administration of the immunosuppressive therapy involves administering the same total dosage of immunosuppressive therapy to the recipient for a shorter period of time (i.e., a higher dosage rate). In some embodiments, continuing administration of the immunosuppressive therapy involves administering a higher dosage of immunosuppressive therapy to the recipient for the same amount of time. In some embodiments, continuing administration of the immunosuppressive therapy involves administering a higher dosage of immunosuppressive therapy to the recipient for a longer period of time.

Increasing administration of the immunosuppressive therapy may be performed over a variety of time intervals, dosages, and/or dosage rates, as long as the total dosage and/or dosage rate is increased compared to the dosage or dosage rate of immunosuppressive therapy previously administered to the recipient. In some embodiments, increasing administration of the immunosuppressive therapy involves administering the same total dosage of immunosuppressive therapy to the recipient for a shorter period of time (i.e., a higher dosage rate). In some embodiments, increasing administration of the immunosuppressive therapy involves administering a higher dosage of immunosuppressive therapy to the recipient for the same amount of time. In some embodiments, increasing administration of the immunosuppressive therapy involves administering a higher dosage of immunosuppressive therapy to the recipient for a longer period of time. In some embodiments where the transplant recipient is not receiving immunosuppressive therapy, the methods of the present disclosure may indicate a need to begin administering immunosuppressive therapy to the transplant recipient.

In some embodiments where immunosuppressive therapy was previously administered to the transplant recipient, adjustment of immunosuppressive therapy includes changing the type or form of the immunosuppressive therapy being administered to the recipient. The new type or form of immunosuppressive therapy may include any number of immunosuppressive therapies known in the art, such as the immunosuppressive therapies described above. Furthermore, the dosage, dosage rate, and timing of immunosuppressive therapy administration may or may not vary compared to those of the previously administered immunosuppressive therapy. Furthermore, immunosuppressive therapies could be increased from a low dose to a moderate or high dose upon diagnosis of active rejection. Alternatively, the immunosuppressive therapy could be changed to a different treatment or a different type (class) of treatments. For instance, everolimus may be stopped in favor of belatacept. Another treatment approach in response to active rejection could be the change from one to another drug within the same class, for example discontinuing cyclosporine while beginning treatment with mycophenolic acid derivatives.

Adjusting in Response to Identification of a Status of Immune Quiescence

In some embodiments, a status of immune quiescence is indicative of a need to adjust, reduce, or discontinue immunosuppressive therapy being administered to the transplant recipient. In some embodiments in which the transplant recipient is experiencing immune quiescence, immunosuppressive therapy being administered to the recipient is adjusted, reduced, or discontinued.

Reducing administration of the immunosuppressive therapy may be performed over a variety of time intervals, dosages, and/or dosage rates, as long as the total dosage and/or dosage rate is reduced compared to the dosage or dosage rate of immunosuppressive therapy previously administered to the recipient. In some embodiments, reducing immunosuppressive therapy may involve administering the same total dosage of immunosuppressive therapy to the recipient for a longer period of time (i.e., a lower dosage rate). In some embodiments, reducing immunosuppressive therapy may involve administering a lower dosage of immunosuppressive therapy to the recipient for the same amount of time. In some embodiments, reducing immunosuppressive therapy may involve administering a lower dosage of immunosuppressive therapy to the recipient for a shorter period of time. In some embodiments where the transplant recipient is receiving immunosuppressive therapy, the methods of the present disclosure may indicate a need to discontinue immunosuppressive therapy in the transplant recipient.

In some embodiments where immunosuppressive therapy was previously administered to the transplant recipient, adjustment of immunosuppressive therapy includes changing the type or form of the immunosuppressive therapy being administered to the recipient. The new type or form of immunosuppressive therapy may include any number of immunosuppressive therapies known in the art, such as the immunosuppressive therapies described above. Furthermore, the dosage, dosage rate, and timing of immunosuppressive therapy administration may or may not vary compared to those of the previously administered immunosuppressive therapy.

Adjusting Transplant-Related Therapies

The methods of the present disclosure for determining the status of a transplant in a recipient of a transplant can be used to inform the need to adjust other transplant-related therapies being administered to the transplant recipient. In general, identifying a status of active rejection, e.g., T cell-mediated rejection, antibody-mediated rejection, or mixed T cell-mediated or antibody-mediated rejection, or immune quiescence in the recipient is informative with regard to determining a need to adjust other transplant-related therapies being administered to the transplant recipient.

Other transplant-related therapies include treatments or therapies besides transplantation or immunosuppressive therapy that are administered to a recipient of a transplant to promote survival of the transplant or to treat transplant-related symptoms (e.g., cytokine release syndrome, neurotoxicity). Examples of other transplant-related therapies include but are not limited to administration of antibodies, antigen-targeting ligands, non-immunosuppressive drugs, and other agents that stabilize or destabilize components of transplants that are critical to transplant activity or that directly activate or inhibit one or more transplant activity. These activities may include the ability to induce an immune response, recognize particular antigens, replicate, and/or induce repair of damaged tissues. Adjusting immunosuppressive therapy may be combined with adjusting, initiating, or discontinuing other transplant-related therapies. Treatments for TCMR include intravenous steroid infusions and T cell depletion (i.e., with rATG), while treatments commonly used for ABMR include plasma exchange, intravenous Ig, bortezomib, Eculizumab, C1-INH, and rituximab.

Adjusting Monitoring of a Transplant Recipient

The methods of the present disclosure for determining the status of a transplant in a recipient of a transplant can be used to inform the need to adjust monitoring of the recipient of the transplant. In general, identifying a status of active rejection, e.g., T cell-mediated rejection, antibody-mediated rejection, or mixed T cell-mediated/antibody-mediated rejection, or immune quiescence in the recipient is informative with regard to determining a need to adjust monitoring of a recipient of a transplant. In some embodiments, determining the status of the transplant, as described above, is informative with regard to determining a need to adjust monitoring of a recipient of a transplant.

Depending on the status of the transplant, monitoring of the recipient may be adjusted accordingly. For example, monitoring may be adjusted by increasing or decreasing the frequency of monitoring, as appropriate. Monitoring may be adjusted by altering the means of monitoring, for example, by altering the metric or assay that is used to monitor the recipient.

Kits

Also provided herein are kits for use in any one of the methods described herein.

In one aspect, provided herein is a kit for classifying immune quiescence or transplant rejection based on gene expression signature(s), the kit comprising in one or more separate containers a set of primers specific for at least three genes selected from the group consisting of DCAF12, FLT3, IL1R2, PDCD1, and MARCH8.

In some embodiments, the kit further includes reagents for use in accordance with a method of the present disclosure. For example, in some embodiments, the kit includes reagents for analyzing nucleic acids isolated from a recipient of a transplant, as described herein. In some embodiments in which expression levels are determined by analyzing RNA from a sample from the transplant recipient, the kit may comprise reagents for performing qPCR, or RNA-sequencing. In some embodiments, the kit may comprise reagents sufficient to analyze a single sample. In some embodiments, the kit may comprise reagents sufficient to analyze several samples.

In some embodiments, the kit may include instructions to specify target values and control materials that may be used in conjunction with the reagents and instructions provided in the kit. In some embodiments, the kit further includes controls for use in accordance with a method of the present disclosure. For example, in some embodiments the kit further comprises primers specific for a suitable reference gene as described herein.

In some embodiments, the kit further includes instructions for use in accordance with a method of the present disclosure. Instructions for performing any one of the methods described herein may be included.

In some embodiments, the kit further includes instructions and specifications for input material quality or input preparation methods.

In some embodiments, the kit comprises software instructions for analysis of sequence or PCR data. In some embodiments, the kit further comprises software instructions for statistical analysis of gene expression signatures.

In some embodiments, the kit may be used in conjunction with kits for measurement of dd-cfDNA.

In some embodiments, the kit further comprises reagents, controls, instructions for use, software instructions for analysis of transplant-derived cell-free nucleic acids, and instructions for generating combined scores from gene expression signature scores and levels of transplant-derived cell-free nucleic acids.

Computer Implementation

Any of the methods described above can be implemented and performed by a computer program product that comprises a computer executable logic recorded on a computer-readable or machine-readable medium. The computer program can execute some or all of the methods described herein, such as: i) providing nucleic acids from a first sample obtained from the transplant recipient, ii) determining expression levels of one or more genes associated with an immune response-regulating pathway of inflammation, corticosteroid sensitivity, and/or T cell activation, iii) generating a gene expression score by applying a trained classifier to the expression levels of the one or more genes, wherein the gene expression score being equal to or below a cut-off value indicates that the transplant recipient is likely experiencing immune quiescence, and iv) detecting immune quiescence if the gene expression score is determined to be equal to or below the cut-off value, or detecting transplant rejection if the gene expression score is determined to be equal or above the cut-off value. Or such as: (i) providing nucleic acids from a first sample obtained from the transplant recipient comprising RNA, and providing nucleic acids from a second sample obtained from the transplant recipient comprising cell-free nucleic acids that are derived from the transplant and cell-free nucleic acids that are derived from the recipient, (ii) determining expression levels of one or more genes associated with an immune response-regulating pathway of inflammation, corticosteroid sensitivity, and/or T cell activation in the first sample and determining an amount or levels of transplant-derived cell-free nucleic acids in the second sample, (iii) generating a gene expression score by applying a trained classifier to the expression levels of the one or more genes, (iv) generating a combined score by correlating the gene expression score and the amount or levels of transplant-derived cell-free nucleic acids, wherein the combined score being equal to or below a cut-off value indicates that the transplant recipient is likely experiencing immune quiescence and wherein the combined score being equal to or above a cut-off value indicates that the transplant recipient is likely experiencing active rejection, and (v) detecting immune quiescence if the combined score is determined to be equal to or below the cut-off value, or detecting active rejection if the combined score being equal to or above a cut-off value indicates that the transplant recipient is likely experiencing active rejection The computer executable logic can work in any computer that may be any of a variety of types of general-purpose computers such as a personal computer, network server, workstation, or other computer platform now or later developed. In some embodiments, a computer program product comprises a computer usable medium having the computer executable logic (computer software program, including program code) stored therein. The computer executable logic can be executed by a processor, causing the processor to perform some or all of the methods described herein. In other embodiments, some functions are implemented primarily in hardware. Implementation of the hardware as to perform the functions described herein will be apparent to those skilled in the relevant arts. In some embodiments, the machine-readable medium comprises a set of instructions recorded thereon to cause a computer to perform the steps of (i) providing nucleic acids from a first sample obtained from the transplant recipient, ii) determining expression levels of one or more genes associated with an immune response-regulating pathway of inflammation, corticosteroid sensitivity, and/or T cell activation, iii) generating a gene expression score by applying a trained classifier to the expression levels of the one or more genes, wherein the gene expression score being equal to or below a cut-off value indicates that the transplant recipient is likely experiencing immune quiescence or wherein the gene expression score being equal to or above a cut-off value indicates that the transplant recipient is likely experiencing active rejection, and iv) detecting immune quiescence if the gene expression score is determined to be equal to or below the cut-off value, or detecting active rejection if the gene expression score is determined to be equal or above the cut-off value. In some embodiments, the computer readable medium comprises a set of instructions recorded thereon to cause a computer to perform the steps of (i) providing nucleic acids from a first sample obtained from the transplant recipient comprising RNA, and providing nucleic acids from a second sample obtained from the transplant recipient comprising cell-free nucleic acids that are derived from the transplant and cell-free nucleic acids that are derived from the recipient, (ii) determining expression levels of one or more genes associated with an immune response-regulating pathway of inflammation, corticosteroid sensitivity, and/or T cell activation in the first sample and determining an amount or levels of transplant-derived cell-free nucleic acids in the second sample, (iii) generating a gene expression score by applying a trained classifier to the expression levels of the one or more genes, (iv) generating a combined score by correlating the gene expression score and the amount or levels of transplant-derived cell-free nucleic acids, wherein the combined score being equal to or below a cut-off value indicates that the transplant recipient is likely experiencing immune quiescence and wherein the combined score being equal to or above a cut-off value indicates that the transplant recipient is likely experiencing active rejection, and (v) detecting immune quiescence if the combined score is determined to be equal to or below the cut-off value, or detecting active rejection if the combined score being equal to or above a cut-off value indicates that the transplant recipient is likely experiencing active rejection.

EXAMPLES

The following examples are put forth to provide those of ordinary skill in the art with a complete description of how to make and use the methods and kits of the disclosure. Modifications to the examples described herein will be readily apparent to those of ordinary skill in the art, and the general principles described herein may be applied to other examples and applications without departing from the scope of the embodiments presented herein.

Example 1. Gene Expression Profiling Discriminates Rejection from Immune Quiescence in Renal Transplant Recipients Purpose: Assessment of immune activation is important when considering pathologies such as allograft rejection as well as potential interventions that may extend allograft survival. Optimizing interventions by assessing impact through quantifiable measures such as biomarker changes can drive the paradigm shift from reactive to proactive care. Here, validation of a blood gene expression profile (GEP) to inform on T cell-mediated (TCMR), antibody-mediated (ABMR) rejection and mixed rejections is described.

Methods: A classifier using 5 informative genes (DCAF12, FLT3, IL1R2, PDCD1, and MARCH8) was developed to discriminate quiescence from rejection using 21 samples from healthy, stable transplant recipients (HS, no clinical signs or symptoms, and very low level of donor-derived cell free DNA, a marker for organ injury) and 18 active rejection samples from the DART study (ClinicalTrials.gov Identifier NCT02424227) kidney transplant recipients. The gene expression classifier was validated in an independent set of samples from the DART study using targeted RNA sequencing. The validation samples comprised 45 non-rejection (NR, negative for-cause biopsy); 28 quiescent (Q, negative protocol biopsy); 27 HS; 7 T cell-mediated rejection (TCMR), 10 antibody-mediated rejection (ABMR), and 1 mixed TCMR/ABMR rejection. In addition to the determination of the 5-gene expression signature, an AlioSure® assessment of donor-derived cell free DNA (dd-cfDNA) was also performed.

Results: Gene expression signature scores (range 0-20) were significantly different between the control groups (Q, NR, HS) and rejection groups (ABMR, TCMR, Combined or mixed Rejections) (FIG. 1). Median (IQR) results: Q=8.77 (7.52-11.11), NR=10.12 (8.15-12.17), HS=9.45 (8.26-11.55), ABMR=11.50 (10.84-13.15), TCMR=15.14 (12.93-16.69). The scores of the combined rejection group were statistically significant from that of both the NR ($p=0.0003$, 2-tailed t test) and Q groups ($p=0.0001$, 2-tailed t test); and the receiver operating characteristic (ROC) analysis demonstrated an AUC of 0.77 (95% CI 0.70-0.84) and 0.81 (95% CI 0.74-0.88), respectively. Sub-group assessment of the TCMR results showed that higher grade rejection samples have generally higher gene expression signature scores.

Conclusions: Validation of the 5-gene expression signature provides a strong indication of the ability to distinguish graft rejections from immune quiescence. Quantification across a range of scores allows dynamic assessment compared to binary outputs and supports the applicability previously observed for a gene-expression based test in heart transplantation. The gene expression signature scores have a strong association with TCMR and also identify ABMR. The performance suggests a complementary use with AlioSure® to determine donor derived-cell free DNA, combining immunological assessment with informative data on allograft injury.

Example 2: Clinical Validation of an Immune Quiescence Gene Expression Signature to Identify Rejection in Kidney Transplantation Despite the advances of immune suppression therapy, kidney allograft rejection and other forms of injury remain a significant clinical concern, particularly with regards to long-term allograft survival. Evaluation of the immune system can inform on rejection status and help guide interventions that may extend allograft life. Here, the validation of a blood gene expression signature or gene expression profile (GEP) to inform on immune quiescence, T cell-mediated rejection (TCMR) and antibody-mediated rejection (ABMR) is described.

As described herein, a classifier using 5 informative genes (DKAF12, MARCH8, FLT3, IL1R2, and PDCD1) was developed on 56 peripheral blood samples and validated in two independent sets of samples. The primary validation set comprised 98 quiescence samples (negative biopsy; or healthy stable without biopsy) and 18 rejection samples (7 T cell-mediated rejection (TCMR), 10 antibody-mediated rejection (ABMR), and 1 mixed rejection). The second validation set included eight negative biopsy, seven TCMR, two ABMR, and two mixed TCMR/ABMR samples. Donor-derived cell-free DNA (dd-cfDNA) levels were also determined using AlioSure®.

In the primary (DART) validation set, the gene expression classifier scores differed significantly between the quiescence group and the rejection group, $p<0.001$ (Median scores: Q=9.49, ABMR=11.48, TCMR=15.09). In the second validation set, the groups were again statistically different ($p=0.028$), and the medians were similar to the medians from the first validation set. Receiver operating characteristic (ROC) analysis demonstrated an AUC of 0.786 for the DART validation set and 0.800 for the second validation set. The gene expression signature scores were not significantly correlated with the scores derived from dd-cf DNA levels, although both were elevated in rejection. The ability to discriminate rejection from quiescence was improved when the gene expression signature scores and the scores derived from dd-cf DNA levels were used together in a combined score (AUC 0.894).

Validation of a 5-gene expression signature demonstrates a clear differentiation between rejection and immune quiescence, and provides a range of quantified gene expression signature scores. Additionally, both the biological mechanisms and diagnostic performance suggest that assessment of immunological activity using the 5-gene expression signature is complementary to the informative data on allograft injury derived from dd-cfDNA levels using AlioSure®. Together, these insights on immunological activity as well as allograft injury offer a more comprehensive assessment of the quiescent state of transplant recipients.

INTRODUCTION

Despite current implementation of immune suppression regimens, kidney allograft rejection continues to be both a common occurrence and the primary driver of unacceptably high long-term graft failure rates (Mas V. R. et al., *Expert Rev Mol Diagn.* 2011 March; 11(2):183-96; Lo D. J. et al., *Nat Rev Nephrol.* 2014 April; 10(4):215-25; Bontha S. V. et al., *Am J Transplant.* 2017 January; 17(1):11-21). Ten percent of kidney transplant recipients experience allograft rejection in the first year post transplant (Hart A. et al., *Am J Transplant.* 2018 January; 18 Suppl 1(Suppl 1):18-113). Although biopsy is the current standard for diagnosis of rejection, optimizing the appropriateness of biopsies by non-invasive techniques is critical due to the invasive nature of the procedure and the associated risk, as well as the sampling error and subjective nature of histopathologic interpretation. Analysis of large series of renal transplant protocol biopsies demonstrate a 1.9% major complication rate and a 4.7% risk of gross hematuria (Morgan T. A. et al., *Am J Transplant.* 2016 April; 16(4):1298-305; Reschen M. E. et al., *Ann Med Surg* (*Lond*). 2018 February 9; 28:6-10). Additionally, up to 15% of biopsies yield an inadequate specimen, exposing patients to a procedural risk without a diagnostic benefit (Plattner B. W. et al., *J Vasc Access.* 2018 May; 19(3):291-296). The ability to identify the timepoints at which a tissue diagnosis is most valuable could meaningfully improve post-transplant care. In addition, methods for assessing response to rejection treatment and return to baseline allograft function frequently rely on additional follow-up biopsies, all associated with risks, expense, inconvenience, and diagnostic failure.

Serum creatinine levels are commonly used to assess kidney function as a screening test for allograft rejection. However, allograft damage sufficient to impair renal function is often irreversible (Cravedi P. and R. B. Mannon, *Expert Rev Clin Immunol.* 2009 Sep. 1; 5(5): 535-546), and serum creatinine has repeatedly been shown to be a poorly sensitive or specific indicator of rejection (Bloom, R. D. et al., *J Am Soc Nephrol.* 2017 July; 28(7):2221-2232). Robust diagnostic and prognostic biomarkers that provide evidence of graft rejection ahead of pathological findings are needed to help guide clinical management of transplant recipients. Among the best studied advanced biomarkers in transplantation is the use of plasma levels of donor-derived cell-free DNA (dd-cfDNA) to assess allograft injury (Bloom, R. D. et al., *J Am Soc Nephrol.* 2017 July; 28(7):2221-2232). dd-cfDNA has gained significant adoption since it became available as a clinically validated test (Grskovic, M. et al., *J Mol Diagn.* 2016 November; 18(6):890-902), with numerous descriptions of clinical utility (Jordan, S. et al., *Transplant Direct* 2018; 4:e379; Stites, E. et al., *Am J Transplant.* 2020 September; 20(9):2491-2498; Xie, W. Y. et al., *Transplant Direct.* 2021 Mar. 5; 7(4):e679; Wolf-Doty, T. K. et al., *Kidney* 360. 2021 April; 2(4):729-736; Mamlouk O. et al., *Blood.* 2021 May 6; 137(18):2558-2562). An example of a broadly integrated gene expression profile assay that has stood the test of time is AlloMap, available as a surveillance tool for heart transplant recipients since validation in 2005 (Deng, M. C. et al., *Am J Transplant.* 2006 January; 6(1): 150-60). The assay methodology has not changed since its original clinical validation, and therefore the clinical utility remains as published in 2010 (Pham, M. X. et al, *N Engl J Med* 2010; 362(20):1890-1900); the high negative predictive value (NPV) has enabled avoidance of biopsies for over 15 years for the heart transplant community (Deng, M. C. et al, *Clin Transplant.* 2017 March; 31(3)).

Gene expression profiling of the immune system in kidney transplantation, however, has been elusive as a consistently reliable and reproducible measure of rejection. Several plasma gene expression panels have been published (Li, L. et al., *Am J Transplant.* 2012 October; 12(10):2710-8; Kurian, S. M. et al., *Am J Transplant.* 2014 May; 14(5): 1164-72; Van Loon, E. et al., *EBioMedicine* 2019; 46: 463-472). Initial gene association with rejection and composition of multi-gene panels resulted in tests commercially available for clinical use, one of which is applied specifically in place of protocol biopsy (Kurian, S. M. et al, *Am J Transplant.* 2014; 14(5):1164-72). Another has faced challenges from independent studies unable to replicate the validation (Van Loon, E. et al, *Am J Transplant.* 2021; 21(2): 740-750). Other signatures with a strong association with fibrosis (Zhang, W. et al, *J Am Soc Nephrol.* 2019 August; 30(8):1481-1494) or specific to ABMR (Van Loon, E. et al, *EBioMedicine* 2019; 46: 463-472) have not yet achieved routine clinical use.

A focused determination of the immune state as active compared to quiescent can help assess the likelihood of allograft rejection. Immune activity is a harbinger of rejection events, which in turn impact graft survival, underscoring the need for reliable biomarkers that evaluate immune activity.

This example describes the validation of a blood gene expression signature or gene expression profile (GEP) to inform on immune quiescence as compared to both T cell-mediated (TCMR) and antibody-mediated (ABMR) rejection. Building on the extensively demonstrated utility of the AlloMap Heart gene set (Pham, M. X. et al., *N Engl J Med.* 2010 May 20; 362(20):1890-900), a novel 5-gene expression classifier for kidney allograft rejection was developed using 11 informative genes from AlloMap Heart as the starting gene set. The gene expression classifier was validated using two independent validation sets. Further, the performance of the 5-gene expression signature was tested independently and in conjunction with donor-derived cell free DNA (dd-cfDNA) levels, as determined with AlloSure®.

Materials and Methods

Study Design. The Circulating Donor-Derived Cell-Free DNA in Blood for Diagnosing Acute Rejection in Kidney Transplant Recipients ("DART") study (ClinicalTrials.gov Identifier: NCT02424227) was a multicenter, prospective, observational study to collect whole blood into Streck Cell-Free DNA BCT for the purpose of plasma dd-cfDNA measurement and to collect whole blood into PAXgene tubes for gene expression profiling. The study was run as previously described (Bloom, R. D. et al., *J Am Soc Nephrol.* 2017 July; 28(7):2221-2232). The institutional review board (IRB) at each site approved the study, and all the patients provided written informed consent. To further validate the performance of the 5-gene expression signature, a set of samples not included in the DART study, from Montefiore Medical Center, Bronx, NY, was tested. Samples were derived from the IRB-approved study of "Immune monitoring of Kidney Transplant recipients" (IRB #09-06-174). The clinical and research activities being reported are consistent with the Principles of the Declaration of Istanbul as outlined in the Declaration of Istanbul on Organ Trafficking and Transplant Tourism.'

Transplant Recipients and Samples. Transplant recipient samples were assigned to two general groups: Rejection or Immune Quiescence. Each group was defined by established Banff criteria (Haas, M. et al., *Am J Transplant.* 2018 February; 18(2): 293-307), and each contained subgroups as follows. The Rejection samples comprised T cell-mediated rejection (TCMR), antibody-mediated rejection (ABMR), or mixed TCMR/ABMR rejection (meeting criteria for both TCMR and ABMR). The Quiescence samples were one of three types: healthy stable (HS), which had no clinical or laboratory indicators of concern for the transplant (and therefore no clinically-indicated biopsy) and a low level of dd-cfDNA (<0.5%) as measured by AlioSure® non-rejection (NR), which were determined to not have signs of rejection upon pathologist review following a clinically indicated biopsy; and protocol Non-Rejection (pNR), which were determined to not have signs of rejection upon pathologist review following a protocol surveillance biopsy.

RNA purification. The DART PAXgene blood tubes were collected alongside Streck BCT blood tubes, shipped at ambient temperature, received within three days, and stored at −80° C. until RNA extraction from whole blood. After thawing, total RNA was purified using the QIASymphony PAXgene Blood RNA kit (Qiagen, Cat. No. 762635) on the QIAsymphony SP system following essentially the manufacturer's instructions. The second validation PAXgene sample set was extracted manually using PAXgene blood RNA kits (Qiagen, Cat. No. 762164) according to the manufacturer's instructions. The concentration and purity of the extracted RNA samples were determined by spectrophotometry. Samples were also analyzed for integrity by capillary electrophoresis (TapeStation, Agilent).

qRT-PCR (qPCR) Methodology. The purified RNA samples were subjected to qRT-PCR in the CareDx CLIA laboratory as described (Deng, M. C. et al., *Am J Transplant.* 2006 January; 6(1):150-60). The qPCR for each gene was run in triplicates and the raw $C_T$ values were used to calculate a smoothed mean $C_T$. The mean $C_T$ was then used for the development of the 5-gene expression signature without additional data processing methods from AlloMap Heart.

Classifier Training. Because it is standard to include the best-defined members of the two main cohorts when training a classifier, the Rejection sets for training and the primary validation set included TCMRIA, IB, IIA, and IIB along with the ABMR. Borderline TCMR samples were a part of the Rejection group in the second validation set. For ABMR, acute/active and chronic, active ABMR were included. The mean $C_T$ for the candidate test genes was normalized against six endogenous reference genes which were selected based on their stability in this sample set using a scheme similar to what was described previously (Deng, M. C. et al., *Am J Transplant.* 2006 January; 6(1):150-60). The normalized results were assessed for statistical significance in a univariate model. Six genes identified as statistically significant were then cross-validated via bootstrapping and leave-one-out validations. The five genes that passed these internal validations were grouped into three clusters based on their normalized $C_T$ level across the full set of training samples. Each cluster had pairwise correlation coefficient above 0.6. A multivariate model which integrates the normalized expression of the five genes was built to optimize performance to differentiate Rejection from Immune Quiescence in the training sample set.

RNA-seq methodology. Targeted RNA sequencing (RNA-seq) was chosen as a validation and testing platform to enable improved detection of low-expression genes, higher reproducibility, and accurate measurement of gene expression changes that can be readily expanded to additional gene sets and classifiers. A RNA-seq panel (QIAseq, Qiagen), which includes the five informative genes and 15 reference genes (see Table 4) as well as genomic DNA contamination controls and spike-in controls, was developed and optimized for PAXgene blood RNA samples on an RNA-seq platform using molecular tags (Peng, Q. et al., *BMC Genomics* 2015 August; 16:589-600). Single-read sequencing was performed on Illumina NextSeq 550. Primary analysis of the sequencing data was performed using the Qiagen GeneGlobe QIAseq bioinformatics pipeline for adaptor trimming, read mapping, quality checks, and computing the molecular tag counts (MTs) for the targeted transcripts. As the MTs are directly correlated with the initial copy number of the input the RNA, the corresponding $C_T$ number was derived using the equation $X_0=E_{amp}^{(b-Ct)}$, where $E_{amp}$ is the exponential amplification value, b is the y-intercept of log(copies) vs $C_T$, using the average amplification efficiency of 98%, and b=39 for the AlloMap qRT-PCR tests. The $C_T$ values for the informative genes were normalized using the average $C_T$ of the reference genes. The normalized $C_T$ numbers were then used to compute the gene expression score using the algorithm or classifier trained on the qRT-PCR data.

TABLE 4

List of exemplary reference genes that can be used to normalize gene expression levels.

| Gene: Classifier Training | Gene: Classifier Validation | Gene Name [from GeneCards] |
|---|---|---|
| ERCC5 | | ERCC Excision Repair 5, Endonuclease cell death 1 |
| GABPB2 | GABPB2 | GA Binding Protein Transcription Factor Subunit Beta 2 |
| CCDC159 | | Coiled-Coil Domain Containing Protein 159 |
| GPI | | Glucose-6-Phosphate Isomerase |
| RPLP1 | | Ribosomal Protein Lateral Stalk Subunit P1 |
| GUSB | GUSB | Glucuronidase Beta |
| | DECR1 | 2,4-Dienoyl-CoA Reductase 1 |
| | EWSR1 | EWS RNA Binding Protein 1 |
| | GAPDH | Glyceraldehyde-3-Phosphate Dehydrogenase |
| | HSP90AB1 | Heat Shock Protein 90 Alpha Family Class B Member 1 |
| | MAP3K3 | Mitogen-Activated Protein Kinase Kinase Kinase 3 |
| | MAPK9 | Mitogen-Activated Protein Kinase 9 |
| | NONO | Non-POU Domain Containing Octamer Binding |
| | RXRB | Retinoid X Receptor Beta |
| | SDHA | Succinate Dehydrogenase Complex Flavoprotein Subunit A |
| | SRRM1 | Serine And Arginine Repetitive Matrix 1 |
| | TBC1D10B | TBC1 Domain Family Member 10B |
| | TBP | TATA-Box Binding Protein |
| | TOP2B | DNA Topoisomerase II Beta |

dd-cfDNA Analysis. AlloSure® measurement of dd-cfDNA was performed as previously described. (Wong L. et al., *J Med Diagn Meth.* 2020; 9(5)).

Statistical Analysis. The analysis of differences between groups was performed using an unpaired t-test; performance metrics were calculated using standard methods in JMP version 13. ROC curves were generated using the pROC package in R.

Figure 9:
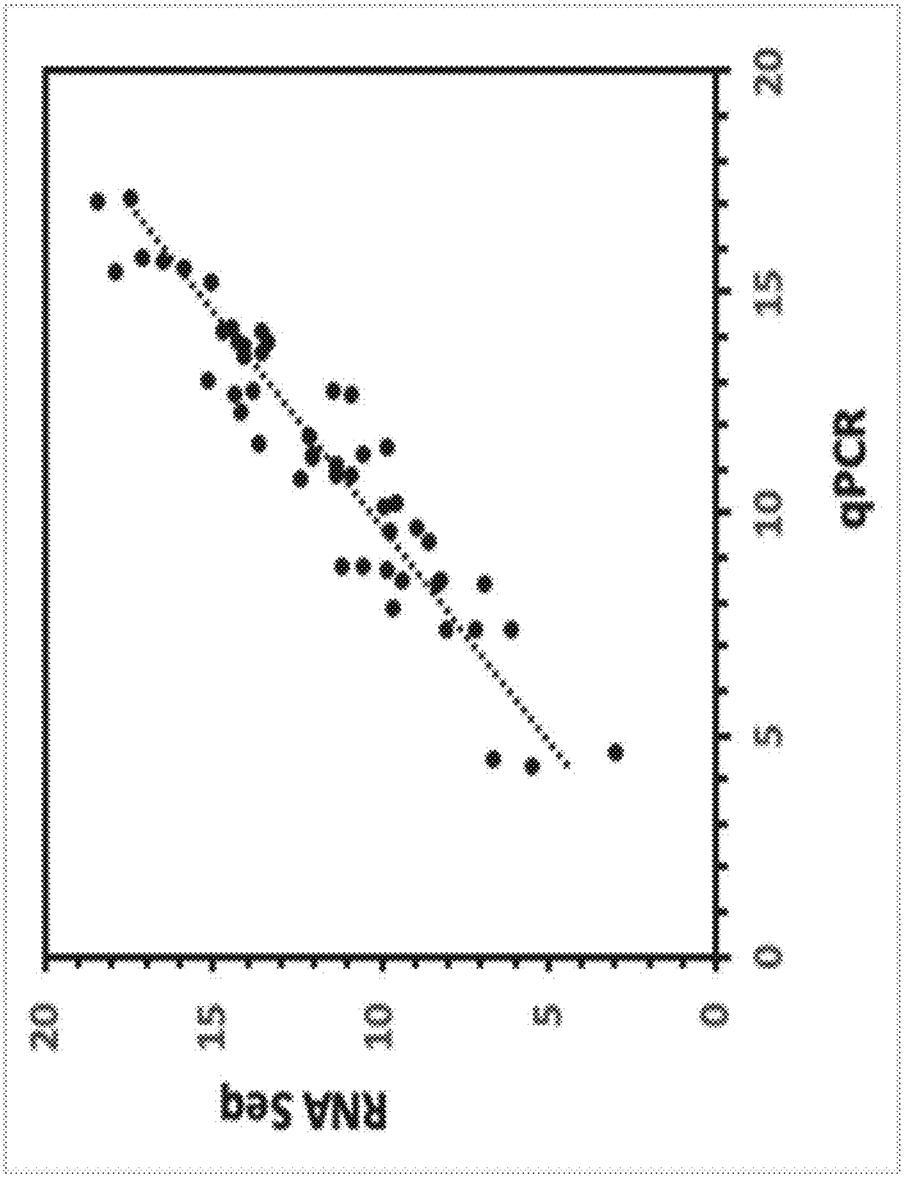
FIG. 9 shows an exemplary conversion of the 5-gene expression classifier trained on qPCR data to produce the same results from targeted RNA-sequencing data, in accordance to embodiments of the disclosure.

Conversion between RNA-seq and qRT-PCR. An RNA-seq platform incorporating unique molecular tags was used to enable improved detection of low-expression genes, higher reproducibility, and accurate measurement of gene expression changes that can be readily expanded to additional gene sets and classifiers. The training data were generated on the AlloMapHeart qRT-PCR platform. As both platforms measure the level of RNA in the same starting material, a conversion equation was defined based on the principles of the two methods. The conversion assumes that for the qPCR platform there is 98% PCR amplification efficiency and that a $C_T$ of 39 is equivalent to one starting molecule (Applicant's internal data). For RNA-seq, molecule counts were converted to $C_T$, then used in the gene expression classifier as trained on qRT-PCR results. This conversion of the raw results before application to the classifier enabled the use of the trained classifier algorithm without any modification. To ensure reliable results, the conversion equations were tested using DART samples analyzed on both (qRT-PCR and RNA-seq) platforms that were not members of the sets used for training or testing the gene expression classifier but covered the critical range of the test results. The results generated from the original method (qRT-PCR) and the final test method (RNA-seq) on the same samples showed 92% correlation, demonstrating the validity of the conversion (FIG. 9).

Single-center sample set preparation. The single-center sample set from Albert Einstein Medical Center was processed by extracting total RNA from the PAXgene tubes using manual spin columns. The manual methods and the automated methods were first compared on an independent sample set. Forty samples with paired PAXgene tubes (same venipuncture) from the DART study and two other studies in the Applicant's biobanks were extracted by the two methods, and a conversion equation defined for the small overall difference. After this conversion was determined and locked, the single-center validation set samples were subsequently run and the conversion was then applied as part of the data analysis to generate gene expression results.

Results

Development of the Gene Expression Classifier

The set of 11 informative genes utilized to detect rejection in heart transplantation (the AlloMap Heart gene set), an earlier invention by the Applicant, was developed from peripheral blood mononuclear cells (PMBC), a subset of cells in the blood, and comprises genes implicated in diverse immune pathways (Deng, M. C. et al., *Am J Transplant.* 2006 January; 6(1):150-60); therefore, this was chosen as a source of candidate genes for development of a gene expression classifier in kidney transplantation from whole blood, as described herein. Due to the complexity of purifying PMBCs at the time of collection, whole blood samples were collected from kidney transplant recipients into PAXgene tubes. Gene expression data were generated from a subset of the DART study patients designated as the training sample set, with 38 samples from 22 transplant recipients classified as Quiescence (healthy stable, HS, with donor-derived cell-free DNA levels below 1%, as measured with AlioSure® and 18 samples from 16 transplant recipients classified as Rejection after a clinically indicated biopsy (seven TCMR, eight ABMR, three mixed TCMR/ABMR) (Table 5). The only demographic differences between the cohorts in the training sample set were that the Quiescence cohort was earlier post-transplant and that the Rejection groups had higher serum creatinine and lower eGFR than the Quiescence groups, as expected. No differences were observed in race, gender, type of transplant, recipient or donor cytomegalovirus (CMV) serology, HLA mismatches, panel reactive antibodies, induction therapy, or maintenance immunosuppression (Table 5).

TABLE 5

Clinical characteristics of the DART analysis groups

| Clinical Characteristic | | Training | | | | Validation | | | |
|---|---|---|---|---|---|---|---|---|---|
| | | HS AS < 1% | R | P-Value | NR | HS | pNR | R | P-Value (NR vs R) |
| Number of Patients | | 22 | 16 | | 44 | 20 | 19 | 16 | |
| Number of Samples | | 38 | 18 | | 47 | 22 | 29 | 18 | |
| Race, n (%) | | | | 0.353 | | | | | 0.629 |
| | Black | 13 (34.2) | 8 (44.4) | | 14 (29.8) | 0 | 8 (27.6) | 4 (22.2) | |
| | White | 21 (55.3) | 9 (50.0) | | 25 (53.2) | 15 (68.2) | 19 (65.5) | 13 (72.2) | |
| | Native | 0 | 1 (5.6) | | 0 | 0 | 1 (3.5) | 0 | |
| | Hispanic/Latino | 3 (7.9) | 0 | | 5 (10.6) | 4 (18.2) | 1 (3.5) | 1 (5.6) | |
| | Asian | 0 | 0 | | 1 (2.1) | 1 (4.6) | 0 | 0 | |
| | Other | 1 (2.6) | 0 | | 2 (4.3) | 2 (9.1) | 0 | 0 | |
| Sex, n (%) | | | | 0.883 | | | | | 0.309 |
| | Men | 24 (63.2) | 11 (61.1) | | 30 (63.8) | 14 (63.6) | 21 (72.4) | 9 (50.0) | |
| | Women | 14 (36.8) | 7 (38.9) | | 17 (36.2) | 8 (36.4) | 8 (27.6) | 9 (50.0) | |
| Age at Enrollment (Years) | | 48.8 ± 13.7 | 47.9 ± 17.8 | 0.850 | 50.9 ± 14.5 | 54.9 ± 11.8 | 53.8 ± 12.7 | 39.4 ± 10.9 | 0.001 |
| Post-Transplant (Days) | | 94.5 ± 55.3 | 1091 ± 1071 | <0.001 | 965 ± 1360 | 244 ± 200 | 242 ± 192 | 1322 ± 1213 | 0.323 |
| CMV Serologic Status, n (%) | | | | 0.050 | | | | | 0.074 |
| | D−/R+ | 10 (26.3) | 3 (16.7) | | 13 (27.7) | 7 (31.8) | 12 (41.4) | 3 (16.7) | |
| | D+/R+ | 14 (36.8) | 3 (16.7) | | 14 (29.8) | 7 (31.8) | 7 (24.1) | 3 (16.7) | |
| | D−/R− | 7 (18.4) | 2 (11.1) | | 8 (17.0) | 3 (13.6) | 7 (24.1) | 4 (22.2) | |
| | D+/R− | 4 (10.5) | 3 (16.7) | | 5 (10.6) | 2 (9.1) | 3 (10.3) | 0 | |
| | Unknown | 3 (7.9) | 7 (38.9) | | 7 (14.9) | 3 (13.6) | 0 | 8 (44.4) | |
| Donor Type, n (%) | | | | 0.474 | | | | | 0.115 |
| | Deceased | 21 (55.3) | 13 (72.2) | | 28 (59.6) | 13 (59.1) | 15 (51.7) | 11 (61.1) | |
| | Living - Unrelated | 4 (10.5) | 1 (5.6) | | 14 (29.8) | 3 (13.6) | 8 (27.6) | 2 (11.1) | |
| | Living - Related | 13 (34.2) | 4 (22.2) | | 5 (10.6) | 6 (27.3) | 6 (20.1) | 5 (27.8) | |
| Creatinine | | 1.46 ± 0.53 | 2.47 ± 1.15 | <0.001 | 2.27 ± 1.49 | 1.36 ± 0.53 | 1.61 ± 0.57 | 2.83 ± 0.91 | 0.084 |
| eGFR | | 55.0 ± 14.9 | 33.6 ± 13.1 | <0.001 | 38.9 ± 19.8 | 56.3 ± 19.6 | 48.2 ± 13.2 | 25.9 ± 11.3 | 0.002 |
| HLA Class 1 No. of Mismatches (A. B) | | 2.7 ± 1.1 | 3.1 ± 1.3 | 0.300 | 2.5 ± 1.3 | 2.1 ± 1.1 | 2.9 ± 1.2 | 1.7 ± 1.1 | 0.020 |
| HLA Class 2 No. of Mismatches (DR) | | 1.2 ± 0.6 | 1.2 ± 0.5 | 0.947 | 1.1 ± 0.8 | 1.1 ± 0.8 | 1.2 ± 0.7 | 0.9 ± 0.8 | 0.317 |
| PRA Class I | Mean PRA | 1.72 | 1.73 | 0.995 | 24.1 | 10.8 | 9.03 | 13.4 | 0.172 |
| | Samples | 36 | 15 | | 39 | 16 | 29 | 15 | |
| PRA Class II | Mean PRA | 4.67 | 18.1 | 0.120 | 14.8 | 10.9 | 2.9 | 20.9 | 0.524 |
| | Samples | 36 | 14 | | 3.9 | 16 | 29 | 15 | |
| Induction | | | | 0.052 | | | | | 0.464 |
| patients (%) | ATG | 2 (91) | 8 (50) | | 9 (20.5) | 2 (10) | 0 | 5 (31.3) | |
| | Campath | 3 (13.6) | 3 (18.8) | | 9 (20.5) | 1 (5) | 0 | 2 (12.5) | |
| | Simulect | 2 (9.1) | 0 | | 0 | 1 (5) | 0 | 1 (6.3) | |
| | Other | 3 (13.6) | 3 (18.8) | | 8 (18.2) | 2 (10) | 0 | 3 (18.8) | |
| | None | 14 (64.6) | 5 (31.3) | | 23 (52.3) | 15 (75) | 19 (100) | 8 (50) | |
| Immunosuppression | | | | 0.262 | | | | | 0.519 |
| samples (%) | Cyclosporin | 2 (5.3) | 2 (11.1) | | 5 (10.6) | 1 (4.5) | 0 | 2 (11.1) | |
| | Tacrolimus | 35 (92.1) | 16 (88.9) | | 38 (80.9) | 20 (20) | 27 (93.1) | 15 (83.3) | |
| | Mycophenolate | 34 (89.5) | 14 (77.78) | | 40 (85.1) | 20 (90.9) | 28 (96.7) | 15 (83.3) | |
| | Prednisone | 17 (44.7) | 14 (77.78) | | 28 (59.6) | 16 (72.7) | 10 (34.5) | 13 (72.2) | |
| | Rapamycin | 2 (5.3) | 1 (5.6) | | 3 (6.4) | 0 | 0 | 2 (11.1) | |
| | Azathioprine | 2 (5.3) | 1 (5.6) | | 3 (6.4) | 0 | 1 (3.4) | 1 (5.6) | |
| | Belatacept | 1 (26) | 0 | | 2 (4.3) | 0 | 2 (6.9) | 0 | |
| | Other | 0 | 3 (16.7) | | 0 | 0 | 0 | 2 (11.1) | |

Figure 2B:
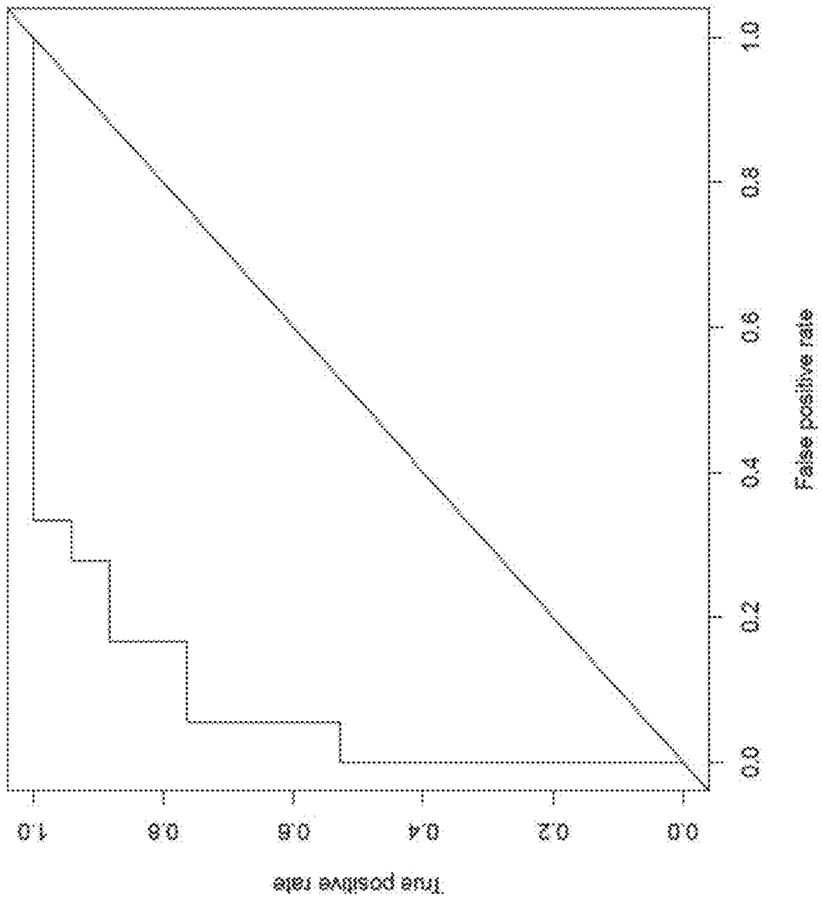
FIGS. 2A-2B show exemplary training data results for the 5-gene expression signature, in accordance with embodiments of the disclosure.
Figure 2A:
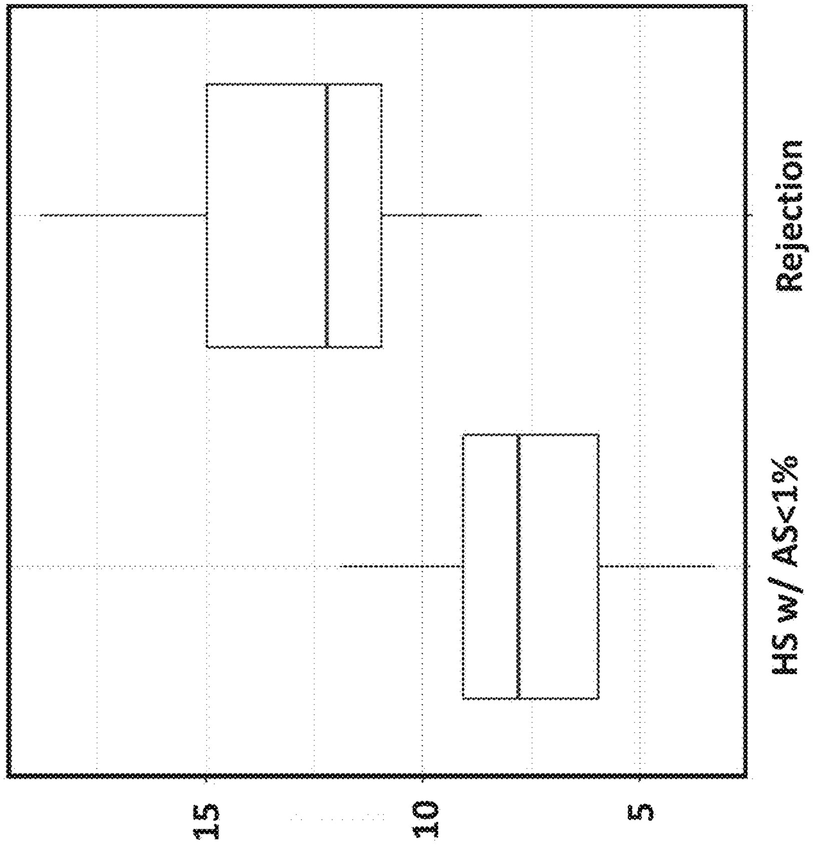

Given the differences in sample type and the transplanted organ, a new gene expression classifier was developed starting from the AlloMap Heart gene set. Of the 11 informative genes included in the AlloMap Heart gene set (Deng, M. C. et al., *Am J Transplant.* 2006 January; 6(1):150-60), six were significantly different between the Quiescence and Rejection groups in the training set in a univariate model (P<0.02). Bootstrap and leave-one-out testing within the training set indicated that five of the six genes were used in more than 75% of instances; subsequent stepwise selection yielded three important clusters with five genes. These genes represented biological functions related to immune response pathways: DCAF12 and MARCH8 are involved in modulating immune reactivity, FLT3 and IL1R2 are steroid-responsive genes, and PDCD1 is expressed on activated T lymphocytes (Dedrick, R. L. et al., *J Immunotoxicol.* 2007 July; 4(3):201-7). In the training set used to define and train the gene expression classifier, the classifier readily distinguished Rejection from Quiescence, with P<0.001, and with an area under the receiver operating characteristics curve (AUC) of 93.9% (95% CI 88.9%-99.1%), as shown in FIGS. 2A-2B.

Validation of the Gene Expression Classifier Using Independent Sets of Samples

Figure 3B:
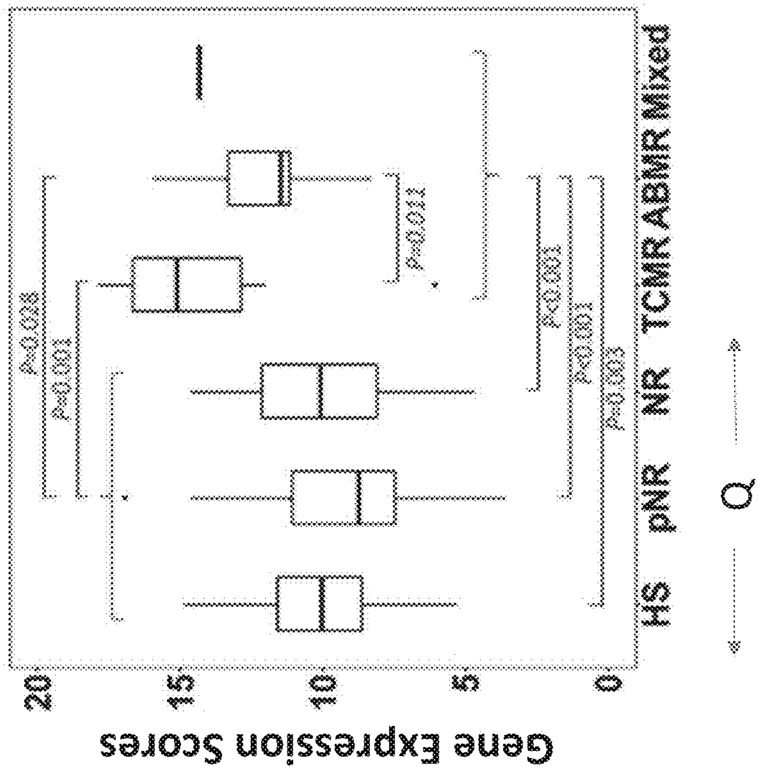
FIGS. 3A-3D illustrate that the 5-gene expression signature differentiates immune quiescence from allograft rejection in the primary independent validation set, in accordance with embodiments of the disclosure.
Figure 3A:
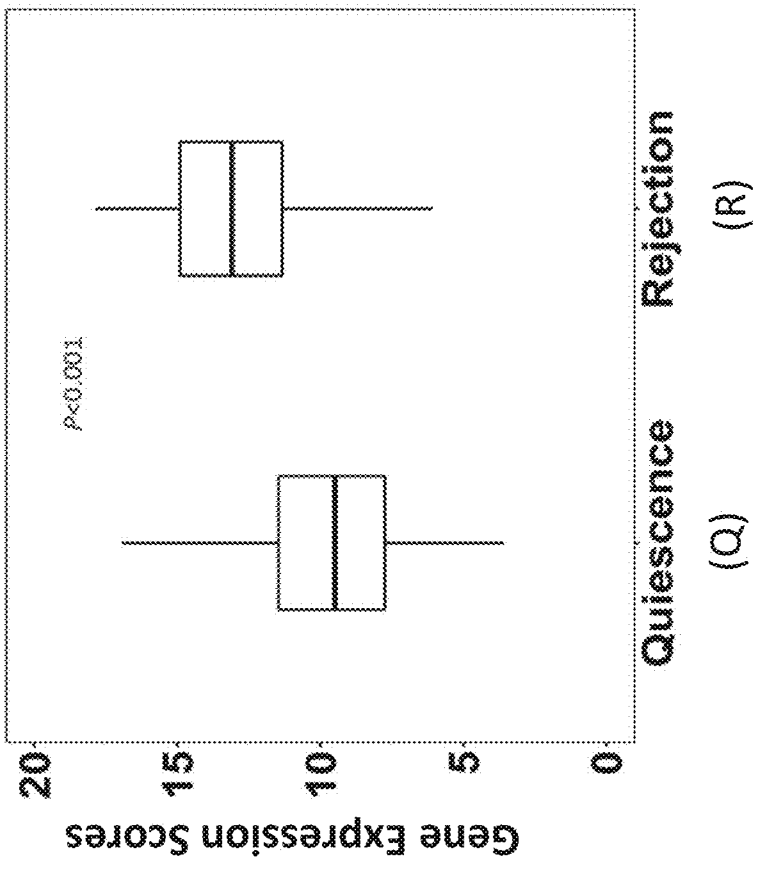
Figure 3C:
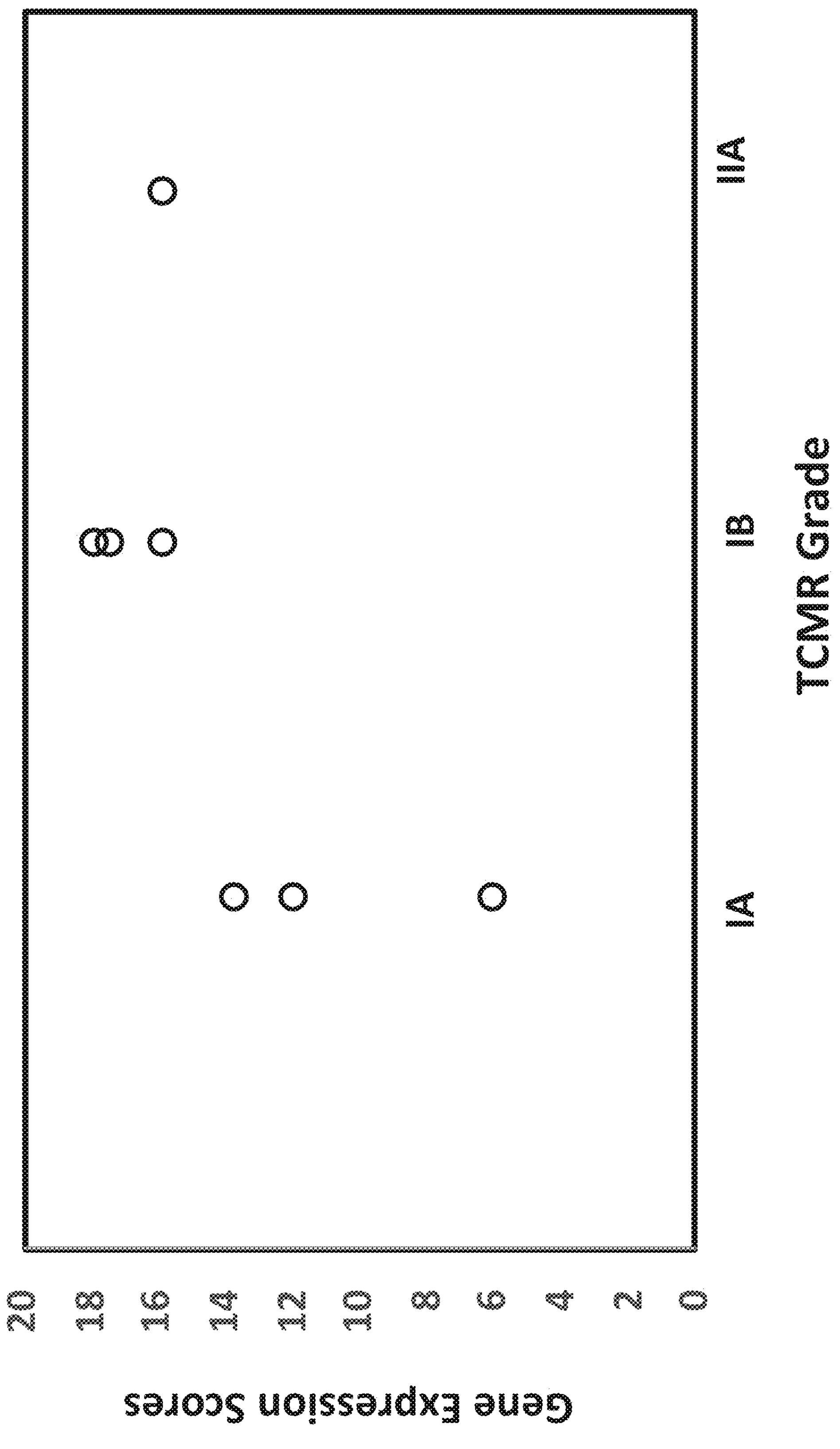
Figure 3D:
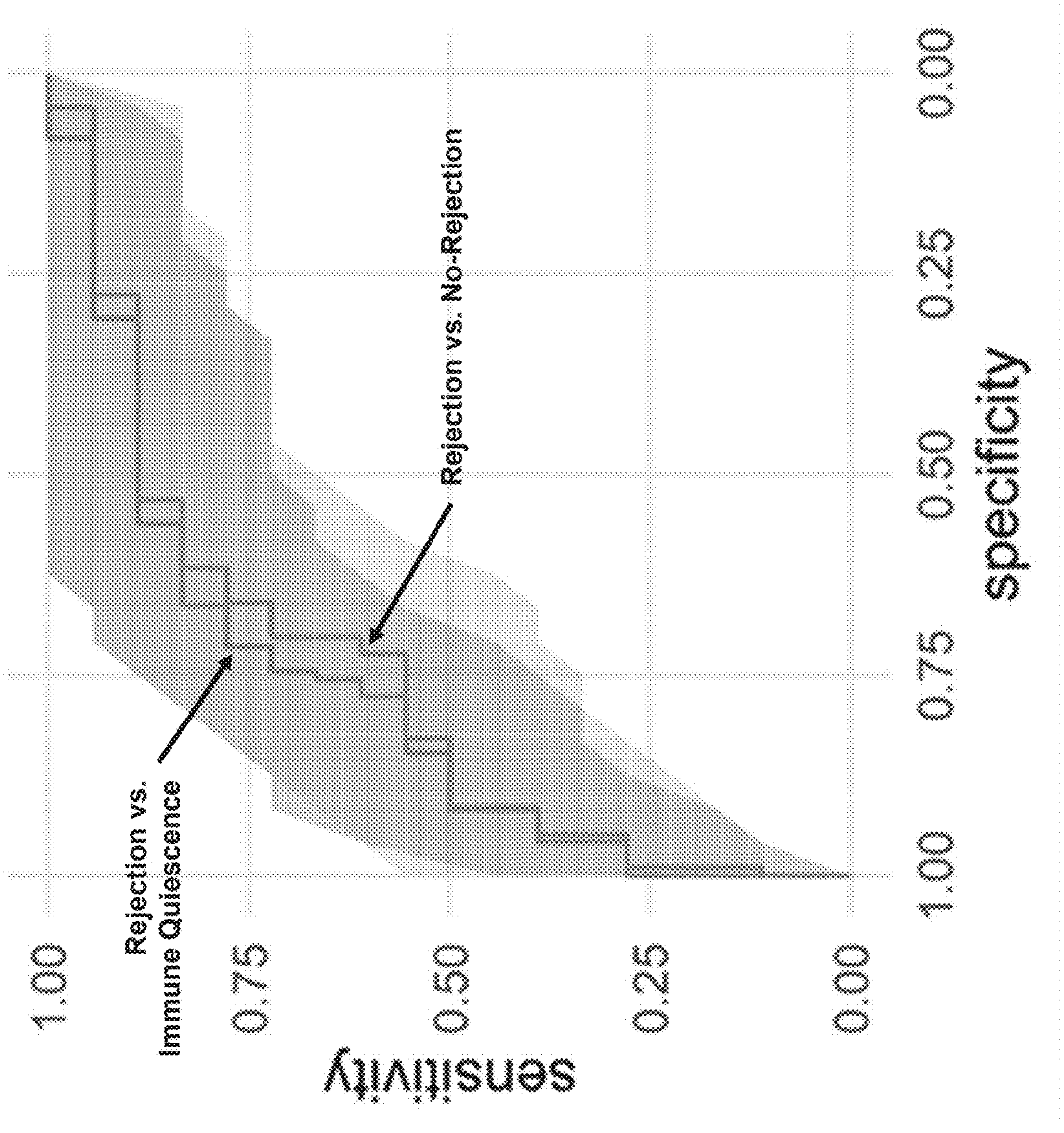

A second set of DART samples, from kidney transplant recipients not included in the training of the classifier, was used as an independent primary validation cohort. These included 98 Quiescence samples (from 22 healthy, stable (HS) kidney transplant recipients who had no clinical or laboratory indicators of concern for the graft and therefore no clinically-indicated biopsy, 29 kidney transplant recipients with protocol biopsy-defined non-rejection (pNR), and 47 kidney transplant recipients with clinically indicated biopsy who did not experience a rejection (NR) and 18 rejections (from seven kidney transplant recipients with biopsy-confirmed TCMR, 10 kidney transplant recipients with biopsy-confirmed ABMR, and one kidney transplant recipient with biopsy-confirmed mixed TCMR/ABMR) (see Table 5). The only demographic differences between the cohorts in the primary validation set were that the Rejection cohort were younger and had fewer HLA class 1 mismatches. There was not a statistical difference in time post-transplant between the Rejection and Quiescence cohorts. The Rejection cohort had higher serum creatinine and lower estimated glomerular filtration rate (eGFR) than the Quiescence cohort, as expected. No differences were observed in race, gender, type of transplant, time post-transplant, HLA class II mismatches, panel reactive antibodies, induction therapy, or maintenance immunosuppression. This set of independent samples validated that the gene expression classifier distinguished Quiescence (median 9.49; IQR 7.68-11.53) from Rejection (median 13.09; IQR 11.25-15.28), p<0.001 (FIG. 3A). The medians (and IQR) for each of the sample groups were: HS=10.04 (8.38-11.85), pNR=8.73 (7.45-11.13), NR=10.07 (8.05-12.14), TCMR=15.09 (11.99-17.42), ABMR=11.48 (10.95-13.68), and mixed=14.33. Each of the three defined Quiescence groups (HS, pNR, NR) was significantly different from the Rejection cohort (P-values for Rejection vs HS=0.003, Rejection vs pNR<0.001, Rejection vs NR<0.001) (FIG. 3B). Each of the defined types of Rejection, TCMR, ABMR, and mixed, was different from the Quiescence cohort (FIG. 3B), with P-values of 0.028 and 0.001 for ABMR and TCMR vs. Quiescence, respectively. Furthermore, the data suggested that higher grades of TCMR may have higher gene expression signature scores (FIG. 3C). The area under the receiver operating characteristics curve (AUC) for Quiescence vs Rejection in the primary validation set was 0.786 (95% CI 0.661-0.911), demonstrating the excellent performance of the gene expression signature across the score range (FIG. 3D).

Figure 4B:
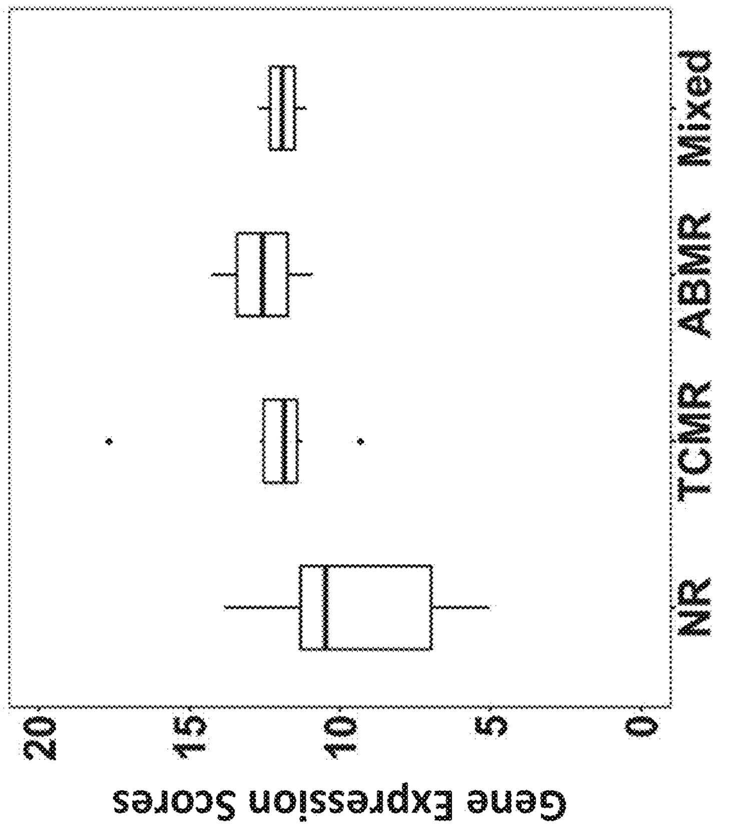
FIGS. 4A-4C illustrate that the 5-gene expression signature differentiates quiescence from rejection in a second independent (single center) validation set, in accordance with embodiments of the disclosure.
Figure 4A:
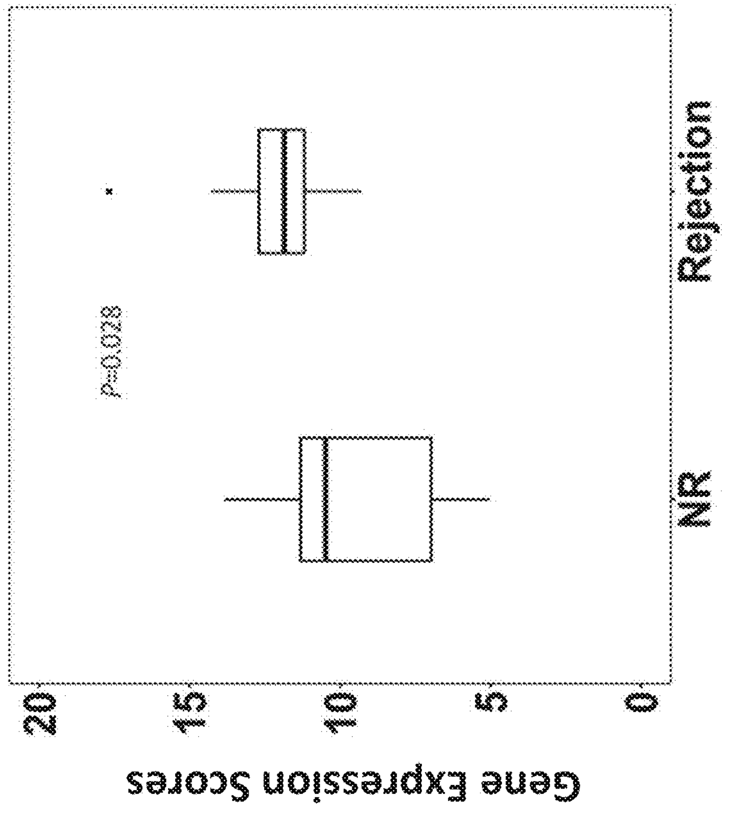
Figure 4C:
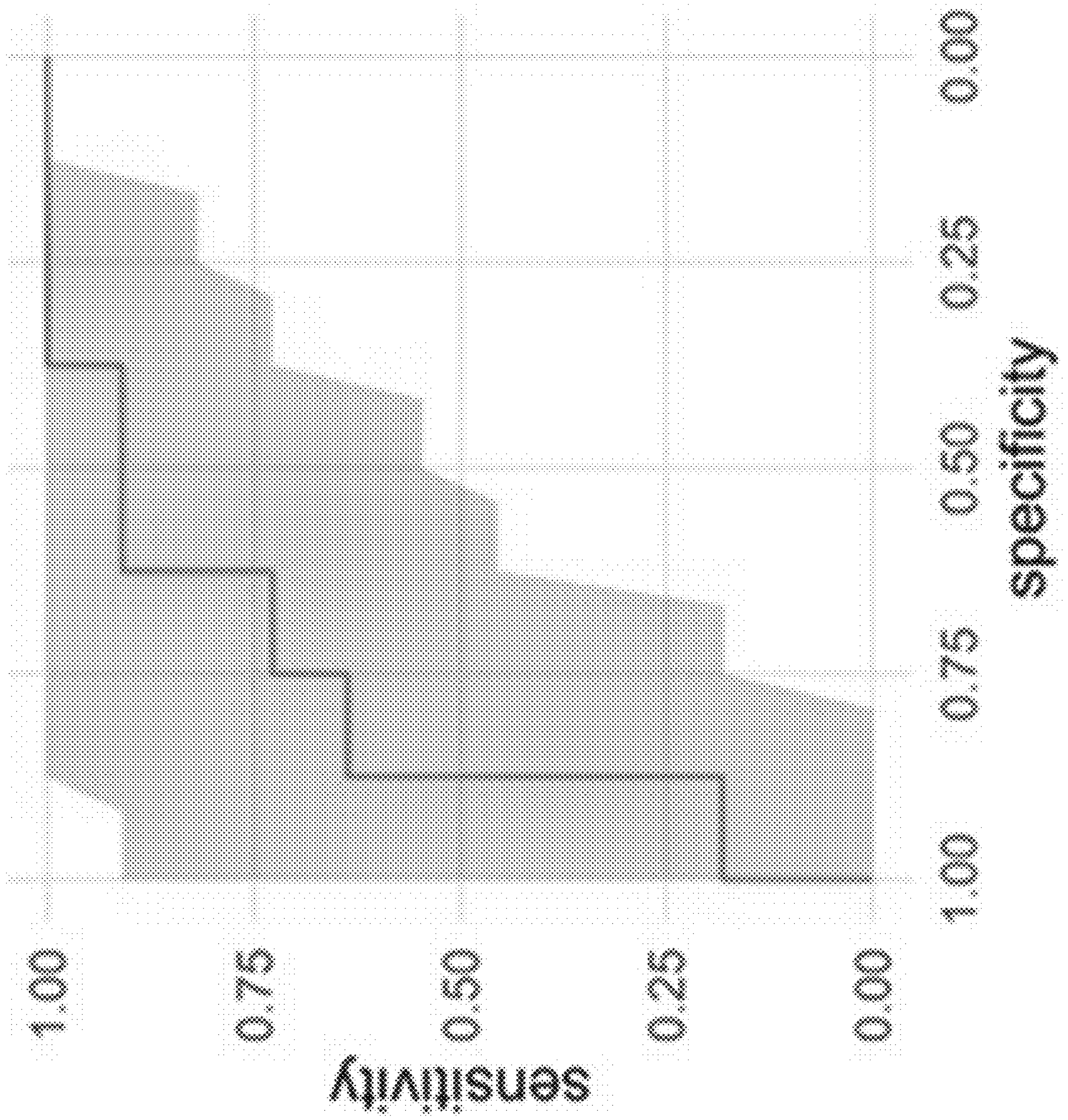

To further validate the performance of the gene expression classifier, a set of samples from a center not included in the DART study was also evaluated. The Quiescence cohort in this set included eight NR, while the Rejection cohort contained 11 samples (2 ABMR, 7 TCMR, 2 mixed rejections). In this second validation set, the gene expression signature scores were significantly different between Quiescence (NR) and Rejection (p=0.028, FIG. 4A). Both the TCMR and the ABMR samples had elevated scores relative t the NR group (FIG. 4B). The TCMR group consisted of five IIA rejections and two borderline Rejections, with a median gene expression score of 11.85 (11.26-12.67). The area under the receiver operating characteristics curve (AUC) for discriminating Quiescence (NR) from Rejection (TCMR, ABMR, mixed TCMR/ABMR) was 0.796 (95% CI 0.571-1) (FIG. 4C).

Figure 5A:
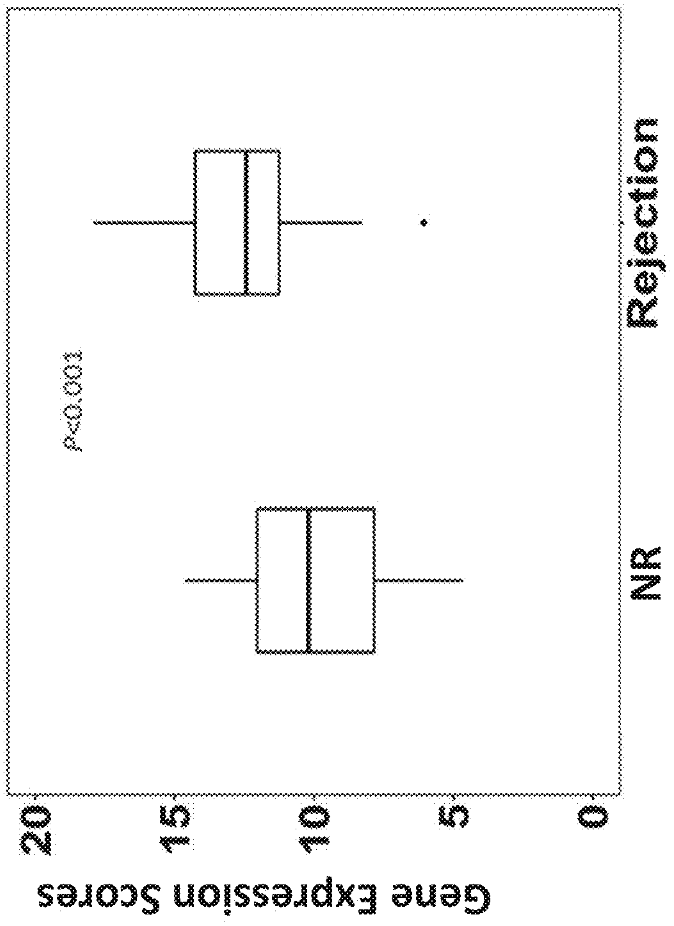
FIGS. 5A-5C illustrate that the 5-gene expression signature discriminates quiescence from rejection in the combined validation sets, in accordance with embodiments of the disclosure.
Figure 5B:
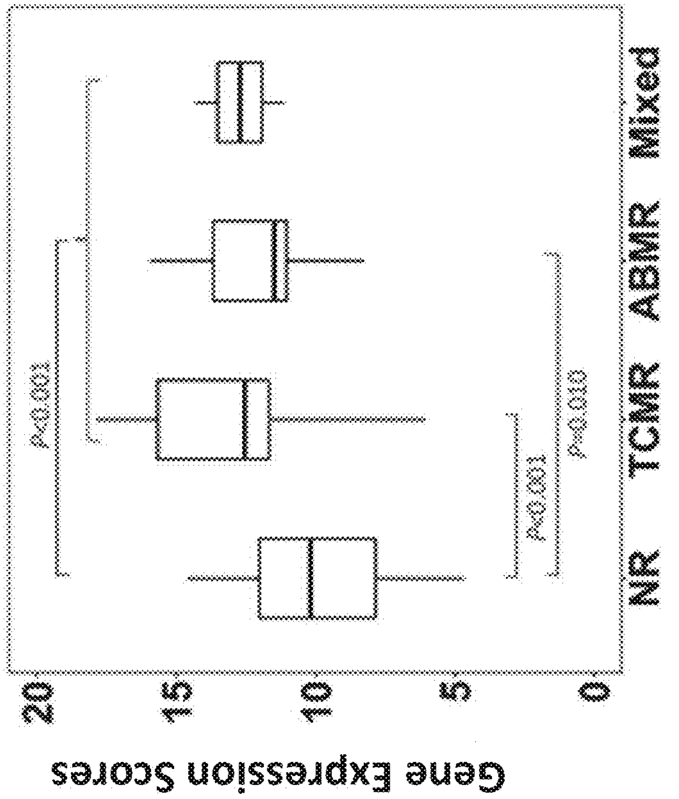
Figure 5C:
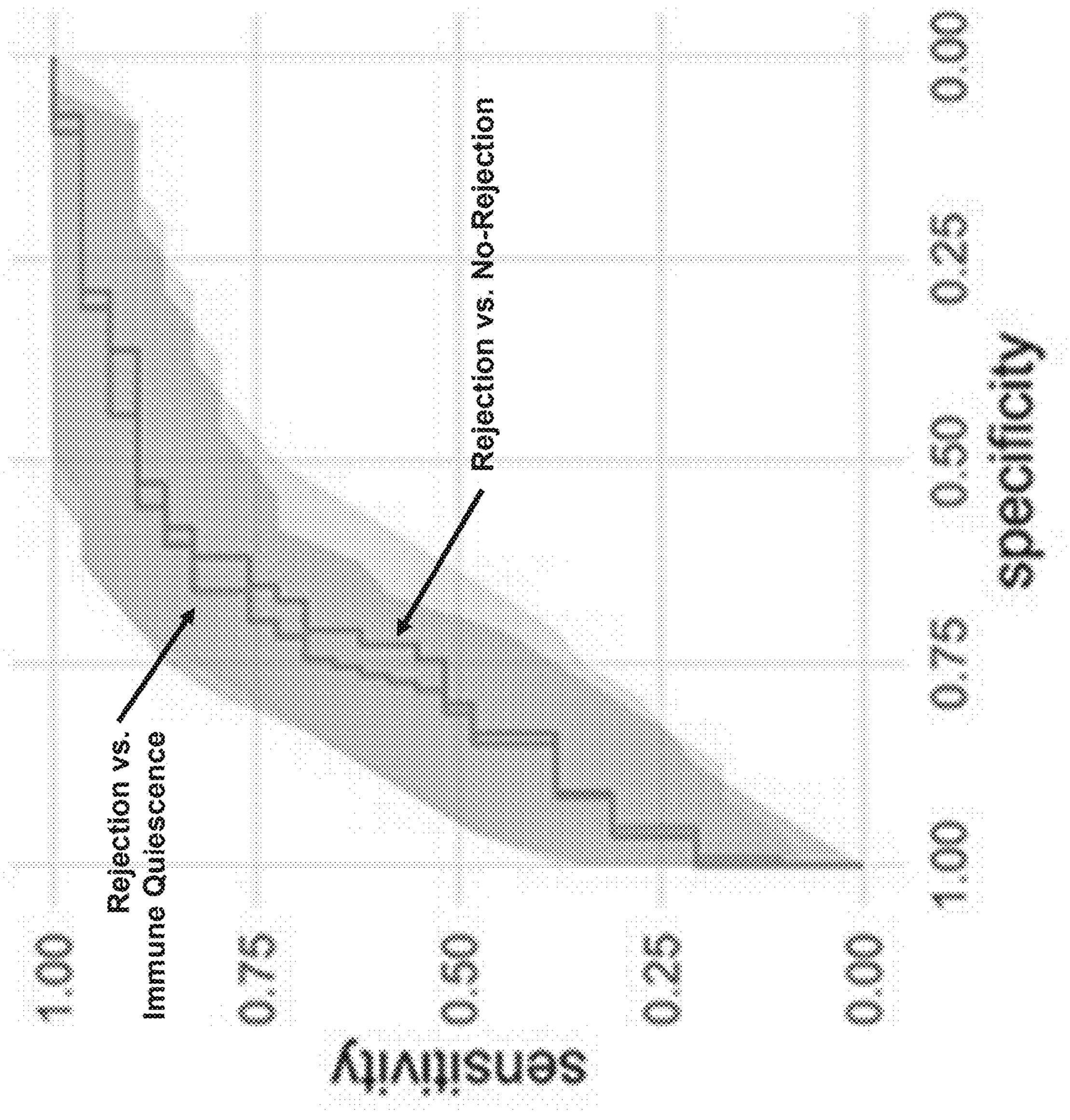
Figure 6A:
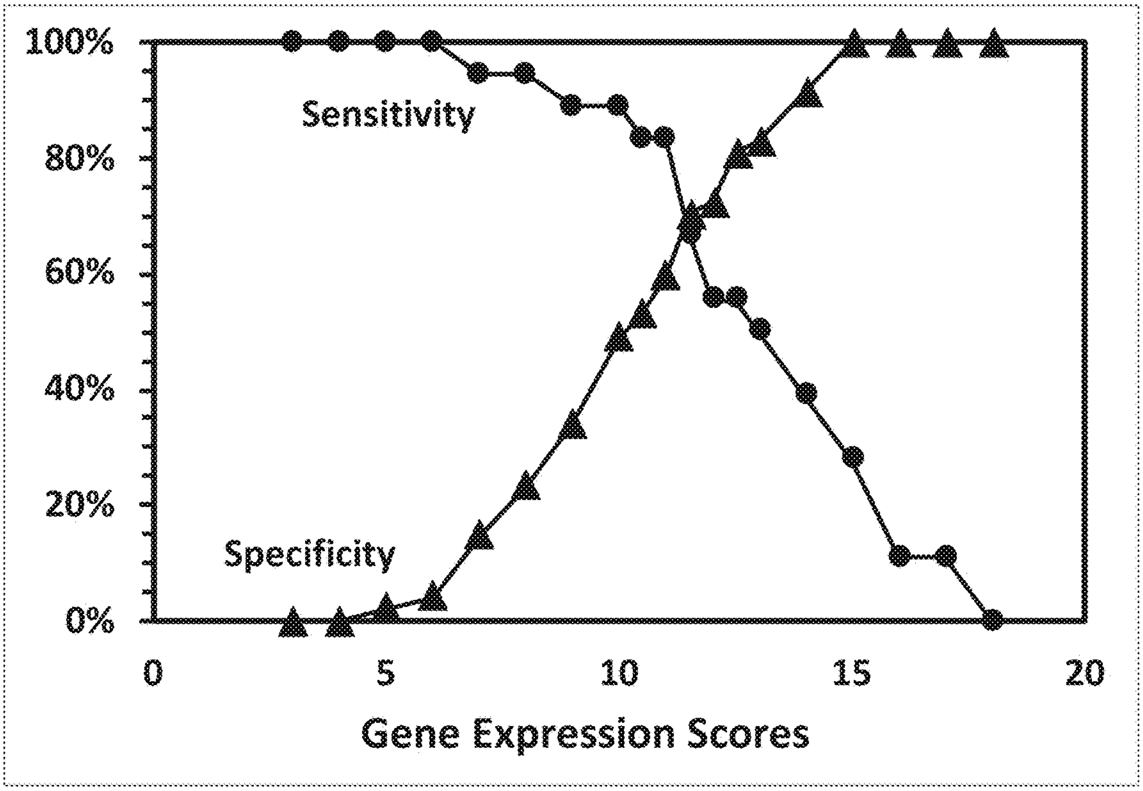
FIGS. 6A-6F provide exemplary performance characteristics of the 5-gene expression signature across the range of gene expression scores, in accordance with embodiments of the disclosure.
Figure 6B:
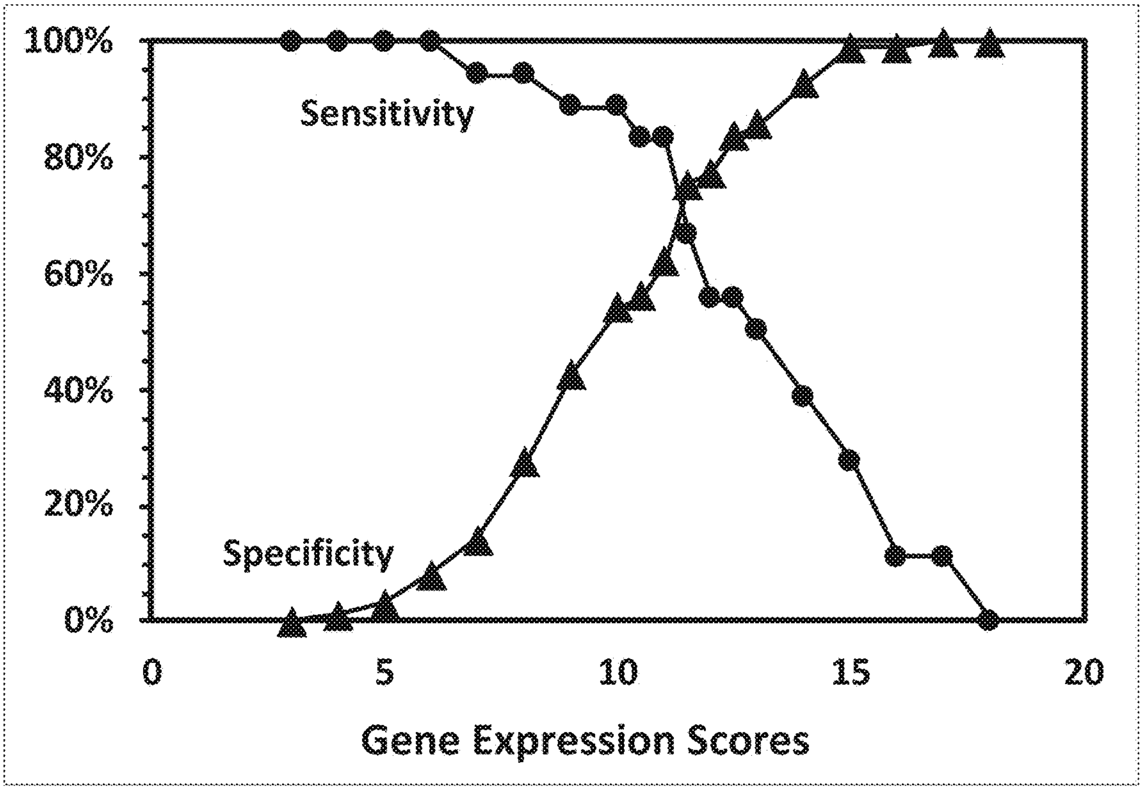
Figure 6C:
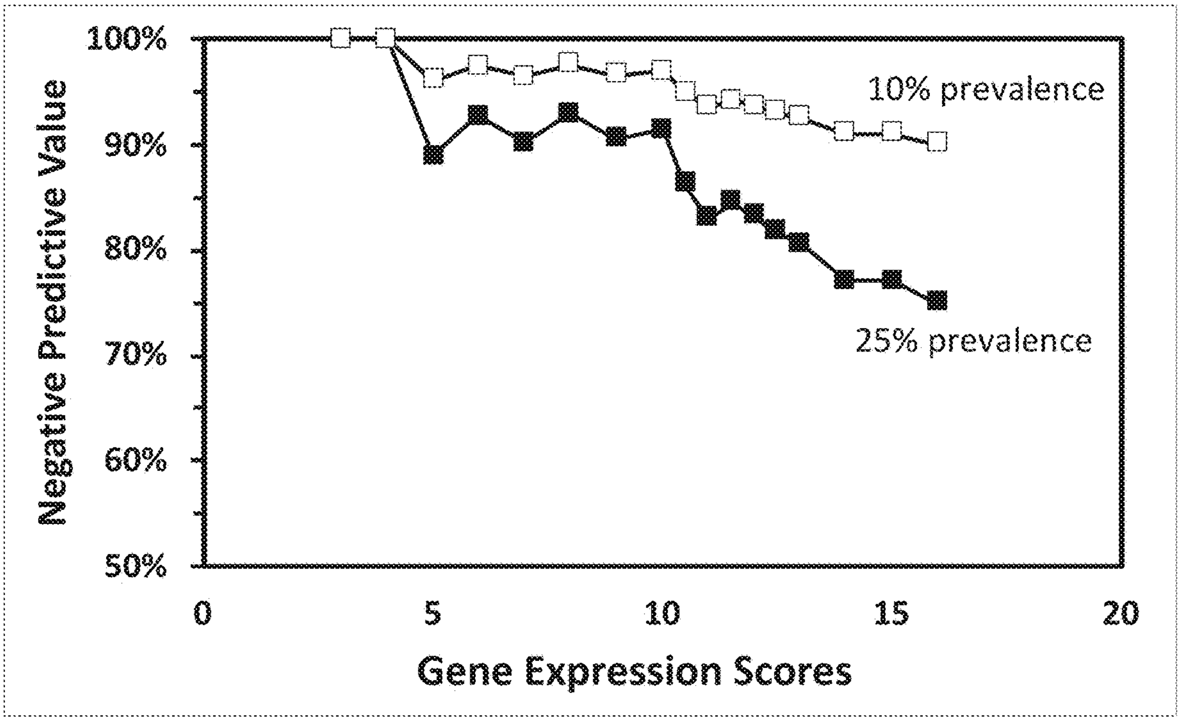
Figure 6D:
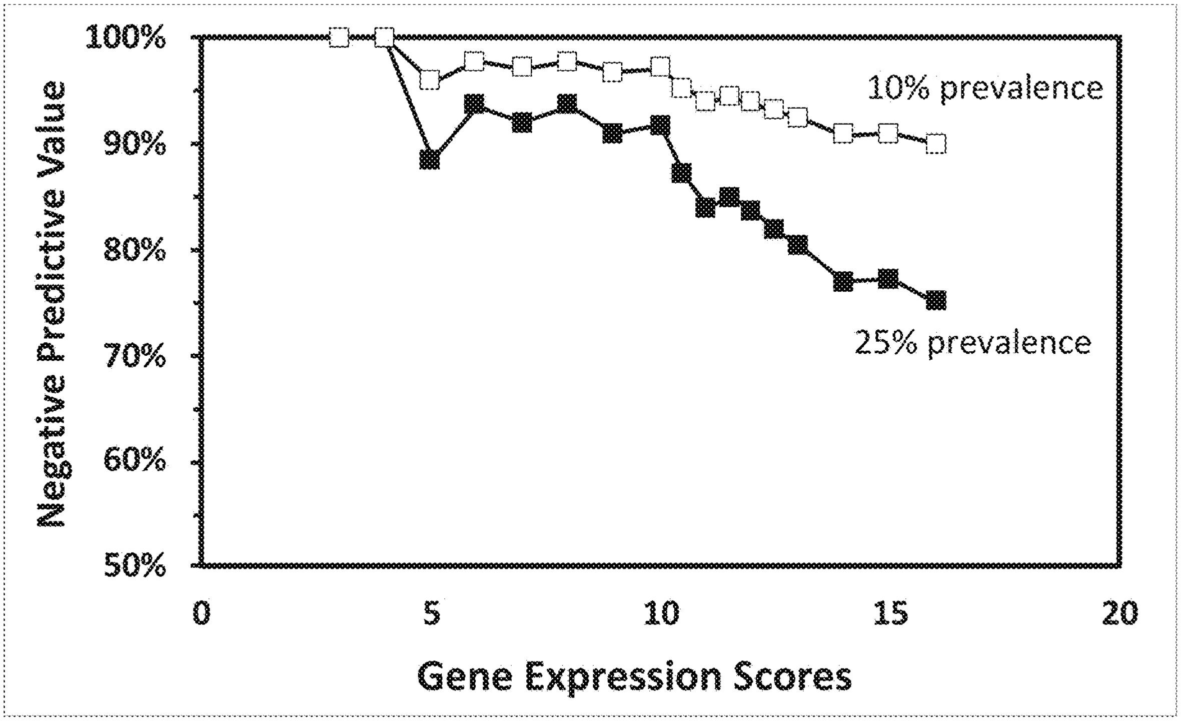
Figure 6E:
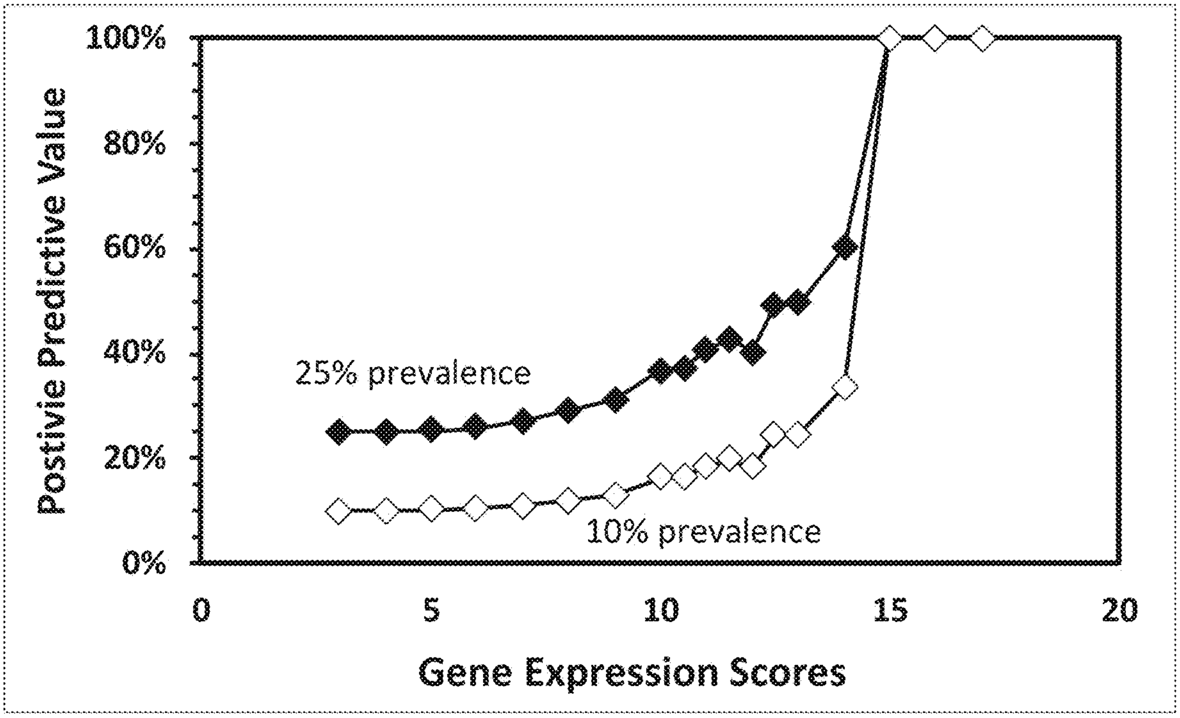
Figure 6F:
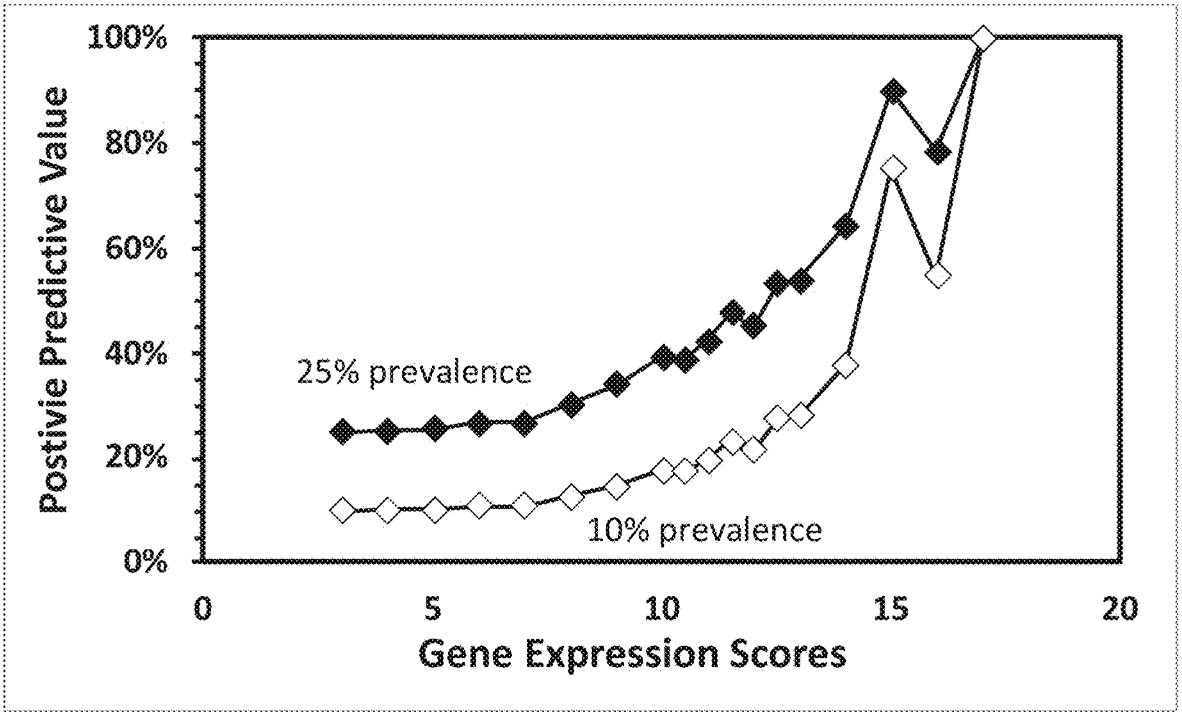

The performance of the 5-gene expression signature and classifier was also assessed in the combined validation sets (primary validation set and second validation set). In the combined analysis, the scores for the NR group (median 10.19, IQR 7.64-12.09) were significantly lower than the scores for the Rejection (R) group (median 12.43, IQR 11.12-14.29), P<0.001 (FIG. 5A). All three Rejection groups showed elevated scores: TCMR (median 12.55, IQR 11.52-16.25, n=14), ABMR (median 11.48, IQR 10.95-14.06, n=12), and mixed Rejection (median 12.72, IQR 11.12-14.33, n=3) (FIG. 5B). Analysis of the combined independent validation sets resulted in an area under the receiver operating characteristics curve (AUC) of 0.779 (95% CI 0.686-0.871) for Quiescence versus Rejection cohorts (FIG. 5C).

Negative predictive values (NPV) and positive predicted values (PPV) were determined at prevalence levels of 10% and 25%, representing the estimated prevalence of allograft rejection on first-year surveillance and clinically indicated biopsies, respectively ((Hart A. et al., Am J Transplant. 2018 January; 18 Suppl 1(Suppl 1):18-113; Bloom, R. D. et al., *J Am Soc Nephrol.* 2017 July; 28(7):2221-2232).). The single-center sample set contained only NR in the Quiescence cohort; therefore, the performance of the classifier to differentiate the full Quiescence group from biopsy-defined Rejection was assessed on the DART validation set. FIGS. 6A-6F show plots of sensitivity, specificity, positive predicted value (PPV), and negative predictive value (NPV) of the classifier. For all performance metrics, the data are shown with either the full Quiescence cohort (HS, NR, and pNR) or with only the NR group. Sensitivity did not change as the Rejection (R) cohort remained the same, but specificity, NPV, and PPV were dependent on the choice of Quiescence cohort samples. The threshold used for binary performance characterization was 11.5, at which the gene expression classifier score achieved the maximum accuracy for sensitivity and specificity (FIGS. 6A-6F). At the 11.5 score, the 5-gene expression signature had a PPV of 23.2% and an NPV of 95.3% at 10% prevalence, and a PPV of 47.6% and an NPV of 87.2% at 25% prevalence to discriminate Rejection from Quiescence.

Figure 7A:
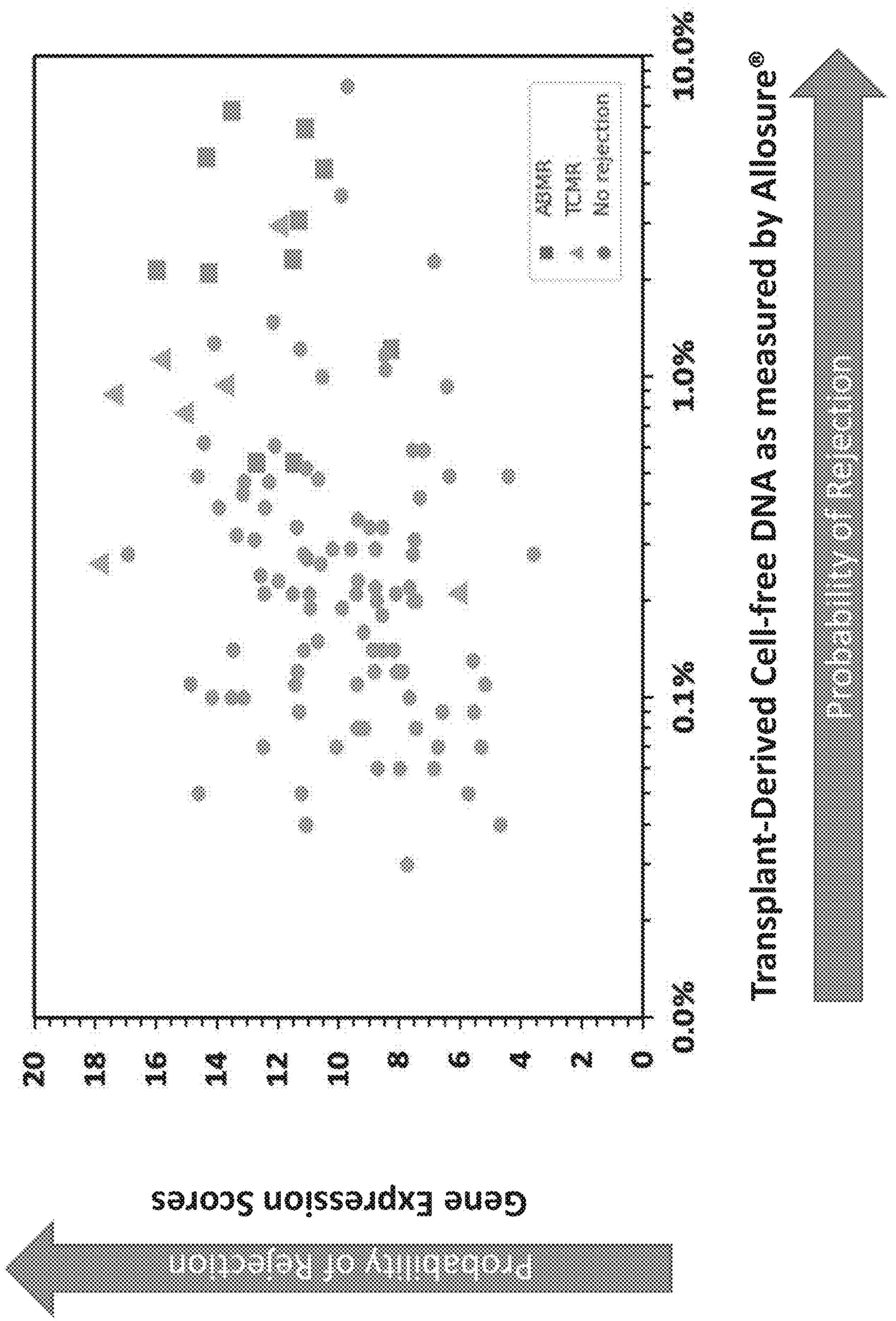
FIGS. 7A-7B show exemplary results of the combined analysis of the 5-gene expression signature and levels of transplant-derived cell-free DNA (as measured by AlloSure®), in accordance to embodiments of the disclosure, illustrating that the combined analysis, or the use of combined scores, has greater quiescence versus rejection discriminating ability than either alone.

Combined Analysis of the 5-Gene Expression Signature and Donor-Derived Cell-Free DNA (Dd-cfDNA) Levels For samples in the DART study, plasma levels of donor-derived cell-free DNA (dd-cfDNA) were also determined using AlloSure®. Since donor-derived cell-free DNA levels are highly associated with graft injury (Bloom, R. D. et al., *J Am Soc Nephrol.* 2017 July; 28(7):2221-2232), while gene expression provides insights into immune activation, the signal obtained from dd-cfDNA levels was hypothesized to be different from that of the 5-gene expression signature, although both were correlated with Rejection. FIG. 7A shows the data for all Quiescence and Rejection cohorts (mixed rejection was included in the ABMR group). Circles indicate all types of Quiescence (HS, pNR, NR), triangles indicate TCMR, and squares indicate ABMR (including mixed rejections). There was a weak correlation between the scores derived from dd-cf DNA levels and gene expression, respectively (R=0.15, P=0.233). However, samples with dd-cf DNA levels of 1% or above had higher gene expression classifier scores. Several TCMR samples with dd-cf DNA levels between 0.5% and 1%, i.e., intermediate scores below the 1% threshold, had very high gene expression classifier scores, suggesting a role for the 5-gene expression signature to inform on which of these intermediate scores likely correlate with Rejection (Stites, E. et al., *Am J Transplant.* 2020 September; 20(9):2491-2498).

Figure 7B:
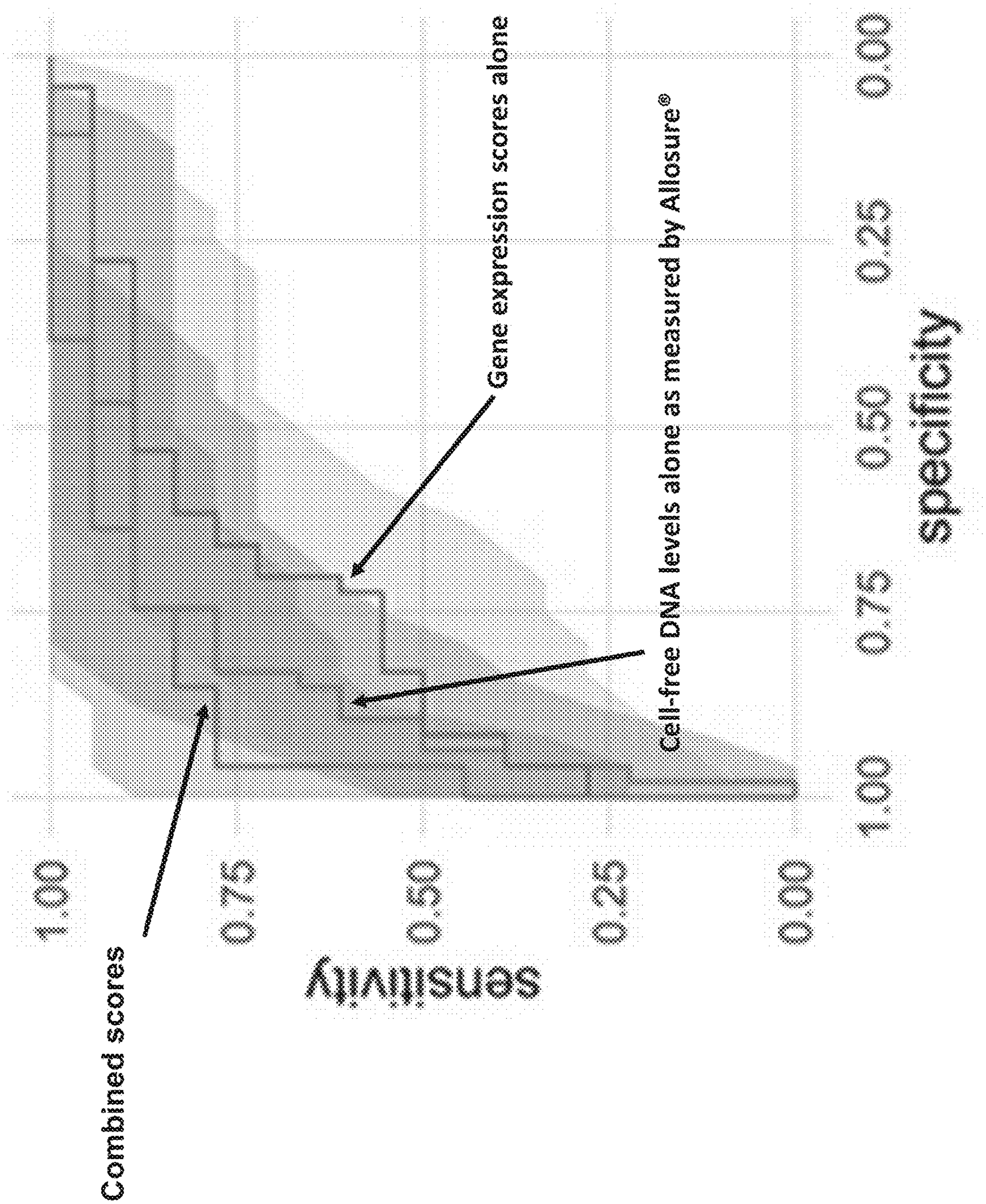

To examine the potential of coupled testing in post-transplant care, a combined score was derived with equal weighting of dd-cf DNA levels and gene expression signature scores. The range of this combined score can be envisioned along the diagonal from the lower left to the upper right in the plot of FIG. 7A. These data were used to generate an ROC plot for the combined score, which was compared to the ROC plots for dd-cf DNA levels or 5-gene expression signature alone in the same sample set (FIG. 7B). These data showed a superior performance for the combined use of the gene expression signature and AlioSure® versus gene expression signature alone (p=0.005).

SUMMARY

Factors predisposing the development of active rejection have been extensively studied, with the recipient immune system proving to be a key intermediary in many relevant processes, including ischemia—reperfusion injury, infection, and response to immunosuppression. Uncontrolled inflammation in kidney allografts leads to chronic damage and progressive fibrosis that accounts for the majority of long-term allograft loss (Naesens, M. et al., *Kidney Int.* 2011 December; 80(12):1364-76; Moreso, F. et al., *Am J Transplant.* 2006 April; 6(4):747-52). Genetic predictors of active rejection have also been described in recent years, some of which implicate immune activity. Taken in concert, these data suggest that monitoring gene expression in peripheral blood immune cells may lead to earlier or more sensitive detection of active rejection (Dorr, C. et al., *PLoS One.* 2015 May 6; 10(5):e0125045; Li, L. et al., *Am J Transplant.* 2012 October; 12(10):2710-8; Kurian, S. M. et al., *Am J Transplant.* 2014 May; 14(5): 1164-72).

The primary objective of the study described herein was to validate a gene expression signature and classifier that discriminates immune quiescence from kidney allograft rejection. The gene expression classifier was tested using two validation sets: the primary validation set comprised independent patients from DART and the second validation set was from a single center. Both sets demonstrated the validity of the classifier to discriminate biopsy-defined Rejection from Quiescence. Classifier scores were statistically significantly different between the rejection cohort and the quiescence cohort as well as between the quiescence cohort and either TCMR or ABMR. Results in the three subgroups of quiescence (HS, pNR, NR) were each statistically different from those seen in rejection. In both validation sets, the AUC demonstrated excellent diagnostic performance. The classifier had an NPV of over 95% in a surveillance population (10% prevalence) based on a score of 11.5, chosen for maximal sensitivity and specificity.

This gene expression classifier was developed using a candidate gene approach. Once trained on a subset of the DART samples, the gene expression signature was validated on a separate set of DART samples, all from kidney transplant recipients and independent from the training set. The second validation set was from a single center that did not participate in the DART study. The performance of the classifier was similar in the two validation sets, indicating the classifier's applicability and validity across the general kidney transplant population.

While the current study comprised a limited number of rejection samples, those nevertheless represented TCMR, ABMR, and mixed TCMR/ABMR rejections), and the gene expression signature demonstrated significant performance in all comparisons.

Further, a second independent validation set confirmed the performance of the gene expression classifier in the DART validation set. Although three different types of Quiescence samples (NR, pNR, and HS) were included in this study, there are other subsets of the target transplant recipient population that can be characterized on this classifier as well, including infection, interstitial fibrosis and tubular atrophy, drug toxicity, BKV nephropathy, and recurrent or de-novo glomerular disease.

Additionally, the use of a targeted RNA-seq technology with unique molecular identifiers enabled highly sensitive and precise measurement of multiple transcripts in parallel.

The determination of dd-cfDNA levels provides insight into molecular injury patterns at the allograft level, while gene expression profiling as a measure of immune activity may provide a different perspective on rejection mechanisms. Gene expression profiling may also provide additional resolution to discriminate between types of allograft injury, including drug toxicity that can lead to injury in the absence of rejection.

The combined analysis of dd-cf DNA levels and gene expression signatures, therefore, has the potential of added value. Indeed, when the DART validation set was analyzed using both dd-cf DNA levels and 5-gene expression signatures, a considerably increased diagnostic performance was observed coupled with a possible indication of the type of rejection, as the gene expression signature scores appeared, at least in the primary validation cohort, higher in cases of TCMR than in cases of ABMR, whereas the assessment of dd-cf DNA levels often performs stronger in cases of ABMR (Jordan, S. et al., Transplant Direct 2018).

Immune activity biomarkers can strengthen the high negative predictive value of existing markers, allowing the confidence to rule out pathology by identifying those kidney transplant recipients who are immunoquiescent. These types of markers also open the prospect of immunomodulation. Reducing the dosis and/or frequency of immunosuppressive regimens in transplant recipients who are adequately immunosuppressed and increasing them in those transplant recipients who are not, may lead to improved outcomes for both transplant recipient populations. The combination of allograft injury markers (dd-cfDNA levels) and immune activity markers (gene expression profiling) may take us in the direction of non-invasive characterization of underlying pathology and one step closer to offering a true liquid biopsy.

Example 3: Gene Expression Profiling Using 4-Gene or 3-Gene Differential Gene Expression Signatures Discriminates Rejection from Immune Quiescence in Kidney Transplant Recipients This example demonstrates the analysis of whole blood samples from kidney allograft recipients to determine the differential expression of three or four genes (any possible 3- or 4-combinations of the five informative genes described in Examples 1 and 2) that inform on the immune activity status of the allograft.

Figure 8:
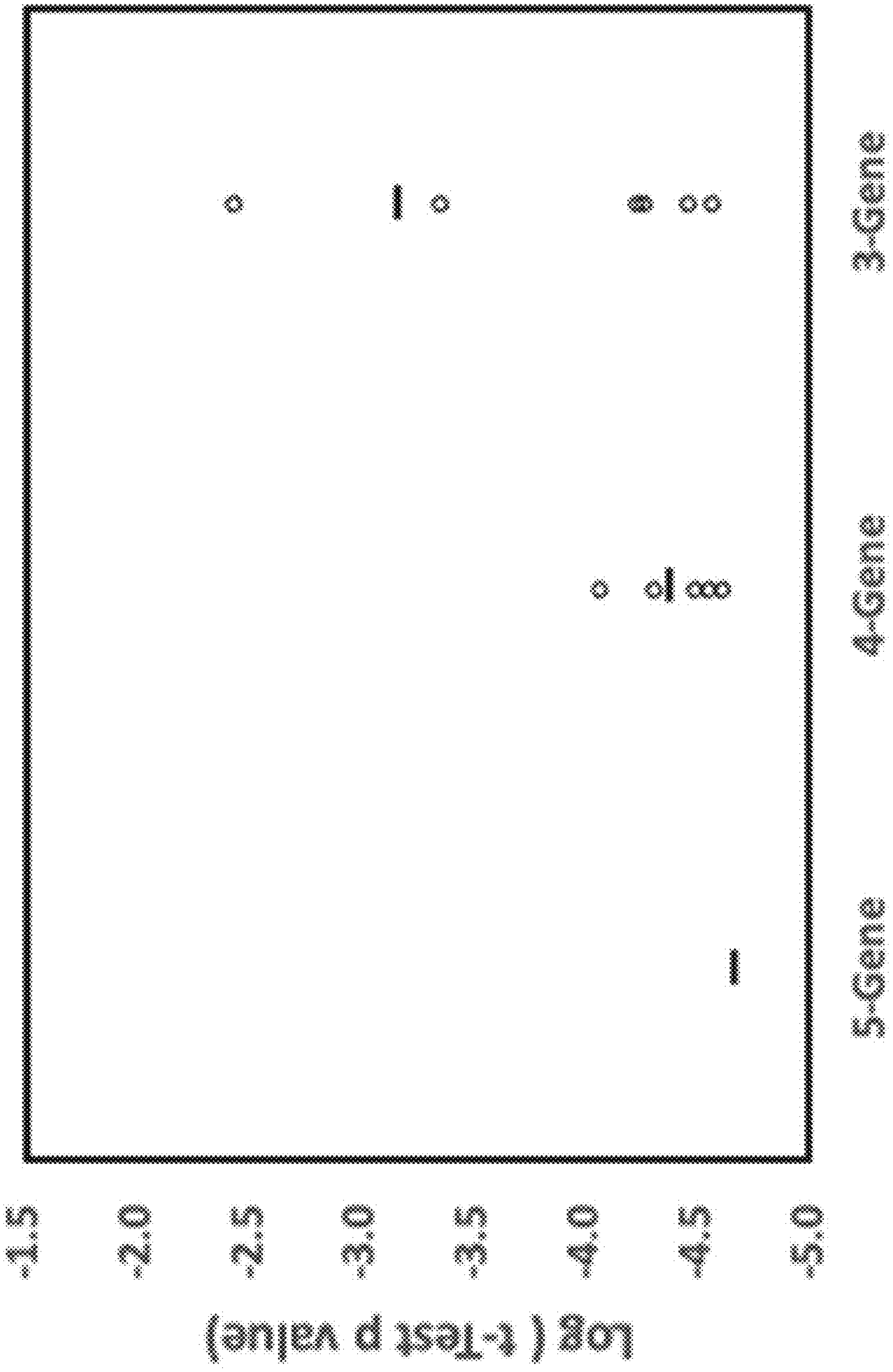
FIG. 8 shows exemplary log of t-test p-values for the ability of the 5-gene expression signature, 4-gene expression signature or 3-gene expression signature to detect and discriminate rejection versus quiescence, in accordance to embodiments of the disclosure. The horizontal lines describe the log of the mean p-values. The circles are the individual p values for each of the datasets. For the 5-gene expression signature, the line is the only value.

Quantification of differential gene expression across a range of gene expression signature scores was used to discriminate allograft Rejection from Quiescence. In Table 2 and Table 3, median scores (interquartile range, IQR) for 3-gene and 4-gene expression signatures are provided that discriminate between control groups (immune quiescent Q, non-rejection NR, and Q+NR) and rejection groups (ABMR, TCMR, mixed ABMR-TCMR rejection, and all rejections in combination). FIG. 8 provides an overview of the log t-test p-values for the 5-gene, 4-gene, and 3-gene expression signatures.

Each of the three or four informative gene combinations may be used alone or in combination with other genes from their respective gene clusters that inform on allograft Rejection versus Quiescence. Furthermore, additional complementary analysis of donor-derived cell-free DNA levels to inform on the health status of the allograft may be performed.

TABLE 2

| Median Scores (IQR) for 4-Gene Expression Signatures | | | | | | | |
|---|---|---|---|---|---|---|---|
| 4-Gene combination | All Rejections (R) | ABMR | TCMR | Mixed | Non-Rejection (NR) | Immuno-Quiescent, confirmed by biopsy (Q) | NR and Q |
| IL1R2, MARCH8, PDCD1, DCAF12 | 16.59 (14.75-18.59) | 15.38 (14.5-16.88) | 18.25 (16.72-20.96) | 18.64 (n/a) | 14.20 (11.89-15.73) | 12.17 (11.19-15.02) | 13.17 (9.09-14.95) |
| FLT3, MARCH8, PDCD1, DCAF12 | 9.05 (7.91-11.16) | 8.09 (7.79-9.63) | 11.21 (9.04-12.36) | 10.01 (n/a) | 6.26 (4.32-8.54) | 5.08 (3.66-7.28) | 6.04 (2.11-7.28) |
| FLT3, IL1R2, PDCD1, DCAF12 | 11.96 (9.93-13.55) | 9.95 (9.79-12.42) | 14.22 (11.82-15.59) | 13.15 (n/a) | 8.98 (6.65-11.05) | 7.22 (5.92-9.63) | 8.55 (3.87-9.94) |
| FLT3, IL1R2, MARCH8, DCAF12 | 20.64 (19.15-21.97) | 19.4 (19.15-20.81) | 22.74 (20.53-23.09) | 21.21 (n/a) | 18.08 (16.91-19.38) | 17.06 (15.93-17.96) | 17.85 (15.22-18.68) |
| FLT3, IL1R2, MARCH8, PDCD1 | 13.14 (11.64-15.18) | 11.85 (11.19-13.3) | 15.4 (12.85-16.81) | 14.51 (n/a) | 10.05 (7.94-11.88) | 7.78 (7.74-11.66) | 9.51 (7.77-11.71) |

TABLE 3

| Median Scores (IQR) for 3-Gene Expression Signatures | | | | | | | |
|---|---|---|---|---|---|---|---|
| 3-Gene combination | All Rejections (R) | ABMR | TCMR | Mixed | Non-Rejection (NR) | Immuno- Quiescent, confirmed by biopsy (Q) | NR and Q |
| MARCH8, PDCD1, DCAF12 | 13.54 (12.35-15.04) | 13.17 (10.7-15.25) | 14.03 (13.1-14.33) | 13.06 (n/a) | 11.81 (9.61-13.61) | 10.59 (9.05-12.13) | 11.44 (7.23-12.43) |
| FLT3, PDCD1, DCAF12 | 8.53 (7.15-10.67) | 7.4 (6.96-9.18) | 10.69 (8.53-11.67) | 9.33 (n/a) | 5.8 (3.67-7.92) | 4.13 (2.8-6.52) | 5.46 (1.11-6.71) |
| IL1R2, MARCH8, PDCD1 | 17.10 (15.62-19.28) | 16.18 (15.21-17.47) | 19.15 (17.23-21.57) | 19.32 (n/a) | 14.64 (12.36-16.06) | 13.12 (12.03-15.99) | 13.86 (10.18-15.41) |
| FLT3, MARCH8, PDCD1 | 9.27 (8.00-11.17) | 8.34 (7.77-9.59) | 11.25 (9.01-12.46) | 10.2 (n/a) | 6.29 (4.15-8.31) | 5.50 (3.83-7.38) | 6.07 (2.23-7.36) |
| IL1R2, PDCD1, DCAF12 | 16.07 (13.87-18.06) | 14.38 (13.8-16.29) | 17.35 (16.2-20.36) | 17.96 (n/a) | 13.54 (11.3-15.24) | 11.33 (10.35-14.08) | 12.66 (8.24-14.33) |
| FLT3, IL1R2, PDCD1 | 18.53 (17.6-20.92) | 18.37 (17.39-18.53) | 19.53 (18.65-22.62) | 21.38 (n/a) | 17.33 (16.44-18.49) | 16.85 (15.96-17.79) | 17.29 (14.48-18.04) |

Example 4: Clinical-Grade Validation of an Immune Quiescence Gene Expression Signature to Identify Rejection in Kidney Allograft Recipients Allograft rejection remains a major cause of graft failure in kidney transplantation. Here, the validation of a blood 5-gene expression signature, or gene expression profile (GEP), to inform on immune quiescence, T cell-mediated rejection (TCMR), antibody-mediated rejection (ABMR) and mixed rejection, using peripheral blood and targeted RNA sequencing, is described. Furthermore, the clinical utility of the combined analysis of gene expression profiling and transplant donor-derived cell-free DNA (dd-cfDNA) amounts or levels is demonstrated. The combined analysis can utilize combined scores correlating gene expression scores and donor-derived cell-free DNA (dd-cfDNA) amounts levels, with equal or unequal weighting, to inform on immune quiescence, T cell-mediated rejection (TCMR), antibody-mediated rejection (ABMR) and mixed rejection. Alternatively, the combined analysis can utilize the relationship of gene expression scores and transplant donor-derived cell-free DNA (dd-cfDNA) amounts or levels without the use of combined scores to inform on immune quiescence, T cell-mediated rejection (TCMR), antibody-mediated rejection (ABMR) and mixed rejection. The combined analysis can also utilize the relationship of gene expression scores and transplant donor-derived cell-free DNA (dd-cfDNA) amounts or levels to identify or indicate conditions, other than transplant rejection, that may cause an elevation of immune activity, such as, e.g., autoimmune diseases, chronic inflammatory diseases, autoimmune and chronic inflammatory diseases, systemic infections.

As described herein, a classifier using 5 informative genes (DKAF12, MARCH8, FLT3, IL1R2, and PDCD1) was developed and validated in three independent sets of samples, on a total of 169 quiescence (or non-rejection)

samples and 66 rejection samples from 222 kidney allograft recipients. The primary validation set, as described in Example 2, comprised 98 quiescence samples (negative biopsy; or healthy stable without biopsy) and 18 rejection samples (7 T cell-mediated rejection (TCMR), 10 antibody-mediated rejection (ABMR), and 1 mixed rejection). The second validation set, as described in Example 2, included eight quiescence (negative biopsy) and 11 rejection samples (7 TCMR, 2 ABMR, and 2 mixed TCMR/ABMR) samples. The third validation set included 65 quiescence (negative biopsy) and 37 rejection samples (16 TCMR, 11 ABMR, and 10 mixed TCMR/ABMR).

In addition, for each transplant recipient for whom paired dd-cfDNA and GEP samples, obtained within 30 days prior to biopsy, were available, dd-cfDNA levels were determined using AlloSure®.

The classifier for the 5-gene expression signature produced quantitative gene expression signature scores in the range from 0 to 20. In all validation sets, the gene expression signature scores differed significantly between the quiescence groups and the rejection groups, whereby higher scores were associated with a higher risk of rejection. Receiver operating characteristic (ROC) analysis demonstrated an AUC of 0.786 for the first validation set, an AUC of 0.800 for the second validation set, and an AUC of 0.78 for the third validation set. The gene expression signature scores were not significantly correlated with the scores derived from dd-cf DNA levels, although both were elevated in case of rejection. The ability to discriminate rejection from quiescence on the basis of either 5-gene expression profiling scores or dd-cfDNA level scores was improved when the gene expression signature scores and the scores derived from dd-cf DNA levels were used together in a combined score (AUC 0.894).

The clinical-grade validation of the 5-gene expression signature as an indicator of a transplant recipient's immunological activity demonstrated a clear differentiation between rejection and immune quiescence with a sensitivity of 70% and specificity of 66% for allograft rejection, and a negative predictive value (NPV) of 95% to discriminate rejection from quiescence at 10% prevalence of rejection. The insights about immunological activity derived from the 5-gene expression signature were complementary to the insights about allograft injury derived from dd-cfDNA levels using AlloSure®. The combined investigation of immunological activity and allograft injury, by analyzing both gene expression levels and donor-derived cell-free nucleic acids levels or amounts, provided an enhanced assessment of the status of a transplant, and the health status of a transplant recipient overall, and a roadmap to inform not only on the likely presence or absence of immune quiescence, T cell-mediated rejection (TCMR), antibody-mediated rejection (ABMR) and mixed rejection but also on the likely presence or absence of conditions, other than transplant rejection, that may cause an elevation of immune activity, e.g., autoimmune diseases, autoimmune and chronic inflammatory diseases, chronic inflammatory diseases, systemic infection.

INTRODUCTION

Kidney transplantation is the preferred treatment for end-stage kidney disease (ESKD) to reduce long term mortality as well as improve quality of life in this patient population (Thongprayoon, C. et al., *J. Clin. Med.* 2020; 9(4), 1193). Ongoing monitoring of kidney transplants is required for post-transplantation management, and assessment of kidney function through serum creatinine levels is the most common approach (Baker, R. J. et al., *BMC Nephrol.* 2017; 18(1), 174). Surveillance biopsies are also performed in a subset of patients with elevated risk for acute or chronic rejections (Mehta, R. et al., *Clin. Transplant.* 2017; 31(5)). Over the past few decades, advancements in the understanding of post-transplant care and immunosuppressive medication have markedly improved 1-year outcomes in kidney transplantation (Hart, A. et al., *Am. J. Transplant.* 2018; 18 Suppl 1, 18-113). However, traditional tests used to monitor graft function do not have the ability to detect immune activation to optimize immunosuppression therapy. Early detection of immune activation and kidney allograft rejection can allow intervention before the graft develops functional decline and tissue damage which can often be irreversible (Mas, V. R. et al., *Expert Rev. Mol. Diagn.* 2011; 11(2), 183-196. Lo, D. J. et al., *Nat. Rev. Nephrol.* 2014; 10(4), 215-225. Bontha, S. V. et al., *Am. J. Transplant.* 2017, 17(1), 11-21. Cravedi, P., Mannon, R. B. *Expert Rev. Clin. Immunol.* 2009, 5(5), 535-546). Important to the long-term transplant outcome, monitoring the immune system can also assist to safely reduce immunosuppression in subsets of patients with stable, quiescent immune activity and minimize adverse effects such as infections, malignancy and cardiovascular disease.

Molecular testing enables non-invasive diagnosis of kidney function before invasive tissue biopsy (Mas, V. R. et al., *Expert Rev. Mol. Diagn.* 2011; 11(2), 183-196. Lo, D. J. et al., *Nat. Rev. Nephrol.* 2014; 10(4), 215-225. Bontha, S. V. et al., *Am. J. Transplant.* 2017, 17(1), 11-21. Cravedi, P., Mannon, R. B. *Expert Rev. Clin. Immunol.* 2009, 5(5)). Immune activation allows an entry point for early detection of organ allograft rejection due to the activation of immune cells, with corresponding changes in gene expression in the peripheral blood (Pontrelli, P., *Front. Immunol.* 2020; 11).

A blood 5-gene expression signature, or gene expression profile (GEP), was developed to assess immune quiescence in kidney allograft recipients which, independently or in conjunction with standard clinical assessments, enables the identification of transplant recipients who have a stable condition or low probability of active rejection. The expression levels of the target genes, including low expressing genes, and reference genes in a blood sample were determined using targeted RNA sequencing and molecular tag (MT)/unique molecular identifier (UMI), and the resulting expression profile was converted to a score.

Materials And Methods

Study Design. The third validation cohort included blood and kidney biopsy samples from a 2021 investigator-initiated study at Weill Cornell Medicine, Cornell University, New York, ("Cornell" study), and from the Outcomes of KidneyCare in Renal Allografts ("OKRA") study. The OKRA study (ClinicalTrials.gov Identifier: NCT03326076) is a multicenter, prospective, observational study to evaluate safety and efficacy outcomes in de-novo kidney allograft recipients based on blood gene expression profiling and donor-derived cell-free DNA levels.

Testing Materials and Sample Quality Control. Peripheral blood samples were collected in PAXgene Blood RNA tubes (BD) from healthy non-transplanted individuals and kidney allograft recipients. A minimum of 1 mL whole blood per sample was collected for testing. All transplant patient samples were collected in accordance with the institutional review board with approved study designs at the corresponding institutions and appropriate informed consent. Healthy volunteer samples were collected at the CareDx, Inc. clinical laboratory in accordance with the approved institutional review board at CareDx, Inc. The PAXgene blood samples were shipped at ambient temperature to the CareDx, Inc. clinical laboratory collection or stored at −80° C. prior to shipment to CareDx, Inc. and stored at −80° C. until RNA extraction. Universal Human Reference RNA (UHRR, ThermoFisher) was utilized for the Limit of Detection specificity/LOB study. Known external positive control RNA materials, based on pooled RNA specimens with a predetermined gene expression score, were used in the validation study.

Quality control (QC) metrics for the 5-gene expression signature were developed to ensure accuracy and reproducible test results. Extracted RNA had to pass quality control criteria for concentration and purity prior to testing. The cDNA libraries were quantified and normalized for pool sequencing. The sequencing run had to meet the QC metrics, including the acceptable positive control results, before the testing results were analyzed.

In addition to the blood samples, kidney biopsies from transplant recipients in the validation cohorts were collected for standard histological review. The gene expression profiling results obtained with blood samples and biopsies from Diagnosing Active Rejection in Kidney Transplant Recipients (DART) Study (NCT02424227) cohort were described in Examples 1 and 2. For the OKRA and Cornell studies, histological review of the biopsies followed the Banff 2019 classification criteria (Loupy, A. et al., Am. J. Transplant. 2020, 20(9), 2318-2331). The OKRA study enrolled de-novo kidney allograft patients between Sep. 17, 2019 and Oct. 27, 2021. The inclusion and exclusion criteria for the OKRA study are summarized in Table 6.

TABLE 6

Outcomes Of KidneyCare In Renal Allografts (OKRA) Inclusion And Exclusion Criteria

| Inclusion Criteria | Exclusion Criteria |
|---|---|
| Patient's health care provider adopts and intends to apply the center's AlloSure Routine Testing Schedule as part of the information used to manage the patient.<br>Subjects willing to provide written informed consent to participate. | Exclusions for AlloSure ® Intended Use<br>Specimens from patients for whom any of the following are true will not be tested:<br>Recipients of transplanted organs other than kidney<br>Recipients of a transplant from a monozygotic (identical)<br>Recipients of a bone marrow transplant<br>Recipients who are pregnant<br>Recipients who are under the age of 18<br>Recipients who are less than 14 days post-transplant |

Taken together, a total of 235 kidney transplant biopsy specimens from 222 patients were investigated, in which 66 biopsies from 64 patients were classified as rejection based on histological features and 169 biopsies from 160 patients were classified as non-rejection or quiescence-associated specimens (Table 7). The kidney transplant patients were recipients of kidney allograft alone, first or repeat allograft. Transplant recipients of more than one organ type were excluded from this study.

TABLE 7

Clinical Characteristics of the Prospective, Multi-Center Cohort

| Clinical Characteristics | All | Non-rejection | Rejection | p-value (Non-rejection versus Rejection) |
|---|---|---|---|---|
| Patients, N | 222‡ | 160 | 64 | |
| Samples, N | 235 | 169 | 66 | |
| Race, n (%) | | | | 0.82 |
| Black or African American | 71‡ (32.0) | 50 (31.3) | 22 (34.4) | |
| White | 112‡ (50.4) | 83 (51.9) | 30 (46.9) | |
| Native Hawaiian or Other Pacific Islander | 1 (0.5) | 1 (0.6) | 0 | |
| Hispanic/Latino | 18 (8.1) | 12 (7.5) | 6 (9.4) | |
| Asian | 3 (1.4) | 3 (1.9) | 0 | |
| Other | 7 (3.2) | 5 (3.1) | 2 (3.1) | |
| Unknown | 9 (4.1) | 5 (3.1) | 4 (6.3) | |
| Sex, n (%) | | | | 0.04 |
| Male | 137‡ (61.7) | 106 (66.3) | 32 (50.0) | |
| Female | 79‡ (35.6) | 49 (30.6) | 31 (48.4) | |
| Unknown | 6 (2.7) | 5 (3.1) | 1 (1.6) | |
| Age at enrollment, yr, mean ± SD | 51.2 ± 14.0 | 52.0 ± 13.2 | 49.2 ± 15.6 | 0.19 |
| Age at enrollment, yr, median (IQR) | 54 (41-61) | 54 (43.5, 61) | 48 (38, 60.5) | |
| Post-transplant, d, mean ± SD | 546.6 ± 1020.2 | 424.2 ± 914.5 | 859.9 ± 1202.8 | 0.15 |
| Post-transplant, d, median (IQR) | 136 (79, 390) | 126 (83, 340) | 203.5 (69.25, 1428.5) | |

‡For two patients two biopsies were included in this cohort: one being a rejection and the other a non-rejection.

RNA Purification. Total RNA was purified from whole blood collected in PAXgene RNA tubes using the QIAsymphony PAXgene blood RNA kits (QIAGEN) and the QIAsymphony SP system (QIAGEN) following the manufacturer's instruction. RNA quantity and quality were determined by spectrophotometry (Molecular Devices).

Gene Expression Profiling and RNA-sequencing methodology. A targeted RNA-sequencing panel (QIAseq, Qiagen), which included the five informative genes and 15 reference genes (see Table 4) as well as genomic DNA contamination controls and spike-in controls, was developed and optimized for PAXgene blood RNA samples on an RNA-seq platform using molecular tags (Peng, Q. et al., *BMC Genomics* 2015 August; 16:589-600). Single-read sequencing was performed on Illumina NextSeq 550. Primary analysis of the sequencing data was performed using the Qiagen GeneGlobe QIAseq bioinformatics pipeline for adaptor trimming, read mapping, quality checks, and computing the molecular tag counts (MTs) for the targeted transcripts.

GEP algorithm and bioinformatics pipeline. The gene expression profiling algorithm was fully developed through a bioinformatics cloud-based pipeline that included mapping of reads to the reference genome (GRCh38), read trimming, and counting the molecular tags (MT counts) of individual genes in the signature. The algorithm converted the targeted RNA-Seq MT counts to cycle threshold (CT) values in which the CT values for the informative genes were normalized using the mean CT of the reference genes. The algorithm subsequently calculated gene expression signature scores and associated quality control checks, as described in Example 2. Multiple quality control metrics were evaluated prior to result analysis, including a minimum MT count requirement, minimum total reads, minimum depth (mean reads per MT), acceptable level of control genes, the presence of MT for all target genes, acceptable range of normalized expression for the target genes, maximum average gDNA control MT count, maximum off-target reads, and the acceptable range of the score.

Analytical validation and analysis. A set of studies was performed to establish the analytical performance characteristics of the GEP assay, including determination of specificity, limit of detection, linearity, accuracy, precision and potential interfering substances. All methods for the sample processing and cDNA library preparation were implemented with sample tracking and laboratory workflow management and in-process quality controls (IPQCs) to generate pooled cDNA libraries for sequencing. Validation was performed over 20 testing days and by three operators. Statistical analysis was performed using JMP version 13 (SAS) or R (The R Foundation for Statistical Computing, Vienna, Austria). Analytical parameters were computed following the guidance provided by the Clinical and Laboratory Standards Institute guidance document EP17-A2.

Specificity. The specificity of the GEP assay was determined for blank controls based on analysis of the testing results: "data presence" and the ability to generate gene expression signature scores in all the replicates. For limit of detection (LOD) determination, a probit analysis was applied to estimate the input RNA level at which 95% of the replicates had detectable transcripts of a low expression gene in the sample (LOD95).

Accuracy. Accuracy was analyzed using the slope and intercept from regression along with the p-values for the test slope=1. In addition, the p-value was determined for pairwise t-test for the difference between two in-house developed methodologies, a manual method (method 1) as well as a scaled and automated clinical-grade workflow (method 2). Precision was analyzed at the level of operator and run-to-run variability with ANOVA with random effect "Operator" and "Run nested in Operator". Total standard deviation (square root of the sum of square of SD for each component) and % CV for the gene expression signature scores were calculated for intra-run, inter-run, and operator-to-operator variability and reproducibility.

Results

Clinical-Grade GEP Assay Performance Characteristics.

Figure 10B:
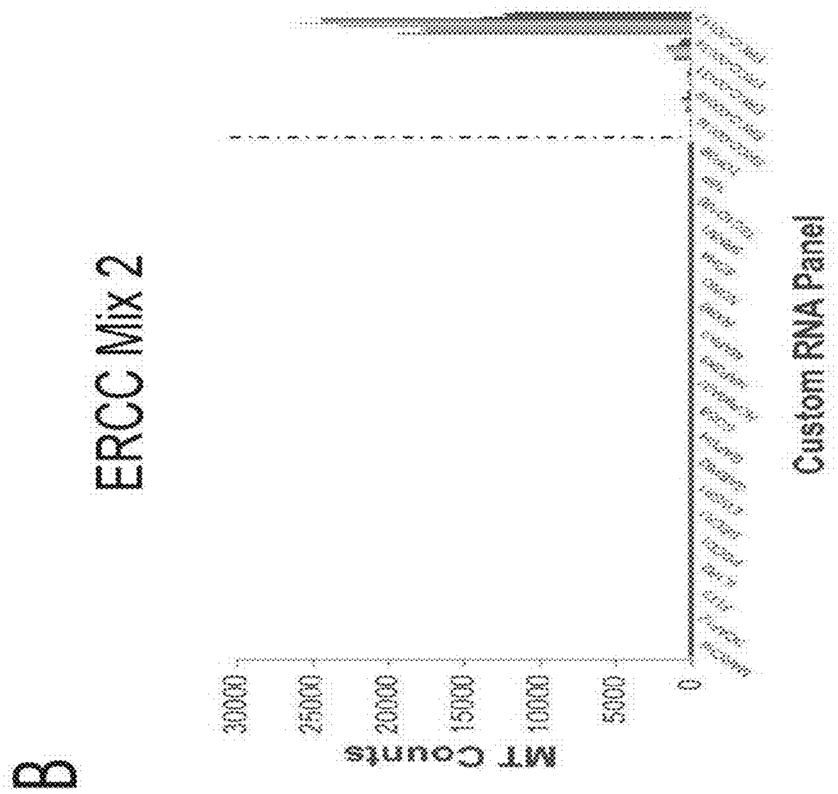
FIGS. 10A-10B show exemplary characteristics of the blank (no template) controls for the use of the 5-gene expression signature, demonstrating specificity in accordance with embodiments of the disclosure. Each control contains RNA, but does not contain the specific RNA species used in the 5-gene expression signature.
Figure 10A:
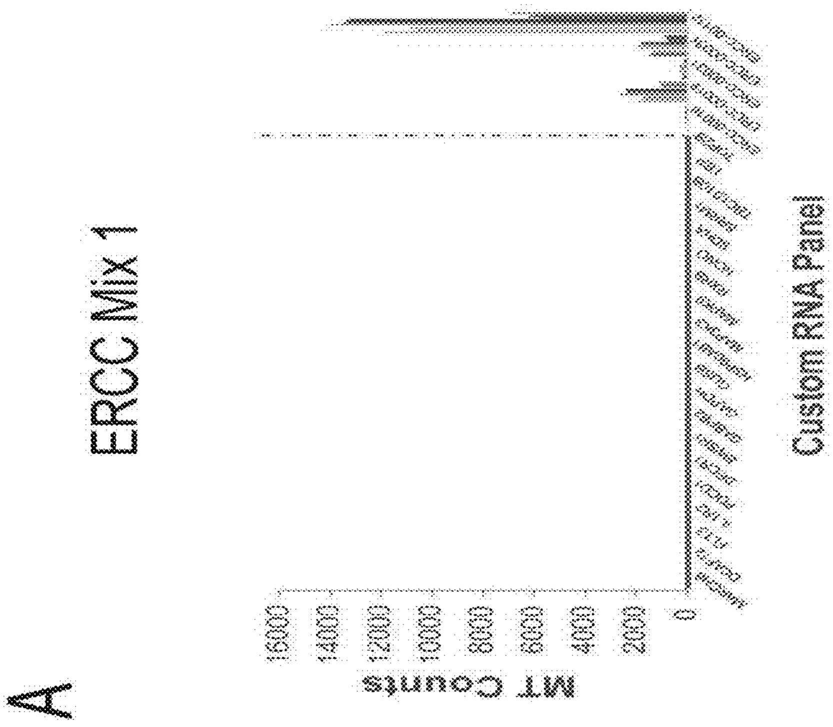

Specificity. The 5-gene expression signature comprises genes with both positive and negative influences on the gene expression score. To define the specificity of the test, the expected characteristics of a blank were determined by analysis of the 5-gene set in an RNA mixture that does not contain human genes but does contain control transcripts. This was accomplished by using two independent external RNA controls consortium (ERCC) RNA control mixes. These artificial synthetic transcripts do not contain any of the informative or reference gene sequences. Each control mix was processed in four replicates for each experiment and repeated three times. Gene expression levels, as measured by the molecular tag (MT) counts, were evaluated for the informative genes and for the ERCC-specific spike-in transcripts. Analysis of the 12 replicated blank controls for the ERCC-specific transcripts were always >10 MT counts, ranging from an average MT count of approximately 50 to over 18,000. Most of the informative genes-specific transcripts (18 of 20) were expressed at an average MT count below 1 (FIG. 10). The gene expression algorithm does not compute the cycle threshold (ct) values for MT counts less than 1. Therefore, in all of these replicates there were no results for any informative genes and only "blanks," as expected.

Figure 11:
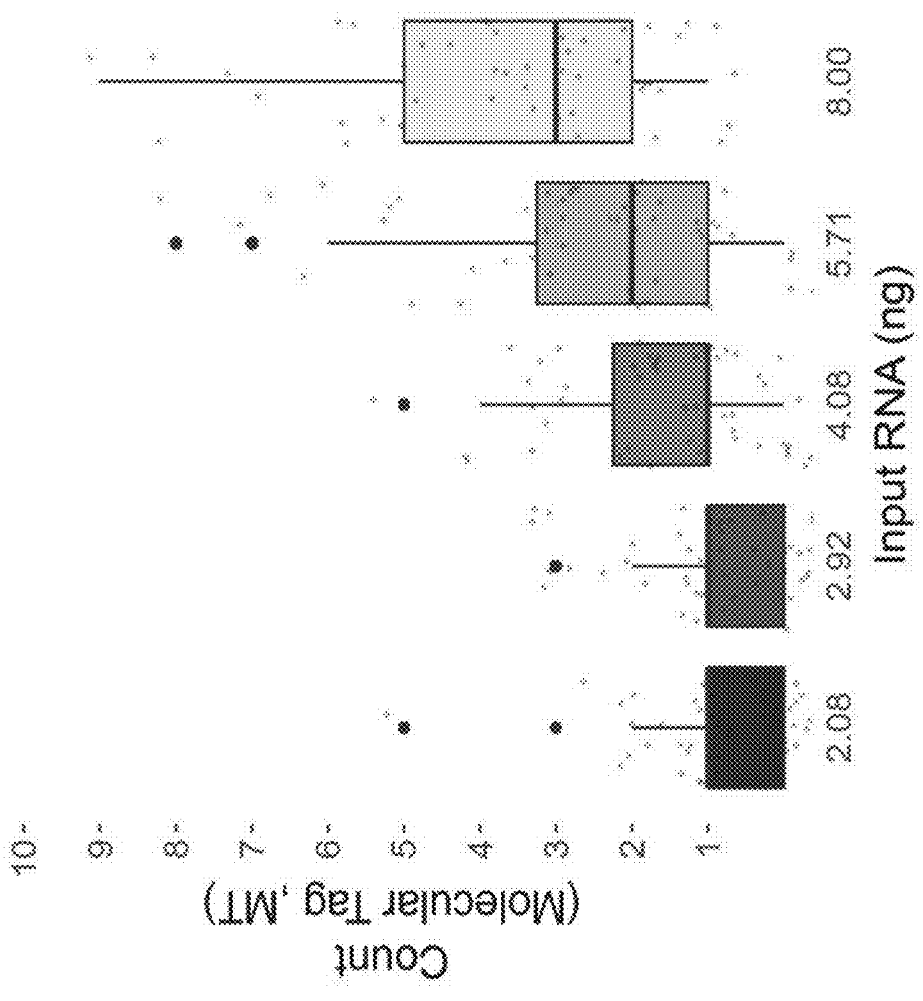
FIG. 11 shows an exemplary assessment of the limit of detection (LOD) for the use of the 5-gene expression signature, in accordance with embodiments of the disclosure. FLT3, one of the five informative genes, exhibits the lowest average expression levels in PAXgene whole blood RNA, therefore the limit of detection was defined by determining the lowest RNA input for which the expression level of FLT3 could be reliably measured.

Limit of Detection (LOD). Among the five informative genes of the GEP assay (MARCH8, DCAF12. FLT3, IL1R2, PDCD1), FLT3 is expressed at the lowest average levels in the Paxgene whole blood RNA. The Limit of Detection (LOD) was, therefore, defined by determining the lowest RNA input for which the expression level of FLT3 could be reliably measured. The universal human reference RNA (UHRR, an RNA mix from 10 pooled cancer cell lines) was used as control material to determine LOD in a commercial reference material that could serve as a control in future testing (Xu, J. et al., *Scientific data* 2014, 1.) The samples were run at five different concentrations (FIG. 11) in six separate runs and eight replicates per concentration. The concentrations were chosen based on previous data defining the approximate LOD, as described in Example 2. To calculate the LOD, a probit regression analysis was applied to determine the input RNA level at which 95% of the replicates had detectable FLT3 transcripts (LOD95). Accordingly, the resulting LOD for the 5-gene expression signature was 6.3 ng of input RNA per library (95% confidence interval (CI): [5.4, 8.0]) (FIG. 11).

Figure 12A:
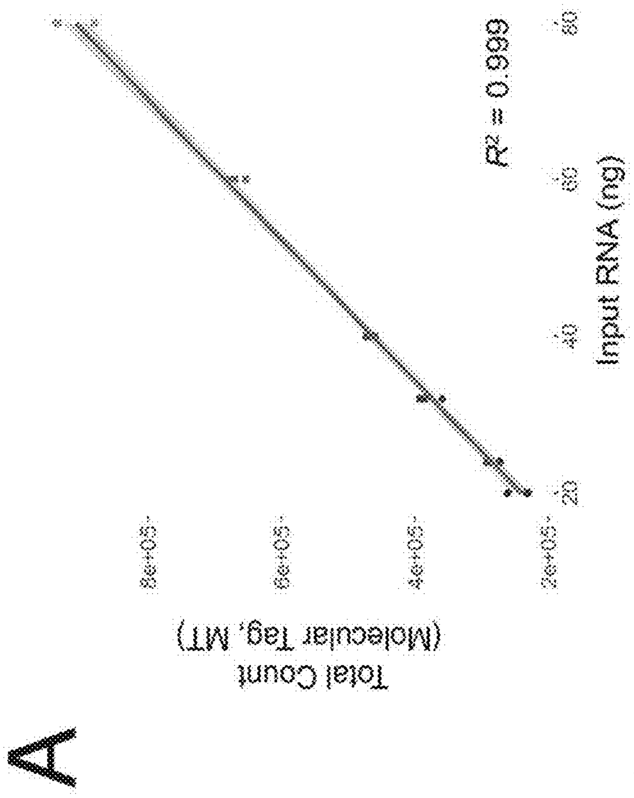
FIGS. 12A-12B provide exemplary linearity characteristics for the use of the 5-gene expression signature, in accordance with embodiments of the disclosure.
Figure 12B:
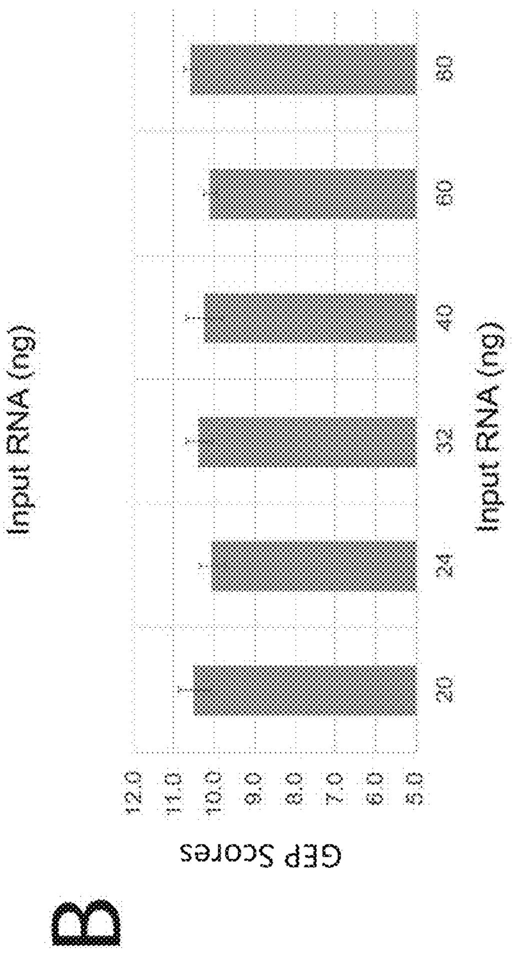

Assay Linearity. Assay linearity was evaluated within the range of RNA input amounts previously defined as acceptable inputs for generation of the targeted RNA seq libraries (20 to 80 ng per library) and covered a 2-fold range above and below the standard input RNA amount of 40 ng/library. The total MTs for all transcripts as well as for individual genes in the panel showed excellent correlation with the input RNA amount (Table 8 and FIG. 12A). The correlation coefficients of MT counts for all the informative genes with RNA input were >98%, ranging from 98.3% to 99.9% (Table 8). The gene expression score had a mean of 10.3 and an SD of 0.22 across the range of input RNAs, demonstrating that the gene expression signature scores across the range tested were consistent regardless of the input RNA amount (p-value=0.3084, FIG. 12B).

TABLE 8

Linearity Testing for Individual Genes: Coefficient of Determination and Correlation Coefficient of Molecular Tag Counts

| Gene | Coefficient of Determination ($R^2$) | Correlation Coefficient (R) |
|---|---|---|
| MARCH8 | 0.9974 | 99.87% |
| DCAF12 | 0.9986 | 99.93% |
| FLT3 | 0.9712 | 98.55% |
| IL1R2 | 0.9941 | 99.70% |
| PDCD1 | 0.9664 | 98.31% |
| DECR1 | 0.9983 | 99.91% |
| EWSR1 | 0.9973 | 99.86% |
| GABPB2 | 0.9973 | 99.86% |
| GAPDH | 0.9992 | 99.96% |
| GUSB | 0.9970 | 99.85% |
| HSP90AB1 | 0.9968 | 99.84% |
| MAP3K3 | 0.9979 | 99.89% |
| MAPK9 | 0.9977 | 99.88% |
| NONO | 0.9976 | 99.88% |
| RXRB | 0.9953 | 99.76% |
| SDHA | 0.9977 | 99.88% |
| SRRM1 | 0.9976 | 99.88% |
| TBC1D10B | 0.9955 | 99.77% |
| TBP | 0.9982 | 99.91% |
| TOP2B | 0.9981 | 99.90% |

Accuracy. Accuracy was evaluated by comparing the gene expression signature scores from two workflows, namely a manual workflow (Method 1) and a high-throughput, automated clinical-grade workflow (Method 2). Twenty-six PAXgene blood RNA samples with known biopsy-proven rejection or non-rejection diagnosis were tested in three replicates per workflow. A mean gene expression score was calculated across replicates and then compared between the two workflows. The observed differences in gene expression signature scores ranged from −0.77 to 0.56 with a mean gene expression score difference of 0.00 between the two workflows (Table 9). The regression analysis showed a correlation coefficient of 0.997, and the pairwise t-test between the manual and automated clinical-grade workflows showed no bias between workflows (intercept: 0.33, slope: 0.97, p-value: 0.47 for gene expression score difference. These results demonstrate the accuracy of the automated clinical-grade workflow to faithfully reproduce the results obtained with method 1 and as described in Examples 1 and 2.

TABLE 9

Accuracy Characteristics. Comparison of the gene expression profiling (GEP) scores from a manual workflow (Method 1) and a high-throughput, automated clinical-grade workflow (Method 2).

| Sample | Clinical Classification | Mean GEP Score Method 1 | Mean GEP Score Method 2 | Difference in GEP score Method 1 vs. Method 2 |
|---|---|---|---|---|
| 1 | NR | 2.61 | 2.55 | 0.06 |
| 2 | NR | 5.48 | 6.25 | −0.77 |
| 3 | Q | 6.16 | 6.82 | −0.67 |
| 4 | Q | 6.61 | 6.94 | −0.33 |
| 5 | NR | 7.76 | 7.85 | −0.09 |
| 6 | Q | 8.35 | 8.72 | −0.37 |
| 7 | Q | 9.14 | 9.21 | −0.08 |
| 8 | NR | 9.45 | 8.99 | 0.46 |
| 9 | Q | 9.68 | 9.80 | −0.12 |
| 10 | Q | 9.75 | 9.79 | −0.03 |
| 11 | Q | 10.00 | 9.89 | 0.11 |
| 12 | Q | 10.16 | 10.20 | −0.04 |
| 13 | Q | 10.29 | 10.33 | −0.04 |
| 14 | Q | 10.37 | 10.23 | 0.14 |
| 15 | NR | 11.06 | 10.67 | 0.39 |
| 16 | ABMR | 11.28 | 10.72 | 0.56 |
| 17 | TCMR | 11.38 | 11.23 | 0.14 |
| 18 | TCMR | 11.69 | 11.62 | 0.08 |
| 19 | TCMR | 12.30 | 12.16 | 0.14 |
| 20 | ABMR | 12.44 | 12.24 | 0.21 |
| 21 | ABMR | 12.45 | 12.45 | 0.01 |
| 22 | ABMR | 12.62 | 12.86 | −0.24 |
| 23 | TCMR | 13.60 | 13.57 | 0.03 |
| 24 | ABMR | 13.98 | 13.79 | 0.19 |
| 25 | ABMR | 14.52 | 14.37 | 0.15 |
| 26 | TCMR | 15.73 | 15.55 | 0.18 |
| Average difference in GEP score | | | | 0.00 |

Q—Quiescence; ABMR—antibody-mediated rejection; TCMR—T cell mediated rejection, NR—non-rejection.

Precision. Assay precision was evaluated across operators, across runs, and within runs, with eight specimens tested by 3 operators and with 3 runs per operator (run in triplicates, n=27 per specimen, 216 data points total). Consistently, the variations observed between operators and the testing process were well below 5%. The average total standard deviation for each sample at different gene expression signature scores was less than 0.75, ranging from 0.29 to 0.71 (Table 10). The combined analysis of both operator and process variation showed a coefficient of variation of 0.049. These data indicated that the operator, intra-run and inter-run variability did not introduce significant variation in determining the gene expression signature scores.

TABLE 10

Precision Study.

| Sample | N | Mean | Operator-to-Operator SD | Run-to-Run SD | Replicate-to-Replicate SD | Subtotal (Run + Replicate) SD | Total SD |
|---|---|---|---|---|---|---|---|
| 1 | 27 | 7.08 | 0.08 | 0.00 | 0.69 | 0.69 | 0.69 |
| 2 | 27 | 12.60 | 0.00 | 0.23 | 0.43 | 0.49 | 0.49 |
| 3 | 27 | 9.80 | 0.00 | 0.00 | 0.62 | 0.62 | 0.62 |
| 4 | 27 | 12.28 | 0.00 | 0.00 | 0.45 | 0.45 | 0.45 |
| 5 | 27 | 11.23 | 0.00 | 0.00 | 0.46 | 0.46 | 0.46 |
| 6 | 27 | 10.61 | 0.00 | 0.11 | 0.63 | 0.64 | 0.64 |
| 7 | 27 | 14.06 | 0.09 | 0.00 | 0.28 | 0.28 | 0.29 |
| 8 | 27 | 10.93 | 0.41 | 0.23 | 0.53 | 0.58 | 0.71 |

Interfering Substances. Six potential interfering substances for the gene expression profiling were tested: acetaminophen, acetylsalicylic acid, bilirubin, genomic DNA, hemoglobin, and triolein. Genomic DNA was the only substance that was identified as an interfering substance. Samples that failed due to genomic DNA contamination did not generate sequencing libraries that passed yield QC criteria because they failed at the library construction prior to sequencing. To additionally safeguard against any potential genomic DNA contamination for the gene expression profiling, six internal controls were included in the gene expression profiling assay to detect the presence of genomic DNA in the RNA samples. Since insufficient libraries were generated for samples with genomic DNA contamination that failed to pass in-process QC and, consequently, scores were not computed for samples that failed the QC criteria, genomic DNA contamination of RNA samples did not negatively impact test performance or gene expression signature scores.

Figure 13:
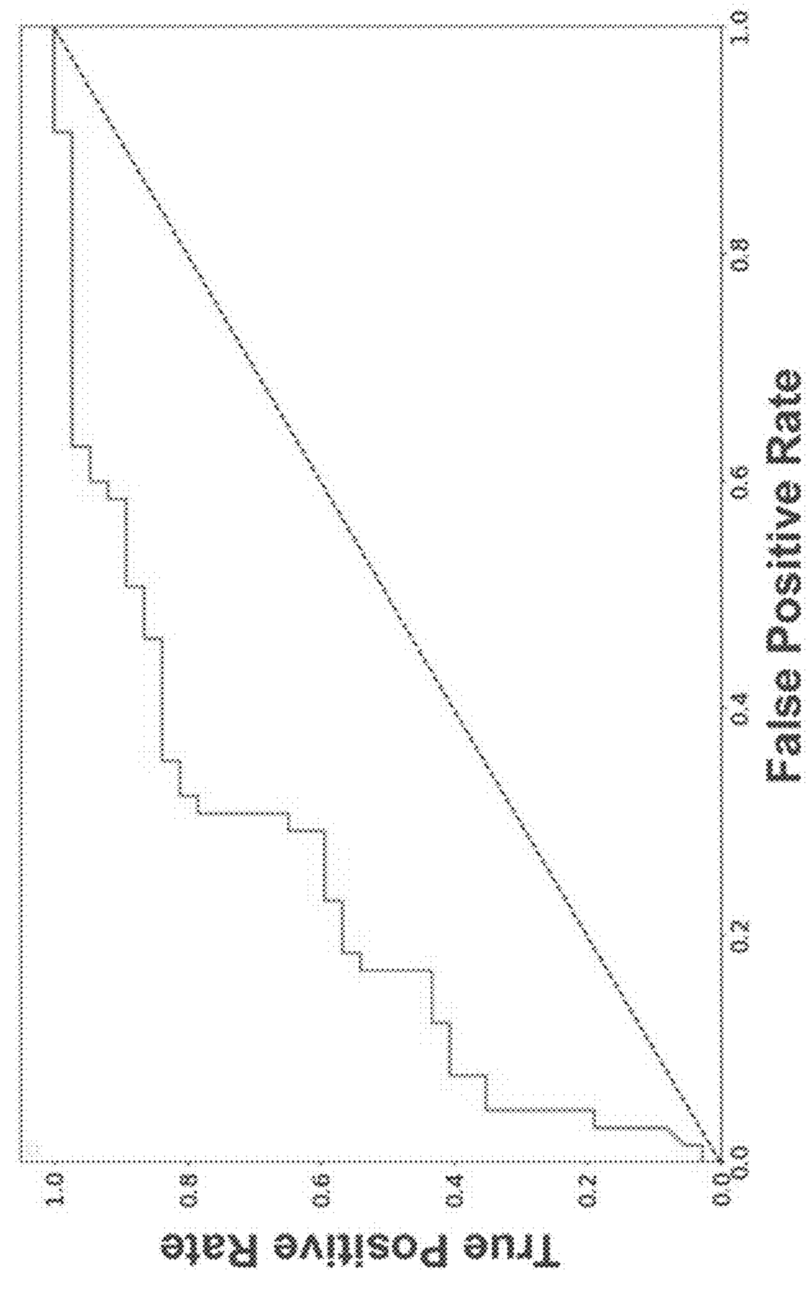
FIG. 13 shows an exemplary ROC plot for the third validation cohort, differentiating the transplant status of renal transplant recipients who experienced allograft rejection from the transplant status of non-rejecting renal transplant recipients with an AUC of 0.78 (95% CI: 0.69-0.87), in accordance to embodiments of the disclosure.

Clinical Validation Cohort comprising 102 biopsies and biopsy-paired blood samples. Only blood samples that were paired with a kidney allograft biopsy were included in the third validation cohort. To be considered biopsy-paired, the blood sample had to be drawn 30 or fewer days prior to the biopsy. For biopsies with multiple blood samples collected for gene expression testing, only the gene expression score of the most recent blood sample relative to the biopsy was included in the analysis. In the third validation cohort, 102 biopsies from 99 patients were evaluated; the timepoints for these biopsies ranged from 7 to 5,927 days post-transplantation with a median of 111.5 days (74.25 to 195.25 days). All biopsy reports were scored by a central pathologist according to the Banff 2019 guidelines (Loupy, A. et al., *Am. J. Transplant.* 2020, 20(9), 2318-2331). Kidney transplant recipients who were diagnosed with ABMR, TCMR or mixed rejection were compared to kidney transplant recipients with no rejection. Borderline rejection, suspicious ABMR and other pathologies were excluded, except for interstitial fibrosis and tubular atrophy (IFTA). Of the 102 biopsies there were 37 rejections, 11 ABMR, 16 TCMR and 10 mixed rejections. The corresponding blood samples were collected a median of 11 days prior to biopsy, and the 5-gene expression profiling tests were performed in the CareDx, Inc. clinical laboratory. In this third validation cohort, the 5-gene expression signature accurately differentiated rejection from non-rejection with a ROC AUC of 0.78 (95% ci: 0.69-0.87) which is consistent with previous validation studies, as described in Example 2 (FIG. 13).

Combined Cohort comprising 235 biopsies and biopsy-paired blood samples. To further characterize the clinical performance of the 5-gene expression signature, its performance across a large, diverse transplant patient population was investigated by combining the data of the clinical validation cohort described above with the data from the cohorts described in Examples 1 and 2.

Altogether, this combined data set included a total of 235 samples (66 rejection and 169 non-rejection or quiescence) from 222 kidney transplant recipients. The demographic description of this study population is illustrated in Table 7. The mean age of this cohort was 51.2±14.0 years with 61.7% males and 35.5% females. Among the 222 patients, 50.4% were Caucasians, 31.9% African Americans and 8.1% Hispanics. There was no difference in age and race between the rejection and non-rejection cohorts although there were more male patients in the rejection cohort (66% vs 50%, p-value=0.04). Deceased donors constituted 64.8% transplant patients, 30.1% living donors and 5.1% unknown. Of the 222 patients, 33 (14.8%) were repeat kidney transplants and 182 (81.9%) were first-time kidney transplants. Transplant recipients with more than one organ transplant or a transplant other than kidney were not part of the analysis. Transplant recipients were a median of 136 days post-transplant. There was no significant difference between the rejection and non-rejection groups: 126 and 203 days post-transplant, respectively (p-value=0.15).

The gene expression score and its corresponding negative predicted value (NPV) and positive predicted value (PPV) were computed for each sample. As expected, specificity and PPV increased as the gene expression score increased. Conversely, sensitivity and NPV increased as the gene expression score decreased (FIG. 14A). For example, at a gene expression score of 9.0, the NPV was 97% and the PPV was 17% (at the 10% prevalence level, with 89% sensitivity and 52% specificity, FIG. 14A). These performance characteristics were observed across the combined, large and diverse cohort of kidney transplant recipients, indicating the robustness of the 5-gene expression signature assay. FIG. 14B presents the full dataset of the performance characteristics of the 5-gene expression signature assay across all scores. For samples with a gene expression score (GEP score) range from 9.5 to 11.5, the increasing probability of rejection, the specificity and PPV increased accordingly, whereas the sensitivity and NPV increased for samples with gene expression signature scores decreasing from 11.5 to 9.5 range, indicating the decreasing probability of rejections. Based on the analysis from the combined, large and diverse cohort of transplant recipient samples, the sensitivity and specificity graphs intersected at a gene expression score of approximately 10.5. At this score, which simultaneously maximizes for both sensitivity and specificity, the analysis yielded a sensitivity of 70% and a specificity of 66% for the diagnosis of transplant rejection. The corresponding NPVs for transplant rejection were 95% and 87% at 10% and 25% prevalence of rejection, respectively, whereas the PPVs were 18% and 40% at 10% and 25% prevalence of rejection, respectively.

Combined Assessment of 5-Gene Expression Signature and Dd-cfDNA Levels

For each transplant recipient for whom paired dd-cfDNA and GEP samples, obtained within 30 days prior to biopsy, were available, dd-cfDNA levels were determined using AlioSure®. For dd-cfDNA, validated levels of 0.5% and 1% were evaluated. At a threshold of 0.5%, dd-cfDNA had a sensitivity of 85.7% and specificity of 75% in the determination of rejection; at a threshold of 1%, dd-cfDNA had a sensitivity and specificity of 59.5% and 84.5%, respectively, in the determination of rejection. For the 5-gene expression profiling (GEP), score thresholds of 10.5 and 11.5 were evaluated. At a score threshold of 10.5, the GEP assay had a sensitivity and specificity of 69%; at a score threshold of 11.5, the GEP assay had a sensitivity and specificity of 52% and 83%, respectively.

For the GEP and dd-cfDNA combination with a GEP score of 10.5 and dd-cfDNA levels of 0.5%, the sensitivity and specificity for rejection were 93% and 51%, respectively, with a corresponding negative predictive value (NPV) of 96% at 25% prevalence of rejection and NPV of 98% at 10% prevalence of rejection (Table 11). The benefit of a negative predictive value lies in its indication that a rejection can be ruled out with a certain likelihood. High negative predictive values, as they are shown in Table 11 for the combined GEP and dd-cfDNA analysis, may be particularly useful for ruling out a rejection, based on which an invasive and unnecessary biopsy can be avoided.

TABLE 11

Performance characteristics for the combined GEP and dd-cfDNA analysis with a GEP score of 10.5 and dd-cfDNA levels of 0.5%

| | Sensitivity (%) | Specificity (%) | NPV (%) (10% prevalence) | NPV (%) (25% prevalence) | PPV (%) (10% prevalence) | PPV (%) (25% prevalence) |
|---|---|---|---|---|---|---|
| dd-cfDNA | 86 | 75 | 98 | 94 | 28 | 53 |
| GEP | 69 | 69 | 95 | 87 | 20 | 43 |
| *GEP+ or dd-cfDNA+ | 93 | 51 | 98 | 96 | 17 | 39 |
| **GEP+ and dd-cfDNA+ | 62 | 93 | 96 | 88 | 50 | 75 |

*GEP and dd-cfDNA combined analysis considered positive (+) when either GEP or dd-cfDNA score is elevated.
**GEP and dd-cfDNA combined analysis considered positive (+) only when both GEP and dd-cfDNA scores are elevated)

For the GEP and dd-cfDNA combination with a GEP score of 11.5 and dd-cfDNA levels of 1%, the sensitivity and specificity for rejection were 31% and 98%, respectively, with a corresponding positive predictive value (PPV) of 84% at 25% prevalence of rejection and PPV of 63% at 10% prevalence of rejection (Table 12).

TABLE 12

Performance characteristics for the combined GEP and dd-cfDNA analysis with a GEP score of 11.5 and dd-cfDNA levels of 1%.

| | Sensitivity (%) | Specificity (%) | NPV (%) (10% prevalence) | NPV (%) (25% prevalence) | PPV (%) (10% prevalence) | PPV (%) (25% prevalence) |
|---|---|---|---|---|---|---|
| dd-cfDNA | 60 | 85 | 95 | 86 | 31 | 57 |
| GEP | 52 | 83 | 94 | 84 | 25 | 50 |
| *GEP+ or dd-cfDNA+ | 81 | 70 | 97 | 92 | 23 | 47 |
| **GEP+ and dd-cfDNA+ | 31 | 98 | 93 | 81 | 63 | 84 |

*GEP and dd-cfDNA combined analysis considered positive (+) when either GEP or dd-cfDNA score is elevated.
**GEP and dd-cfDNA combined analysis considered positive (+) only when both GEP and dd-cfDNA scores are elevated)

Figure 15:
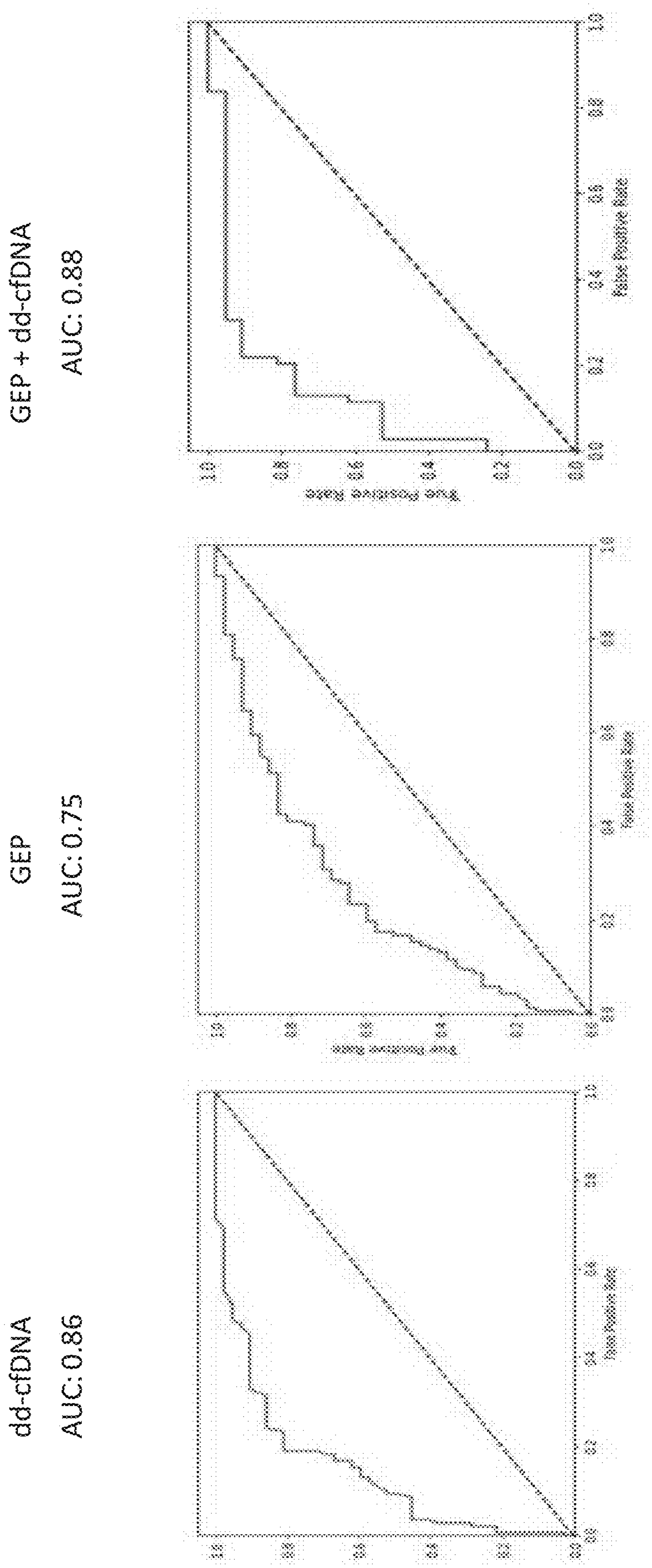
FIG. 15 shows exemplary ROC plots for all three validation cohorts, in accordance with embodiments of the disclosure, for differentiating the transplant status of renal transplant recipients who experienced allograft rejection from the transplant status of non-rejecting renal transplant recipients with an AUC of 0.86 for assessing dd-cfDNA levels alone, an AUC of 0.75 for assessing the 5-gene expression signature alone, and an AUC of 0.88 for the combined analysis of dd-cfDNA levels and 5-gene expression signature.

GEP and dd-cfDNA levels individually differentiated rejection (R) from non-rejection (NR) with an AUC of 0.75 and 0.86, respectively. The AUC for GEP and dd-cfDNA combined analysis was 0.88 (FIG. 15).

Figure 16:
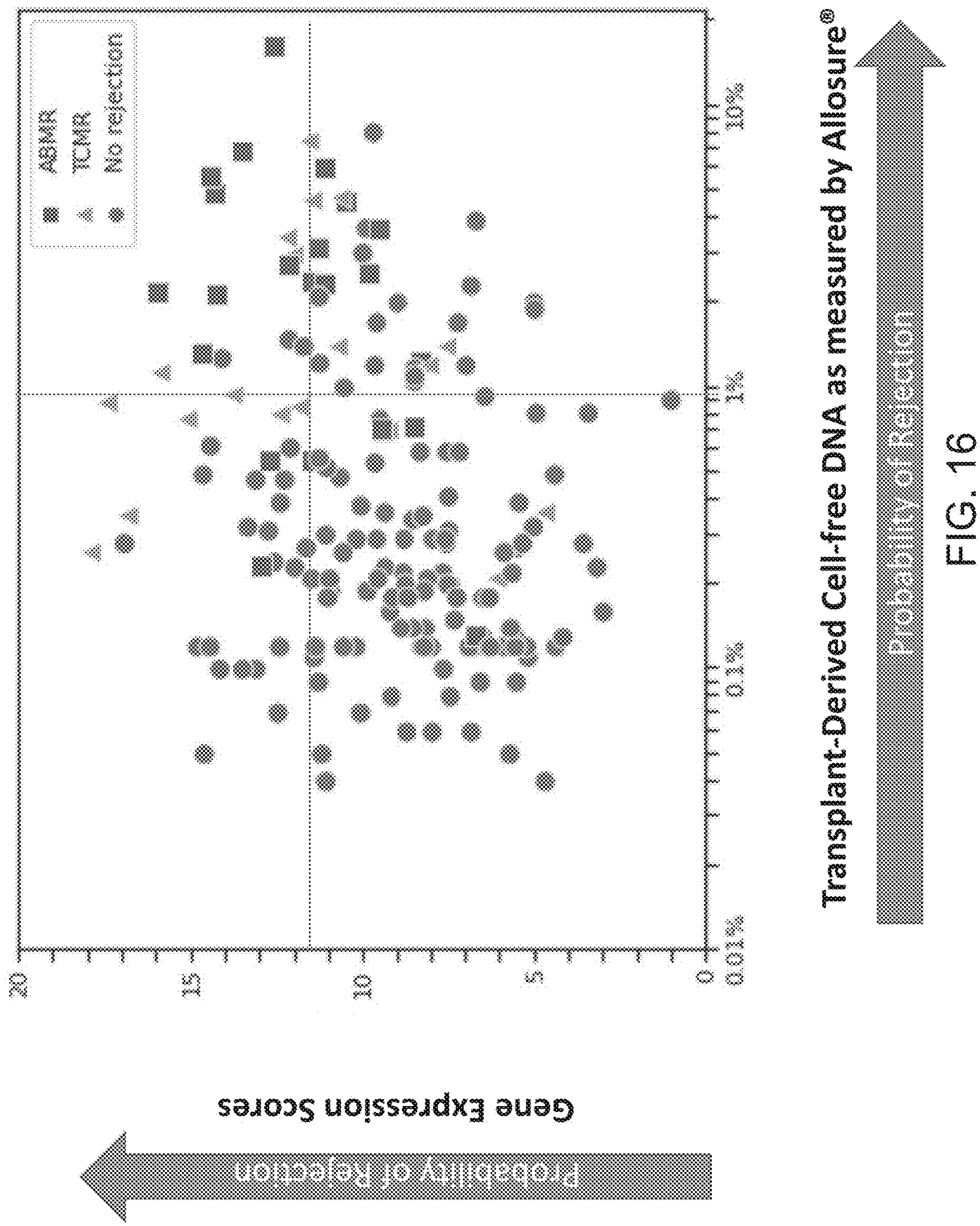
FIG. 16 shows an exemplary scatterplot of all no rejection (quiescence)—indicating combined scores and rejection-indicating combined scores from all validation sets, based on the combined analysis of the 5-gene expression signature (y-axis) and transplant-derived cell-free DNA levels, as measured by AlloSure® (x-axis). Circles indicate no rejection (quiescence); orange triangles indicate TCMR; blue squares indicate ABMR.

The combined analysis of GEP and dd-cfDNA levels made possible not only to differentiate rejection from non-rejection, but also to differentiate TCMR and ABMR. FIG. 16 illustrates how the no-rejection (quiescence)—indicating combined scores and rejection-indicating combined scores from all validation sets, based on the combined analysis of the 5-gene expression signature (y-axis) and transplant-derived cell-free DNA levels, are distributed across four quadrants formed by the various analysis thresholds. For example, at the transplant donor-derived cfDNA (dd-cfDNA) analysis threshold of 1% and the gene expression profile (GEP) score threshold of 11.5, as shown by the vertical and horizontal lines in the figure, the vast majority of no-rejection (quiescence)—indicating combined scores is concentrated within the lower left quadrant, characterized by low gene expression signature scores and low dd-cfDNA levels, whereas the majority of rejection-indicating combined scores is concentrated within and close to the upper right quadrant, characterized by high gene expression signature scores and high dd-cfDNA levels. Among the rejection-indicating combined scores, there is a noticeable separation of TCMR and ABMR, with TCMR being associated with higher GEP scores, i.e., beyond the GEP score threshold of 11.5, in combination with lower dd-cfDNA levels, i.e. below the dd-cfDNA threshold of 1%. ABMR is also associated with higher GEP scores but combined with dd-cfDNA levels that are higher when compared to TCMR. These associations are shown as a probabilities in FIGS. 17A-C based on the relationship of gene expression scores and transplant-derived cell-free DNA levels or amounts without the use of combined scores, with separate probability plots for TCMR (FIG. 17B), ABMR (FIG. 17C), and overall rejection (FIG. 17A). These results demonstrate the ability of the combined analysis to discriminate ABMR from TCMR based on the probability of either type of rejection for a given relationship of gene expression score and transplant donor-derived cell-free DNA (dd-cfDNA) levels or amounts, as illustrated in the explanatory key for FIGS. 17A-C. The relationship of gene expression score and transplant donor-derived cell-free DNA (dd-cfDNA) levels or amounts reflects the various statuses of a transplant, or the likelihood thereof, and provides an approach to interpret diverging results and to identify or indicate conditions, other than transplant rejection, that may cause an elevation of immune activity. For example, when the combined analysis indicates elevated immune activity (absence of quiescence, as indicated by a gene expression signature score at or above a certain cut-off value) in combination with a low likelihood of allograft rejection and allograft injury (as indicated by transplant donor-derived cell-free DNA (dd-cfDNA) amounts or levels at or below a cut-off value), then one or more conditions, other than transplant rejection, that may cause an elevation of immune activity, such as, e.g., autoimmune and/or chronic inflammatory diseases, systemic infection might be present. Furthermore, for example, when the combined analysis indicates an absence of elevated immune activity (a state of quiescence, as indicated by a gene expression signature score at or below a certain cut-off value) in combination with a high likelihood of allograft rejection and allograft injury (as indicated by transplant donor-derived cell-free DNA (dd-cfDNA) amounts or levels at or above a cut-off value), then the allograft injury is more likely caused by antibody-mediated rejection that is more dependent on existing antibodies or antibodies produced consistently than by T cell mediated rejection which is often associated with an acute activation of the immune system.

The high negative predictive values for the combined GEP and dd-cfDNA analysis in the detection of TCMR, as shown in Table 13, and in the detection of ABMR, as shown in Table 14, provide a health care provider an excellent tool for "ruling out" allograft rejection and, thus, for avoiding unnecessary biopsies. Furthermore, the combined GEP and dd-cfDNA analysis also makes possible to detect or rule out a state of immune activation that is caused by an infection only, as may be characterized by higher GEP scores and low (or lower) dd-cfDNA levels.

TABLE 13

Combined GEP and dd-cfDNA Analysis in the Detection of TCMR

| Analysis, threshold | Sensitivity (%) | Specificity (%) | NPV (%) | PPV (%) |
|---|---|---|---|---|
| dd-cfDNA, 0.5% | 79 | 75 | 97 | 26 |
| dd-cfDNA, 1% | 47 | 85 | 94 | 26 |
| GEP, 10.5 | 74 | 69 | 96 | 21 |
| GEP, 11.5 | 58 | 83 | 95 | 27 |

TABLE 14

Combined GEP and dd-cfDNA Analysis in the Detection of ABMR

| Analysis, threshold | Sensitivity (%) | Specificity (%) | NPV (%) | PPV (%) |
|---|---|---|---|---|
| dd-cfDNA, 0.5% | 91 | 75 | 99 | 29 |
| dd-cfDNA, 1% | 70 | 85 | 96 | 34 |
| GEP, 10.5 | 65 | 69 | 95 | 19 |
| GEP, 11.5 | 48 | 83 | 93 | 24 |

SUMMARY

Here, the validation of a blood 5-gene expression signature is described that is derived from relevant immunologic responsive genes, utilizes targeted RNA sequencing and informs on immune quiescence, T cell-mediated rejection (TCMR), antibody-mediated rejection (ABMR), and mixed rejections.

The limit of detection (LOD) for the GEP assay was established to be 6.3 ng per library of input RNA. Given that the standard input amount for a clinical sample is typically 40 ng per library, this amount is approximately more than 6-fold above the LOD.

The GEP assay uses a digital RNA sequencing platform based on the use of unique molecular identifiers as molecular tags. This allows the unbiased and accurate quantification of mRNA transcripts in a sample, improving the detection of low expression genes. The consistency of gene expression signature scores across RNA input indicates that the score remains robust across the test range for the GEP assay. The correlations were retained at the individual gene level with >98% correlation across inputs, demonstrating the power of the platform to robustly quantify mRNA transcripts across the 5 informative and 15 reference genes.

Furthermore, a common interference to the test performance characteristics observed in molecular assays involving RNA is the presence of contaminating genomic RNA. During the development and validation of the GEP assay, features were included to mitigate the risk of contamination by the amplification of sequences unique to gDNA. If DNA contamination was detected, the automated in-process QC criteria would cancel the next steps in the workflow. The stringent approach ensured that the samples that failed due to genomic DNA contamination would be disqualified at library construction prior to sequencing. Therefore, no gene expression signature scores were generated for these samples and there would be no risk of inaccurate scores being reported to patients.

The validation data demonstrate that the GEP assay can reliably measure the expression of informative genes in kidney allograft recipients to discriminate rejection from quiescence with a negative predictive value of 95% and 87% at prevalence levels of 10% and 25%, respectively.

In this clinical-grade validation study the GEP assay demonstrated a high concordance with the histological outcome of the associated biopsies. The GEP assay reliably and accurately reported a score for each individual sample, ranging from 0 to 20, and the corresponding NPV and PPV that provide the probability of the absence or presence of rejection, respectively. Within the gene expression score range most frequently observed in this study (5 to 16), the NPV range was from 91%-98% at 10% prevalence of rejection and from 76%-93% at 25% prevalence of rejection, respectively. A gene expression score can provide different utility in different transplant patient populations. For instance, a gene expression score of 10.5 achieved the combination of sensitivity (70%), specificity (66%), and 95% NPV, whereas the score of 11.5 achieved equivalent NPV (94%) with lower sensitivity (50%) but better specificity (82%). Clinicians might desire to manage transplant patients with a high risk of rejection early post-transplantation using a lower GEP score with a higher associated NPV. In contrast, healthy stable transplant patients in a population with a low prevalence of rejection might be managed using a higher GEP score with enhanced specificity for rejection. Together, these validation study results demonstrate that the GEP assay is suited for clinical use.

The combined assessment of the 5-gene expression signature and dd-cfDNA levels provided better performance characteristics for determining the probability of rejection. At all the dd-cfDNA and GEP score thresholds used in this analysis, the probability of rejection with an elevated dd-cfDNA was significantly higher if the GEP score was also elevated ($p<0.05$). The combined assessment of the 5-gene expression signature and dd-cfDNA levels improved the sensitivity to "rule out" rejection when both GEP and dd-cfDNA scores were low, as demonstrated by high negative predictive values (NPVs). These NPVs can, thus, be utilized to assess the need for a biopsy when rejection is suspected due to graft dysfunction as well as the need for a protocol biopsy to be performed for subclinical disease. The combined assessment of the 5-gene expression signature and dd-cfDNA levels informs clinicians about possible immune activation (or changes in immune activation) and allograft injury for the management of immunosuppression.

The combined assessment of the 5-gene expression signature and dd-cfDNA levels allows the opportunity to further explore personalizing maintenance immunosuppression or quantitatively considering the reduction of immunosuppression in quiescent patients. Significantly, the increased specificity that resulted from the combined analysis of GEP+dd-cfDNA provides an enhanced confidence to "rule in" rejection when the test scores are high. As remote patient monitoring and telemedicine become routine practice, identifying at-risk patients who may need a biopsy improves the utility of detecting rejection with a higher probability.

What is claimed is:

1. A method of detecting T cell-mediated rejection in a kidney transplant recipient having received a kidney transplant, the method comprising:

(a) providing nucleic acids from a first blood sample obtained from the kidney transplant recipient comprising ribonucleic acid (RNA), and providing nucleic acids from a second blood sample obtained from the kidney transplant recipient comprising cell-free nucleic acids that are derived from the kidney transplant and cell-free nucleic acids that are derived from the kidney transplant recipient;

(b) determining an expression level of five genes consisting of DCAF12, FLT3, IL1R2, PDCD1, and MARCH8 in the first blood sample and determining an amount or level of transplant-derived cell-free nucleic acids in the second blood sample;

(c) determining that the kidney transplant recipient is experiencing a T cell-mediated rejection or is at risk of developing the T cell-mediated rejection based on the expression level of the five genes consisting of DCAF12, FLT3, IL1R2, PDCD1, and MARCH8 in the first blood sample and the amount or level of transplant-derived cell-free nucleic acids in the second blood sample; and (d) responsive to the determining in (c), treating either the T cell-mediated rejection or the risk of developing the T cell-mediated rejection by administering to the kidney transplant recipient methylprednisolone, T cell depletion agent rabbit anti-thymocyte globulin (rATG), rapamycin, mycophenolic acid, or any combination thereof.

2. The method of claim 1, wherein the determining the amount or the level of transplant-derived cell-free nucleic acids in (b) further comprises sequencing a panel of selected single nucleotide polymorphisms (SNPs) from the transplant-derived cell-free nucleic acids, wherein the panel of selected SNPs is suitable for differentiating between transplant-derived cell-free nucleic acids and recipient-derived cell-free nucleic acids.

3. The method of claim 1, wherein the first blood sample and the second blood sample are the same sample.

4. The method of claim 1, wherein the expression levels of the five genes consisting of DCAF12, FLT3, IL1R2, PDCD1, and MARCH8 are determined by RNA-sequencing of RNA isolated from the first blood sample.

5. The method of claim 1, wherein the expression levels of the five genes consisting of DCAF12, FLT3, IL1R2, PDCD1, and MARCH8 are normalized relative to an expression level of one or more reference genes.

6. The method of claim 1, wherein the cell-free nucleic acids are DNA.

* * * * *